(12) United States Patent
Paludan et al.

(10) Patent No.: US 7,993,918 B2
(45) Date of Patent: Aug. 9, 2011

(54) TUMOR SUPPRESSION USING PLACENTAL STEM CELLS

(75) Inventors: Casper Paludan, New York, NY (US); James W. Edinger, Belford, NJ (US); Ryhor Harbacheuski, Kearny, NJ (US); RoseAnn Murray, Glen Ridge, NJ (US); Robert J. Hariri, Florham Park, NJ (US); Qian Ye, Livingston, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 796 days.

(21) Appl. No.: 11/888,926

(22) Filed: Aug. 3, 2007

(65) Prior Publication Data
US 2008/0152624 A1 Jun. 26, 2008

(51) Int. Cl.
*C12N 5/00* (2006.01)
(52) U.S. Cl. .................. 435/375; 435/325; 435/377
(58) Field of Classification Search ............... None
See application file for complete search history.

(56) References Cited

U.S. PATENT DOCUMENTS

| | | | |
|---|---|---|---|
| 5,004,681 A | 4/1991 | Boyse et al. |
| 5,192,553 A | 3/1993 | Boyse et al. |
| 5,426,098 A * | 6/1995 | Carlino ............... 514/12 |
| 5,486,359 A | 1/1996 | Caplan et al. |
| 5,591,625 A | 1/1997 | Gerson et al. |
| 5,733,542 A | 3/1998 | Haynesworth et al. |
| 5,750,376 A * | 5/1998 | Weiss et al. ........... 435/69.52 |
| 5,827,740 A | 10/1998 | Pittenger |
| 5,855,619 A | 1/1999 | Caplan et al. |
| 5,916,202 A | 6/1999 | Haswell |
| 5,922,597 A | 7/1999 | Verfaille et al. |
| 5,942,225 A | 8/1999 | Bruder et al. |
| 6,010,696 A | 1/2000 | Caplan et al. |
| 6,022,540 A | 2/2000 | Bruder et al. |
| 6,057,123 A | 5/2000 | Craig et al. |
| 6,087,113 A | 7/2000 | Caplan et al. |
| 6,174,333 B1 | 1/2001 | Kadiyala et al. |
| 6,224,860 B1 | 5/2001 | Brown |
| 6,255,112 B1 | 7/2001 | Thiede et al. |
| 6,281,012 B1 | 8/2001 | McIntosh et al. |
| 6,322,784 B1 | 11/2001 | Pittenger et al. |
| 6,328,765 B1 | 12/2001 | Hardwick et al. |
| 6,328,960 B1 | 12/2001 | McIntosh et al. |
| 6,355,239 B1 | 3/2002 | Bruder et al. |
| 6,365,362 B1 | 4/2002 | Terstappen et al. |
| 6,368,636 B1 | 4/2002 | McIntosh et al. |
| 6,387,367 B1 | 5/2002 | Davis-Sproul et al. |
| 6,387,369 B1 | 5/2002 | Pittenger et al. |
| 6,541,024 B1 | 4/2003 | Kadiyala et al. |
| 6,645,731 B2 | 11/2003 | Terstappen et al. |
| 6,685,936 B2 | 2/2004 | McIntosh et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,153,500 B2 | 12/2006 | Qasba et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,682,803 B2 | 3/2010 | Paludan et al. |
| 7,700,090 B2 | 4/2010 | Heidaran et al. |
| 2001/0038836 A1 | 11/2001 | During et al. |
| 2001/0044124 A1 * | 11/2001 | Bacus ................ 435/7.23 |
| 2002/0123141 A1 | 9/2002 | Hariri |
| 2002/0160510 A1 | 10/2002 | Hariri |
| 2003/0032179 A1 | 2/2003 | Hariri |
| 2003/0044976 A1 * | 3/2003 | Dominko et al. ........ 435/366 |
| 2003/0044977 A1 | 3/2003 | Sakuragawa et al. |
| 2003/0045552 A1 | 3/2003 | Robarge et al. |
| 2003/0096841 A1 | 5/2003 | Robarge et al. |
| 2003/0161818 A1 | 8/2003 | Weiss et al. |
| 2003/0180269 A1 | 9/2003 | Hariri |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri |
| 2004/0048372 A1 | 3/2004 | Hariri |
| 2004/0048796 A1 | 3/2004 | Hariri et al. |
| 2004/0107453 A1 | 6/2004 | Furcht et al. |

(Continued)

FOREIGN PATENT DOCUMENTS

CN 1548529 5/2003

(Continued)

OTHER PUBLICATIONS

Seaberg RM et al. 2003. Stem and progenitor cells: the premature desertion of rigorous definitions. Trends Neurosci 26: 125-131.*

(Continued)

*Primary Examiner* — Lora E Barnhart
(74) *Attorney, Agent, or Firm* — Jones Day

(57) ABSTRACT

The present invention provides methods of suppression of tumor cell proliferation and tumor growth using placental stem cells and placental stem cell populations. The invention also provides methods of producing and selecting placental cells and cell populations on the basis of tumor suppression, and compositions comprising such cells and cell populations.

25 Claims, 40 Drawing Sheets

U.S. PATENT DOCUMENTS

Figure 1:
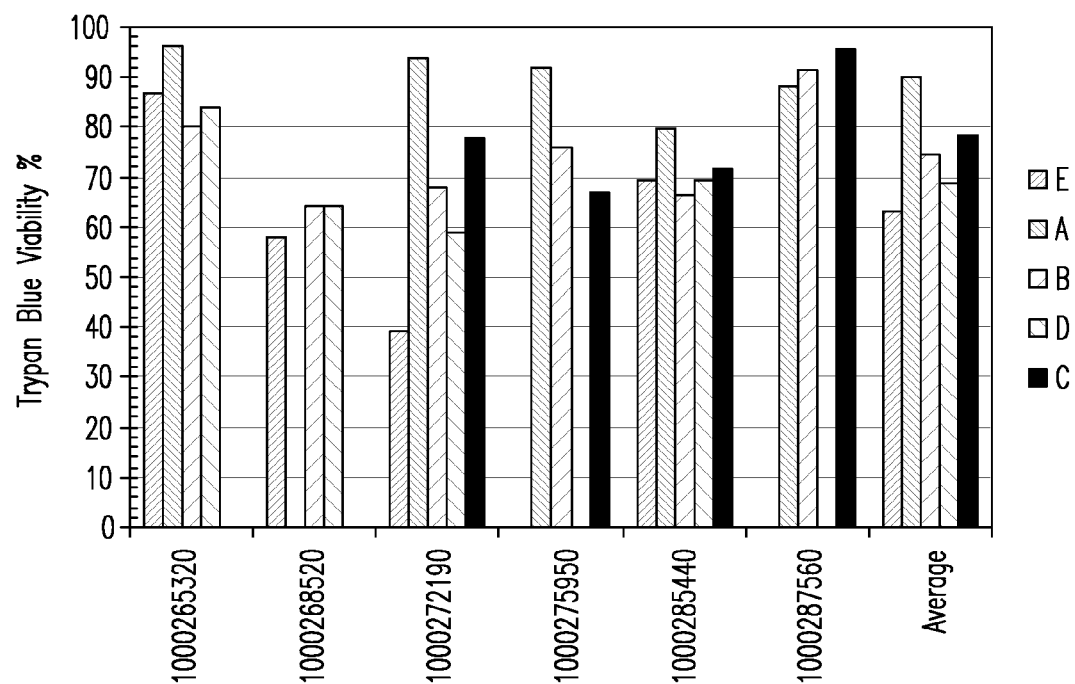

| | | |
|---|---|---|
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0089513 A1 | 4/2005 | Sakuragawa et al. |
| 2005/0112104 A1 | 5/2005 | Pittenger et al. |
| 2005/0118715 A1 | 6/2005 | Hariri |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0276792 A1 | 12/2005 | Kaminski |
| 2005/0282272 A1 | 12/2005 | Bhatia et al. |
| 2005/0283844 A1 | 12/2005 | Furcht et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragaw et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0092497 A1 | 4/2007 | Hariri |
| 2007/0116682 A1 | 5/2007 | Atala et al. |
| 2007/0122903 A1 | 5/2007 | Rezania et al. |
| 2007/0134210 A1 | 6/2007 | Heidaran et al. |
| 2007/0160588 A1 | 7/2007 | Kihm et al. |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0243172 A1 | 10/2007 | Ra et al. |
| 2007/0253931 A1 | 11/2007 | Varney et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0028346 A1* | 2/2010 | Lutz et al. ............ 424/135.1 |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |

FOREIGN PATENT DOCUMENTS

| | | |
|---|---|---|
| EP | 0333328 | 9/1989 |
| EP | 1775341 | 4/2007 |
| JP | 2005151907 | 11/2003 |
| JP | 3934539 | 6/2007 |
| WO | WO 00/27999 A2 | 5/2000 |
| WO | WO 00/27999 A3 | 5/2000 |
| WO | WO 00/69335 | 11/2000 |
| WO | WO 00/73421 | 12/2000 |
| WO | WO 01/21767 | 3/2001 |
| WO | WO 02/46373 A1 | 6/2002 |
| WO | WO 02/063962 A | 8/2002 |
| WO | WO 02/064755 | 8/2002 |
| WO | WO 03/042405 | 5/2003 |
| WO | WO 03/068937 | 8/2003 |
| WO | WO 03/087333 | 10/2003 |
| WO | WO 03/087392 | 10/2003 |
| WO | WO 03/102151 | 12/2003 |
| WO | WO 2004/047770 | 6/2004 |
| WO | WO 2004/071283 | 8/2004 |
| WO | WO 2005/042703 | 5/2005 |
| WO | WO 2005/097190 | 10/2005 |
| WO | WO 2006/015214 | 2/2006 |
| WO | WO 2007/024441 | 3/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/079183 | 7/2007 |
| WO | WO 2007/087293 | 8/2007 |
| WO | WO 2007/089627 | 8/2007 |
| WO | WO 2007/108003 | 9/2007 |
| WO | WO 2008/019148 | 2/2008 |
| WO | WO 2008/051568 | 5/2008 |
| WO | WO 2008/100497 | 8/2008 |
| WO | WO 2009/028870 | 3/2009 |

OTHER PUBLICATIONS

Kavalerchik E et al. 2008. Chronic myeloid leukemia stem cells. J Clin Oncol 26: 2911-2915.*

Ramirez P et al. 2008. Therapy options in imatinib failures. Oncologist 13: 424-434.*

U.S. Appl. No. 09/659,904, filed Sep. 12, 2000, Hariri.
U.S. Appl. No. 11/580,588, filed Oct. 13, 2006, Paludan et al.
U.S. Appl. No. 11/580,625, filed Oct. 13, 2006, Heidaran et al.
U.S. Appl. No. 11/648,802, filed Dec. 28, 2006, Heidaran et al.
U.S. Appl. No. 11/648,804, filed Dec. 28, 2006, Edinger et al.
U.S. Appl. No. 11/648,812, filed Dec. 28, 2006, Heidaran et al.

U.S. Appl. No. 11/648,813, filed Dec. 28, 2006, Edinger et al.
U.S. Appl. No. 11/648,824, filed Dec. 28, 2006, Heidaran et al.
U.S. Appl. No. 11/877,475, filed Oct. 23, 2007, Edinger et al.
U.S. Appl. No. 11/980,012, filed Oct. 29, 2007, Hariri.
U.S. Appl. No. 11/982,007, filed Oct. 31, 2007, Hariri.
U.S. Appl. No. 11/982,291, filed Oct. 31, 2007, Edinger et al.
U.S. Appl. No. 12/187,337, filed Aug. 6, 2008, Heidaran et al.
U.S. Appl. No. 12/267,499, filed Nov. 7, 2008, Heidaran et al.
U.S. Appl. No. 12/341,961, filed Dec. 22, 2008, Hariri.
U.S. Appl. No. 12/544,949, filed Aug. 20, 2009, Zeitlin et al.
U.S. Appl. No. 12/545,029, filed Aug. 20, 2009, Zeitlin et al.
U.S. Appl. No. 12/546,556, filed Aug. 24, 2009, Abramson et al.
U.S. Appl. No. 12/618,664, filed Nov. 13, 2009, Hariri.
U.S. Appl. No. 12/624,359, filed Nov. 23, 2009, Hariri.
U.S. Appl. No. 12/687,851, filed Jan. 14, 2010, Paludan et al.
Office Action dated Dec. 16, 2004 in U.S. Appl. No. 10/004,942, now US Patent No. 7,045,148.
Advisory Action dated Jul. 12, 2004 in U.S. Appl. No. 10/076,180.
Advisory Action dated Feb. 2, 2007 in U.S. Appl. No. 10/366,671, now US Patent No. 7,311,905.
Office Action dated Feb. 28, 2008 in U.S. Appl. No. 10/411,655, now US Patent No. 7,498,171.
Office Action dated Jul. 11, 2007 in U.S. Appl. No. 10/411,655, now US Patent No. 7,498,171.
Office Action dated May 18, 2006 in U.S. Appl. No. 10/411,655, now US Patent No. 7,498,171.
Office Action dated Nov. 20, 2006 in U.S. Appl. No. 10/411,655, now US Patent No. 7,498,171.
Advisory Action dated Oct. 25, 2007 in U.S. Appl. No. 10/449,248.
Office Action dated Apr. 26, 2007 in U.S. Appl. No. 10/449,248.
Office Action dated Aug. 29, 2006 in U.S. Appl. No. 10/449,248.
Office Action dated Feb. 7, 2008 in U.S. Appl. No. 10/449,248.
Advisory Action dated Feb. 6, 2006 in U.S. Appl. No. 10/721,144.
Office Action dated Jun. 12, 2006 in U.S. Appl. No. 10/874,828, now US Patent No. 7,468,276.
Non Final Action dated Feb. 19, 2010 in U.S. Appl. No. 11/088,149.
Advisory Action dated Oct. 22, 2009 in U.S. Appl. No. 11/088,149.
Final Rejection dated May 8, 2009 in U.S. Appl. No. 11/088,149.
Non Final Rejection dated Oct. 10, 2008 in U.S. Appl. No. 11/088,149.
Office Action dated Jan. 4, 2008 in U.S. Appl. No. 11/187,400.
Advisory Action dated Sep. 8, 2008 in U.S. Appl. No. 11/187,400.
U.S. Appl. No. 12/240,956, filed Sep. 28, 2008, Zhang et al.
U.S. Appl. No. 12/396,397, filed Mar. 2, 2009, Hariri et al.
Notice of Allowance, U.S. Appl. No. 10/874,828, now U.S. Patent No. 7,468,276, dated Oct. 14, 2008.
Notice of Allowance, U.S. Appl. No. 10/411,655, now U.S. Patent No. 7,498,171, dated Oct. 30, 2008.
Office Action dated Apr. 2, 2009 in U.S. Appl. No. 10/721,144.
Office Action dated Sep. 9, 2008 in U.S. Appl. No. 10/874,828.
Office Action dated Feb. 20, 2009 in U.S. Appl. No. 11/187,400.
Office Action dated May 22, 2008 in U.S. Appl. No. 11/187,400.
U.S. Appl. No. 11/982,211, filed Oct. 31, 2007, Heidaran et al.
U.S. Appl. No. 12/030,161, filed Feb. 12, 2008, Edinger et al.
U.S. Appl. No. 12/030,170, filed Feb. 12, 2008, Edinger et al.
Notice of Allowance in U.S. Appl. No. 10/004,942, now US Patent No. 7,045,148.
Office Action dated Dec. 16, 2004 in U.S. Appl. No. 10/004,942, now US Patent No. 7,045,148.
Office Action dated Dec. 5, 2003 in U.S. Appl. No. 10/004,942, now US Patent No. 7,045,148.
Office Action dated Jun. 15, 2004 in U.S. Appl. No. 10/004,942, now US Patent No. 7,045,148.
Office Action dated Jun. 20, 2005 in U.S. Appl. No. 10/004,942, now US Patent No. 7,045,148.
Office Action dated May 7, 2003 in U.S. Appl. No. 10/004,942, now US Patent No. 7,045,148.
Notice of Allowance in U.S. Appl. No. 10/074,976, now US Patent No. 7,311,904.
Office Action dated Jan. 5, 2006 in U.S. Appl. No. 10/074,976, now US Patent No. 7,311,904.
Office Action dated Mar. 27, 2007 in U.S. Appl. No. 10/074,976, now US Patent No. 7,311,904.
Office Action dated Sep. 20, 2006 in U.S. Appl. No. 10/074,976, now US Patent No. 7,311,904.
Office Action dated Sep. 23, 2004 in U.S. Appl. No. 10/074,976, now US Patent No. 7,311,904.
Office Action dated Aug. 28, 2003 in U.S. Appl. No. 10/076,180.
Office Action dated Jun. 20, 2005 in U.S. Appl. No. 10/076,180.
Office Action dated Mar. 18, 2004 in U.S. Appl. No. 10/076,180.
Office Action dated Oct. 20, 2004 in U.S. Appl. No. 10/076,180.
Notice of Allowance in U.S. Appl. No. 10/366,671, now US Patent No. 7,311,905.
Office Action dated Jan. 19, 2006 in U.S. Appl. No. 10/366,671, now US Patent No. 7,311,905.
Office Action dated May 14, 2007 in U.S. Appl. No. 10/366,671, now US Patent No. 7,311,905.
Office Action dated Oct. 10, 2006 in U.S. Appl. No. 10/366,671, now US Patent No. 7,311,905.
Notice of Allowance in U.S. Appl. No. 10/640,428, now US Patent No. 7,255,879.
Office Action dated Jan. 19, 2006 in U.S. Appl. No. 10/640,428, now US Patent No. 7,255,879.
Office Action dated Oct. 18, 2006 in U.S. Appl. No. 10/640,428, now US Patent No. 7,255,879.
Office Action dated Dec. 28, 2006 in U.S. Appl. No. 10/721,144.
Office Action dated Feb. 5, 2008 in U.S. Appl. No. 10/721,144.
Office Action dated Jan. 11, 2006 in U.S. Appl. No. 10/721,144.
Office Action dated Jun. 14, 2006 in U.S. Appl. No. 10/721,144.
Office Action dated Jun. 27, 2007 in U.S. Appl. No. 10/721,144.
Office Action dated Oct. 4, 2005 in U.S. Appl. No. 10/721,144.
Office Action dated Apr. 6, 2007 in U.S. Appl. No. 10/874,828.
Office Action dated Dec. 13, 2007 in U.S. Appl. No. 10/874,828.
Office Action dated Jun. 12, 2006 in U.S. Appl. No. 10/874,828.
Office Action dated Apr. 20, 2007 in U.S. Appl. No. 11/187,400.
Ashihara et al. "Successful Peripheral Blood Stem Cell Transplantation for Myelodysplastic Syndrome," *Bone Marrow Transplantation* (1999) 24(12): 1343-1345.
Beltrami et al., "Adult Cardiac Stem Cells Are Multipotent and Support Myocardial Regenerationl" 114:763-776 (2003).
Campagnoli et al., Blood (Oct. 15, 2001); 98(8):2396-402.
Caplan, "The Mesengenic Process," Clin Plast Surg (1994) 21(3):429-435.
Chao, et al., "Stem Cell Transplantation (Cord Blood Transplants)." *American Society of Hematology* (2004) p. 354-371.
Chen et al. "Intravaneous Administration of Human Umbilical Cord Reduces Behavioral Deficits after Stroke in Rats," *Stroke* (2001) 32(11): 2682-2688.
Chen, R. et al., "The Potential for the Use of Mononuclear Cells from Human Umbilical Cord Blood in the Treatment of Amyotrophic Lateral Sclerosis is SODI Mice," *J. Med.* (2000) 31(1-2):21-30.
Chin et al., "Enhanced Interferon Production and Lymphokine-Activated Cytotoxicity of Human Placental Cells," *Cellular Immunology* 113:1-9 (1988).
Clark David A et al, "Placental trophoblast from successful human pregnancies expresses the tolerance signaling molecule, CD200 (OX-2)" American Journal of Reproductive immunology, Munksgaard International Publishers, Copenhagen, DK, vol. 50, No. 3, Sep. 2003, pp. 187-195, XP002430047 ISSN: 1046-7408.
Cosma, et al., "Use and Application of Stem Cells in Toxicology." SOT 2003 Annual Meeting, p. 4, Abstract 19.
Czarneski, J. et al., "Effects of Cord Blood Transfer on the Hematopoietic Recovery Following Sublethal Irradiation in MRL Ipr/Ipr Mice," *Proc. Soc. Exp. Biol. Med.* (1999) 220(2):79-87.
Database WPI Week 200357 Derwent Publications Ltd., London, GB, AN 2003-59905 & CN 1 407 888 A (Zhou S) Apr. 2, 2003.
Davila, et al., "Use and Application of Stem Cells in Toxicology." Toxicological Sciences 79, 214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.

De Coppi, et al., "Human fetal stem cell isolation from amniotic fluid for tissue reconstruction," *J. Urology* 167(4 Supp.) 85 (Abstract 338) (2002).

De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.

Drake, P.M. et al., "Human Placental Cytotrophoblasts Attract Monocytes and CD56 (bright) Natural Killer Cells Via the Actions of Monocyte Inflammatory Protein Ialpha," *The Journal of Experimental Medicine* (2001) 193(10):1199-1212.

Ende, "Pooled umbilical cord blood as a possible universal donor for marrow reconstitution and use in nuclear accidents," *Life Sciences* (2001) 69;1531-1539.

Ende, N. et al., "Human Umbilical Cord Blood Cells Amerliorate Alzheimer's Disease in Transgenic Mice," *J. Med.* (2001) 32(3-4):241-7.

Ende, N. et al., "Human Umbilical Cord Blood Cells Ameliorate Huntington's Disease in Transgenic Mice," *J. Med.*, (2001) 32(3-4):231-40).

Ende, N. et al., "The Effect of Human Cord Blood on SJL/J Mice After Chemoablation and Irradiation and Its Possible Clinical Significance," *Immunol. Invest.* (1995) 24(6):999-1012.

Ende, N., et al., "Human Umbilical Cord Blood Effect on SOD Mice (Amyotrophic Lateral Sclerosis)," *Life Sci.* (2001) 67(1):53-9.

Ende, N., et al., "The Feasibility of Using Blood Bank-Stored (4 Degrees C) Cord Blood, Unmatched for HLA for Marrow Transplantation," *Am. J. Clin. Pathol.* (1999) 111(6):773-81.

Erices et al., "Mesenchymal progenitor cells in human umbilical cord blood," *Br. J. Haemotol.* 109(1):Abstract (2000).

Fasouliotis et al., "Human umbilical cord blood banking and transplantation: a state of the art," *Eur. J. Obstet. Gynecol. Reprod. Biol.* 90(1):13-25 (2000).

Forbes et al., *J. Pathol.* 197(4):510-518 (2002).

Gluckman et al., "Cord Blood Heamatopoietic Stem Cells: Biology and Transplantation," In: *Hematology, American Society of Hematology Education Program Book* (1998) p. 1-14.

Gluckman et al., "Results of Unrelated Umbilical Cord Blood Hematipoeietic Stem Cell Transplant," *Transfusion Cinique et Biologique* (2001) 8(3):146-154.

Harbacheuski, et al., "Placenta Derived Adherent Cells (PDACs) Supress Tumor Cells of Diverse Origin." Blood, vol. 108, No. 11, Part 2, Nov. 2006, p. 288b.

Hardingham et al., Cancer Research 53:3455-3458 (1993).

Himori, et al 1984, Chemotherapeutic susceptibility of human bone marrow progenitor cells and human myelogenous leukemia cells (HL-60) in co-culture: preliminary report. Int J Cell Cloning. 2(4):254-62.

Hung et al. "Mesenchymal Stem Cell Targeting of Microscopic Tumors and Tumor Stroma Development Monitored by Noninvasive in vivo Positron Emission tomography Imaging," *Clin. Cancer Res.* 11(21):7749-7756 (2005).

Huss, Stem Cells (2000) 18:1-9.

Igura, K., et al., "Isolation and Characterization of Mesencymal Progenitor Cells from Chorionic Villi of Human Placenta," *Cytotherapy* (2004) 6(6): 543-553.

International Search Report and Written Opinion from PCT/US2007/017622 dated Jun. 18, 2008.

Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.* 160(3):633-51 (1984).

Kurtzberg et al., 1996, Placental blood as a source of hematopoietic stem cells for transplantation into unrelated recipients. N Engl J Med. 335:157-166.

Lebkowski, Cancer J. (2001) Nov.-Dec. 7 Suppl 2:S83-93.

Leonard et al., "The Role of ABC Transporters in Clinical Practice," *Oncologist.* (2003) 8:411-424.

Li Chang Dong et al, "Mesenchymal stem cells derived from human placenta suppress allogeneic umbilical cord blood lymphocyte proliferation," Cell Research—Xibao Yanjiu Beijing, CN, vol. 15, No. 7, Jul. 2005, pp. 539-547, XP009080356 ISSN: 1001-0602.

McMaster, M. et al, "Human Placental HLA-G Expression is Restricted to Differentiated Cytotrophoblasts," *Journal of Immunology. The Williams and Wilkins Co.* (1995) 154(8): 3771-3778.

Miki, et al., "Isolation of Multipotent Stem Cells from Placenta." AASLD Abstracts, Hepatology, Oct. 2003, Abstract 279, p. 290A.

Miki, et al., "Production of Hepatocytes from Human Amniotic Stem Cells." Hepatology, Abstract 20, vol. 36, No. 4, Pt. 2, 2002.

Miki, et al., "Stem Cell Characteristics of Amniotic Epithelial Cells." Stem Cells Express, published online Aug. 9, 2005; doi:10. 1634/stemcells.2004-0357.

Minguell et al., "Mesenchymal Stem Cells," *Exp Biol Med* (2001) 226:507-520.

Moore et al., "A simple perfusion technique for isolation of matcrnal intervillous blood mononuclear cells from human placcntac," J. Immunol. Methods (1997) 209(1):93-104.

Mühlemann et al., "Cytomegalovirus in the Perfused Human Term Placenta in Vitro," *Placenta* (1995) 16:367-373.

Myllynen "In Search of Models for Hepatic and Placental Pharmacokinetics," [Dissertation] University of Oulu, 2003.

Nakamura K. et al. "Antitumor effect of genetically engineered mesenchymal stem cells in a rat glioma model." *Gene Therapy*(2004) vol. II, No. 14. pp. 1155-1164.

Paludan, et al., "Immune Suppression by Placenta Derived Adherent Cells (PDAC) Correlate with Monocyte Chemoattractant Protein-I and IL-2 Secretion." Blood 108: abstract only (2006).

Papaioannou et al., Stem Cells Handbook:19-31 (2004).

Pera et al., *j. Cell. Sci.* "Human Embryonic Stem Cells." (2000) 113:5-10.

Pittenger, M. F., et al. "Multilineage Potential of Adult Human Mcsenchymal Stem Cells." *Science* (1999) U.S. vol. 284, No. 5411, pp. 143-147.

Reyes et al., "Purification and Ex Vivo Expansion of Postnatal Human Marrow Mesodermanl Progenitor Cells," *Blood* (2001) 98(9):2615-2625.

Roth, I., et al. "Human Placental Cytotrophoblats Produce the Immunosuppressive Cytokine Interliukin 10," *The Journal of Experimental Medicine* (1996) 184(2): 539-548.

Sakuragawa et al., "Human amniotic epithelial cells arc promising transgene carriers for allogeneic cell transplantation into liver," *J. Hum. Genet.* 45:171-176 (2000).

ScienCell—Human Amniotic Epithelial Cells. http://www.sciencellonline.com/products/7100.htm.

Shamblott, et al., 1998, Derivation of pluripotent stem cells from cultured human primordial germ cells. Proc Natl Acad Sci U S A. 95(23):13726-31.

Studney et al., "Bone Marrow-derived Mesenchymal Stem Cells as Vehicles for Interferon-B Delivery into Tumors," Cancer Res. 62:3603-3608 (2002).

Wang et al., 2001, "Enhanced recovery of hematopoietic progenitor and stem cells from cultivated, postpartum human placenta," Blood 98(11/1):183a Abstract No. 769.

Woods et al., "Osomometric and permeability characteristics of human placental/umbilical cord blood CD34+ cells and their application to cryopreservation," *J. Hematother. Stem Cell Res.* 9(2):161-173 (2000).

Ye et al., 2001, "Recovery of placental-derived adherent cells with mesenchymal stem cell characteristics," Blood 98(11/1):147b Abstract No. 4260.

Yen B. Linju et al, "Isolation of multipotent cells from human term placenta" Stem Cells (Dayton, Ohio) 2005, vol. 23, No. 1, Jan. 2005, pp. 3-9, XP002443187 ISSN: 1065-5099.

Zhang Yi et al. "Human placenta-derived mesenchymal progenitor cells support culture expansion of long-term culture-initiating cells from cord blood CD34+ Cell" Experimental Hematology, New, NY, US, vol. 32, No. 7, Jul. 2004, pp. 657-664, XP002389863 ISSN: 0301-472X.

Zhu et al., "Mesenchymal Stem Cells Derived from Bone Marrow Favor Tumor Cell Growth in Vivo." *Exp. Mol. Pathol.* (epublication prior to publication, 2005).

U.S. Appl. No. 12/829,326, filed Jul. 1, 2010, Abbot.

Abe, "Therapeutic Potential of Neurotrophic Factors and Neural Stem Cells Against Ischemic Brain Injury," Journal of Cerebral Blood Flow and Metabolism, Raven Press, Ltd., New York, 20(10): 1393-1408 (2000).

Chen et al. "Intravenous administration of human umbilical cord blood reduces behavioral deficits after stroke in rats" Stroke 32:2682-2688 (2001).

Conget et al. "Phenotypical and functional properties of human bone marrow mesenchymal progenitor cells" Journal of Cellular Physiology 181:67-73 (1999).

Denison et al. "Cytokine secretion by human fetal membranes, decidua and placenta at term" Human Reproduction 13(12):3560-3565 (1998).

Fassas, et al., "Autologous Stem Cell Transplantation in Progressive Multiple Sclerosis—an Interim Analysis of Efficacy," J. Clin. Immunol., 20(1):24-30 (2000).

Hsieh et al. "Effects of glucose on placental hormones in the human term placenta in vitro" J. Formos. Med. Assoc. 96:309-313 (1997).

Jaroscak et al. "Preliminary characterization of the surface staining of placental derived adherent cells: a potential new source of stroma for umbilical cord blood (UCB) expansion," Blood 96(11, Pt 2) (2000).

Malek et al. "Lack of transport of erythropoietin across the human placenta as studied by an in vitro perfusion system," European Journal of Physiology 427:157-161 (1994).

Marmont, "New Horizons in the Treatment of Autoimmune Diseases: Immunoablation and Stem Cell Transplantation," Ann. Rev. Medicine 51:115-134 (2000).

Parolini et al. "Concise review: Isolation and characterization of cells from human term placenta: Outcome of the first international workshop on placenta derived stem cells" Stem Cells 26:300-311 (2008).

Ponticiello et al. "Gelatin-based resorbable sponge as a carrier matrix for human mesenchymal stem cells in cartilage regeneration therapy" Journal of Biomedical Materials Research 52:246-255 (2000).

Reubinoff, "Neural Progenitors from Human Embryonic Stem Cells," Nature Biotech. 19(12):1134-1140 (2001).

Semenov et al. "Multipotent mesenchymal stem cells from human placenta: critical parameters for isolation and maintenance of stemness after isolation" American Journal of Obstetrics & Gynecolocy 202:193.e1-13 (2010).

Xu et al. "Feeder-free growth of undifferentiated human embryonic stem cells" Nature Biotechnology 19:971-974 (2001).

Yen et al. "Isolation of multipotent cells from human term placenta" Stem Cells 23:3-9 (2005).

Yin et al "AC133, a novel marker for human hematopoietic stem and progenitor cells" Blood 90(12):5002-5012 (1997).

Zhao, et al., "Transplanted Human Bone Marrow-Derived Adult Stem Cells Survive and Improve Functional Outcome in a Rat Model of Cortical Ischemic Brain Injury," Experimental Neurology, Academic Press, New York, 164(2):465-466, XP001159669 (2000).

Zhao, et al., "Human Bone Marrow Stem Cells Exhibit Neural Phenotypes After Transplantation and Ameliorate Neurological Deficits with Ischemic Brain Injury in Rats," Abstract of the Annual Meeting of the Society for Neuroscience, Society of Neuroscience, Washington, DC, 26(1/02):860.01, XP001159670 (2000).

Extended European Search Report dated Mar. 25, 2011 for EP Application No. 10182195.7-2401 (specification corresponding to U.S. Patent No. 7,468,276).

Extended European Search Report dated Mar. 25, 2011 for EP Application No. 10182243.5-2401 (specification corresponding to U.S. Patent No. 7,468,276).

Extended European Search Report dated Mar. 30, 2011 for EP Application No. 10182303.7-2401 (specification corresponding to U.S. Patent No. 7,468,276).

Extended European Search Report dated Mar. 25, 2011 for EP Application No. 10182362.3-2401 (specification corresponding to U.S. Patent No. 7,468,276).

Extended European Search Report dated Mar. 28, 2011 for EP Application No. 10182433.2-2401 (specification corresponding to U.S. Patent No. 7,468,276).

Extended European Search Report dated Mar. 25, 2011 for EP Application No. 10182485.2-2401 (specification corresponding to U.S. Patent No. 7,468,276).

Extended European Search Report dated Mar. 11, 2011 for EP Application No. 10183435.6-2401 (specification corresponding to U.S. Patent No. 7,045,148).

Extended European Search Report dated Mar. 3, 2011 for EP Application No. 10183378.8-2401 (specification corresponding to U.S. Patent No. 7,045,148).

Extended European Search Report dated Mar. 22, 2011 for EP Application No. 10183252.5-2401 (specification corresponding to U.S. Patent No. 7,311,904).

Extended European Search Report dated Mar. 25, 2011 for EP Application No. 10183301.0-2401 (specification corresponding to U.S. Patent No. 7,311,904).

* cited by examiner

TUMOR SUPPRESSION USING PLACENTAL STEM CELLS

1. FIELD OF THE INVENTION

The present invention provides methods of using placental stem cells to suppress the proliferation of tumor cells, and the growth of tumors. The invention also provides compounds comprising placental stem cells for use in suppression of tumor cell proliferation and tumor growth, isolated populations of tumor-suppressive populations of placental stem cells, and methods of making such populations.

2. BACKGROUND OF THE INVENTION

Human stem cells are totipotential or pluripotential precursor cells capable of generating a variety of mature human cell lineages. Evidence exists that demonstrates that stem cells can be employed to repopulate many, if not all, tissues and restore physiologic and anatomic functionality.

Many different types of mammalian stem cells have been characterized. See, e.g., Caplan et al., U.S. Pat. No. 5,486,359 (human mesenchymal stem cells); Boyse et al., U.S. Pat. No. 5,004,681 (fetal and neonatal hematopoietic stem and progenitor cells); Boyse et al., U.S. Pat. No. 5,192,553 (same); Beltrami et al., *Cell* 114(6):763-766 (2003) (cardiac stem cells); Forbes et al., *J. Pathol.* 197(4):510-518 (2002) (hepatic stem cells). Umbilical cord blood, and total nucleated cells derived from cord blood, have been used in transplants to restore, partially or fully, hematopoietic function in patients who have undergone ablative therapy.

The placenta is a particularly attractive source of stem cells. Because mammalian placentas are plentiful and are normally discarded as medical waste, they represent a unique source of medically-useful stem cells.

Bone marrow-derived mesenchymal stem cells have recently been shown, when genetically modified, to have the ability to migrate into, and infiltrate, certain tumor cells. See, e.g., Hung et al., "Mesenchymal Stem Cell Targeting of Microscopic Tumors and Tumor Stroma Development Monitored by Noninvasive In vivo Positron Emission tomography Imaging," *Clin. Cancer Res.* 11(21):7749-7756 (2005). Certain genetically engineered bone marrow-derived mesenchymal stem cell lines have been shown to suppress tumor growth. See, e.g., Studney et al., "Bone Marrow-derived Mesenchymal Stem Cells as Vehicles for Interferon-β Delivery into Tumors," *Cancer Res.* 62:3603-3608 (2002) (melanoma cell line); Nakamura et al., "Antitumor Effect of Genetically Engineered Mesenchymal Stem Cells in a Rat Glioma Model," *Gene Therapy* 11:1155-1164 (2004 (mesenchymal stem cells expressed recombinant IL-2). Mesenchymal stem cells, however, have been shown to promote the growth of at least one kind of tumor in vivo. See Zhu et al., "Mesenchymal Stem Cells Derived from Bone Marrow Favor Tumor Cell Growth In Vivo," *Exp. Mol. Pathol.* (epublication prior to publication, 2005) (colon adenocarcinoma cells).

To date, however, no one has described the ability of placenta-derived stem cells to suppress the growth of tumors, or to suppress the proliferation of tumor cells. The present invention provides such a use for placental stem cells and populations of the same.

3. SUMMARY OF THE INVENTION

The present invention provides methods of suppression of tumor cell proliferation, and of tumor growth, using placental stem cells, populations of placental stem cells, and compositions comprising placental stem cells. The present invention also provides compositions, including compositions comprising placental stem cells, having tumor cell proliferation suppressive properties. The invention further provides populations of placental cells selected on the basis of their ability to suppress tumor cell proliferation, and compositions having such properties.

In one aspect, the invention provides a method of suppressing proliferation of a plurality of tumor cells comprising contacting said plurality of tumor cells with a plurality of placental stem cells for a time sufficient for said placental stem cells to detectably suppress proliferation of said plurality of tumor cells, as compared to a plurality of tumor cells not contacted with placental stem cells. In a specific embodiment, said tumor cells are part of a solid tumor. In another specific embodiment, said tumor cells are a non-solid tumor cell type. In another specific embodiment, said tumor cells are histiocytic lymphoma cells, chronic myelogenous leukemia cells, acute T-cell leukemia, acute myelogenous leukemia, colon adenocarcinoma cells, retinoblastoma cells or lung carcinoma cells. In another specific embodiment of the method, said contacting is performed in vitro. In another specific embodiment, said contacting is performed in an individual in vivo. The individual can be a mammal, e.g., a human. In another specific embodiment, said placental stem cells are HLA matched to said individual. In another specific embodiment, said placental stem cells are not HLA matched to said individual. In another more specific embodiment, said contacting comprises administering said placental cells to said individual intravenously. In another more specific embodiment, said contacting comprises administering said placental cells to said individual at or adjacent to the site of a tumor. In specific embodiments, said placental stem cells: express CD200 and HLA-G; express CD73, CD105, and CD200; express CD200 and OCT-4; express CD73, CD105, and HLA-G; express CD73 and CD105, and facilitate the formation of one or more embryoid-like bodies in a population of placental cells that comprise the stem cell, when said population is cultured under conditions that allow formation of embryoid-like bodies; and/or express OCT-4 and facilitate the formation of one or more embryoid-like bodies in a population of placental cells that comprise the stem cell, when said population is cultured under conditions that allow formation of embryoid-like bodies.

In another specific embodiment, at least a portion of said plurality of placental stem cells have been engineered to express a cytokine. In a more specific embodiment, said cytokine is IFN-β or IL-2.

In another specific embodiment, the method additionally comprises contacting said tumor cells with one or more anti-cancer compounds. In another specific embodiment, the method additionally comprises contacting said tumor cells with a plurality of mesenchymal stem cells, e.g., bone marrow-derived mesenchymal stem cells. In another specific embodiment, the method additionally comprises contacting said tumor cells with a plurality of fibroblast cells.

In another specific embodiment, the method additionally comprises contacting said tumor cells with one or more stem cell chemoattractants. In a more specific embodiment, said chemoattractant is stromal derived factor-1 (SDF-1).

The method can employ as many placental stem cells as are required to effect a detectable suppression of tumor cell proliferation or growth of a tumor, e.g. in an individual. For example, the plurality of placental stem cells used to contact the plurality of tumor cells can comprise about $1\times10^5$ placental stem cells, about $1\times10^6$ placental stem cells, about $1\times10^7$ placental stem cells, or about $1\times10^8$ placental stem cells, or more. In various more specific embodiments, the method comprises administering at least about $1\times10^5$, at least about $1\times10^6$, at least about $1\times10^7$, or at least about $1\times10^8$ placental stem cells to said individual. In various more specific embodiments, the method comprises administering a number of placental stem cells about one time, two times, three times, four times, five times, or more than five times the number of tumor cells in an individual. Any art known method may be used to determine the number of tumor cells in an individual. Exemplary methods of tumor cell quantification are described in U.S. Pat. Nos. 6,365,362 and 6,645,731; by Méhes et al., *Haematologia* 31(2):97-109 (2001); and Hardingham et al., *Cancer Research* 53:3455-3458 (1993), the contents of which are hereby incorporated by reference in their entireties. In various more specific embodiments, the method comprises administering a number of placental stem cells based on the weight of the individual. For example, the method comprises administering about $1\times10^3$ placental stem cells/kg, $5\times10^3$ placental stem cells/kg, $1\times10^4$ placental stem cells/kg, $5\times10^4$ placental stem cells/kg, $1\times10^5$ placental stem cells/kg, $5\times10^5$ placental stem cells/kg, $1\times10^6$ placental stem cells/kg, $5\times10^6$ placental stem cells/kg, $1\times10^7$ placental stem cells/kg, $5\times10^7$ placental stem cells/kg, or $1\times10^8$ placental stem cells/kg to said individual. In various more specific embodiments, the method comprises administering at least about $1\times10^3$ placental stem cells/kg, at least about $5\times10^3$ placental stem cells/kg, at least about $1\times10^4$ placental stem cells/kg, at least about $5\times10^4$ placental stem cells/kg, at least about $1\times10^5$ placental stem cells/kg, at least about $5\times10^5$ placental stem cells/kg, at least about $1\times10^6$ placental stem cells/kg, at least about $5\times10^6$ placental stem cells/kg, at least about $1\times10^7$ placental stem cells/kg, at least about $5\times10^7$ placental stem cells/kg, or at least about $1\times10^8$ placental stem cells/kg to said individual.

In various other more specific embodiments, said placental stem cells have been proliferated in vitro for no more than 30 population doublings, no more than 20 population doublings, no more than 10 population doublings, or no more than 5 population doublings. In another specific embodiment, said placental stem cells have been cryopreserved and thawed prior to said contacting. In more specific embodiments of the method, said placental stem cells are confirmed to suppress tumor cell proliferation in vitro by, e.g., at least about 20%, 30%, 40%, 50%, 60%, 70%, 75%, 80%, 90%, or 95%, compared to proliferation of an equivalent number of tumor cells in the absence of said placental stem cells.

In another specific embodiment, the method additionally comprises determining that said placental stem cells have tumor cell growth suppressive activity prior to administration of said placental stem cells to said individual, e.g., screening said placental stem cells for detectable suppression of proliferation of representative sample tumor cells. In more specific embodiments of the method, said placental stem cells are confirmed to suppress tumor cell proliferation in vitro by, e.g., at least about 20%, 30%, 40%, 50%, 60%, 70%, 75%, 80%, 90%, or 95%, compared to proliferation of an equivalent number of tumor cells in the absence of said placental stem cells, prior to administration to said individual. In certain embodiments, the placental stem cells, prior to administration to an individual comprising tumor cells, is determined to suppress the proliferation of tumor cells by direct contact, by non-direct contact (e.g., through soluble factors), or both. For example, in specific embodiments of the method, said placental stem cells are determined to suppress tumor cell proliferation in vitro by, e.g., at least about 20%, 30%, 40%, 50%, 60%, 70%, 75%, 80%, 90%, or 95% in a direct culture assay, in, e.g., a transwell assay, or more preferably, in both a direct culture assay and a transwell assay, prior to administration to said individual. In another specific embodiment, said placental stem cells are screened in vitro for suppression of proliferation of tumor cells, or tumor growth, against a tumor cell sharing the same cell type, e.g. epithelial, squamous, etc., the same tissue of origin, e.g. breast, prostate, etc., or more preferably, both the same cell type and tissue of origin as a tumor cell that is endogenous to the individual to be administered said placental stem cells according to the method. In another more specific embodiment, said placental stem cells are screened in vitro for tumor growth suppressive activity against tumor cells obtained from a biopsy of said individual, or purified or isolated from a blood sample of said individual. In various more specific embodiments of the method, said placental stem cells can be derived from amnion, chorion, amnion-chorion, umbilical cord or perfusate, and are confirmed to suppress tumor cell proliferation in vitro by, e.g., at least about 20%, 30%, 40%, 50%, 60%, 70%, 75%, 80%, 90%, or 95%, compared to proliferation of an equivalent number of tumor cells in the absence of said placental stem cells, prior to administration to said individual.

The invention further provides a method of suppressing growth or proliferation of a plurality of tumor cells, e.g., blood cancer cells, comprising contacting said plurality of tumor cells with a composition comprising conditioned culture medium or a supernatant from a culture of a plurality of placental stem cells for a time sufficient for said conditioned culture medium or supernatant to detectably suppress proliferation of said plurality of tumor cells, as compared to a plurality of tumor cells not contacted with said conditioned culture medium or supernatant. In a specific embodiment, said contacting is performed in vitro. In another specific embodiment, said contacting is performed in vivo. In another specific embodiment, said conditioned culture medium or supernatant is obtained from a plurality of placental stem cells that are co-cultured with a plurality of tumor cells.

In various specific embodiments, said conditioned culture medium or supernatant is obtained from a plurality of placental stem cells co-cultured with a plurality of tumor cells at a ratio of about 1:1, about 2:1, about 3:1, about 4:1, or about 5:1 placental stem cells to tumor cells. The method can employ conditioned culture medium or supernatant from as many placental stem cells, alone or co-cultured with a plurality of tumor cells, as are required to effect a detectable suppression of tumor cell proliferation or growth of a tumor. For example, the conditioned culture medium or supernatant can be obtained from a culture comprising about $1\times10^5$ placental stem cells, about $1\times10^6$ placental stem cells, about $1\times10^7$ placental stem cells, or about $1\times10^8$ placental stem cells, or more. In another specific embodiment, the conditioned culture medium or supernatant can be obtained from a co-culture comprising about $1\times10^5$ to about $5\times10^5$ placental stem cells and about $1\times10^5$ tumor cells; about $1\times10^6$ to about $5\times10^6$ placental stem cells and about $1\times10^6$ tumor cells; about $1\times10^7$ to about $5\times10^7$ placental stem cells and about $1\times10^7$ tumor cells; or about $1\times10^8$ to about $5\times10^8$ placental stem cells and about $1\times10^8$ tumor cells.

In another specific embodiment of the method of suppressing the growth or proliferation of tumor cells, the conditioned culture medium or supernatant is culture medium or supernatant from a culture comprising a number of placental stem cells, alone or co-cultured with tumor cells, wherein the number of cells producing the conditioned medium is based on the weight of an individual to which the conditioned medium is administered. For example, the conditioned culture medium or supernatant can be conditioned medium or supernatant produced by a culture comprising about $1\times10^3$ placental stem cells per kg of a recipient's body weight, $5\times10^3$ placental stem cells/kg, $1\times10^4$ placental stem cells/kg, $5\times10^4$ placental stem cells/kg, $1\times10^5$ placental stem cells/kg, $5\times10^5$ placental stem cells/kg, $1\times10^6$ placental stem cells/kg, $5\times10^6$ placental stem cells/kg, $1\times10^7$ placental stem cells/kg, $5\times10^7$ placental stem cells/kg, or $1\times10^8$ placental stem cells/kg. In another specific embodiment, the conditioned culture medium or supernatant is culture medium or supernatant from a co-culture comprising about $1\times10^3$ to about $5\times10^3$ placental stem cells/kg and about $1\times10^3$ tumor cells/kg; about $1\times10^4$ to about $5\times10^4$ placental stem cells/kg and about $1\times10^4$ tumor cells/kg; about $1\times10^5$ to about $5\times10^5$ placental stem cells/kg and about $1\times10^5$ tumor cells/kg; about $1\times10^6$ to about $5\times10^6$ placental stem cells/kg and about $1\times10^6$ tumor cells/kg; about $1\times10^7$ to about $5\times10^7$ placental stem cells/kg and about $1\times10^7$ tumor cells/kg; or about $1\times10^8$ to about $5\times10^8$ placental stem cells/kg and about $1\times10^8$ tumor cells/kg.

The invention further provides methods of producing cell populations comprising placental stem cells selected on the basis of their ability to suppress the proliferation of a tumor cell or population of tumor cells, or the growth of a tumor. In one embodiment, for example, the invention provides a method of producing a cell population comprising selecting placental stem cells, wherein said placental stem cells (a) adhere to a substrate; (b) express CD200 and HLA-G; or express CD73, CD105, and CD200; or express CD200 and OCT-4; or express CD73, CD105, and HLA-G; or express CD73 and CD105, and facilitate the formation of one or more embryoid-like bodies in a population of placental cells that comprise the placental stem cells, when said population is cultured under conditions that allow formation of embryoid-like bodies; or express OCT-4, and facilitate the formation of one or more embryoid-like bodies in a population of placental cells that comprise the placental stem cells, when said population is cultured under conditions that allow formation of embryoid-like bodies; and (c) detectably suppress the proliferation of a tumor cell or plurality of tumor cells, or growth of a tumor; and isolating said placental stem cells from other cells to form a cell population.

In another embodiment, the invention provides a method of producing an isolated cell population comprising selecting placental stem cells that (a) adhere to a substrate, (b) express CD200 and HLA-G, and (c) detectably suppress tumor cell proliferation, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells; and isolating said placental stem cells from other cells to form a cell population. In another embodiment, the method comprises selecting placental stem cells that (a) adhere to a substrate, (b) express CD73, CD105, and CD200, and (c) detectably suppress tumor cell proliferation, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells; and isolating said placental stem cells from other cells to form a cell population. In another embodiment, the method comprises selecting placental stem cells that (a) adhere to a substrate, (b) express CD200 and OCT-4, and (c) detectably suppress tumor cell proliferation, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells; and isolating said placental stem cells from other cells to form a cell population. In another embodiment, the method comprises selecting placental stem cells that (a) adhere to a substrate, (b) express CD73 and CD105, (c) form embryoid-like bodies when cultured under conditions allowing the formation of embryoid-like bodies, and (d) detectably suppress tumor cell proliferation, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells; and isolating said placental stem cells from other cells to form a cell population. In another embodiment, the method comprises selecting placental stem cells that (a) adhere to a substrate, (b) express CD73, CD105, and HLA-G, and (c) detectably suppress tumor cell proliferation, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells; and isolating said placental stem cells from other cells to form a cell population. In another embodiment, the method comprises selecting placental stem cells that (a) adhere to a substrate, (b) express OCT-4, (c) form embryoid-like bodies when cultured under conditions allowing the formation of embryoid-like bodies, and (d) detectably suppress tumor cell proliferation, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells; and isolating said placental stem cells from other cells to form a cell population. In a more specific embodiment of the above methods, said placental stem cells are derived primarily from amnion, chorion, amnion and chorion, or umbilical cord. In another more specific embodiment, the stem cells used in the methods are umbilical cord stem cells.

In the above methods of producing isolated populations of placental stem cells, in one embodiment, the methods can comprise selecting cells exhibiting at least one characteristic specific to a mesenchymal stem cell. In a more specific embodiment, said characteristic specific to a mesenchymal stem cell is expression of CD29, expression of CD44, expression of CD90, or expression of a combination of the foregoing. In another specific embodiment of the methods, said selecting is accomplished using an antibody. In another specific embodiment, said selecting is accomplished using flow cytometry. In another specific embodiment, said selecting is accomplished using magnetic beads. In another specific embodiment, said selecting is accomplished by fluorescence-activated cell sorting. In another specific embodiment of the above methods, said cell population is expanded.

The invention also provides isolated populations of placental stem cells produced or selected, e.g., according to any of the above methods. In one embodiment, for example, the invention provides an isolated cell population comprising placental stem cells, wherein said placental stem cells: (a) adhere to a substrate; (b) express CD200 and HLA-G, or express CD73, CD105, and CD200, or express CD200 and OCT-4, or express CD73, CD105, and HLA-G, or express CD73 and CD105, and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells, when said population is cultured under conditions that allow formation of embryoid-like bodies; and (c) have been determined to detectably suppress proliferation of a plurality of tumor cells, as compared to a plurality of tumor cells not contacted with placental stem cells.

In a specific embodiment, the isolated placental cell population comprises placental stem cells that (a) adhere to a substrate, (b) express CD200 and HLA-G, and (c) have been determined to detectably suppress proliferation of said plurality of tumor cells, as compared to a plurality of tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells. In another specific embodiment, the isolated placental cell population comprises placental stem cells that (a) adhere to a substrate, (b) express CD73, CD105, and CD200, and (c) have been determined to detectably suppress proliferation of said plurality of tumor cells, as compared to a plurality of tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells. In another specific embodiment, the isolated placental cell population comprises placental stem cells that (a) adhere to a substrate, (b) express CD200 and OCT-4, and (c) have been determined to detectably suppress proliferation of said plurality of tumor cells, as compared to a plurality of tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells.

In another specific embodiment, the isolated placental cell population comprises placental stem cells that (a) adhere to a substrate, (b) express CD73 and CD105, (c) form embryoid-like bodies when cultured under conditions allowing the formation of embryoid-like bodies, and (d) have been determined to detectably suppress proliferation of said plurality of tumor cells, as compared to a plurality of tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells. In another specific embodiment, the isolated placental cell population comprises placental stem cells that (a) adhere to a substrate, (b) express CD73, CD105, and HLA-G, and (c) have been determined to detectably suppress proliferation of said plurality of tumor cells, as compared to a plurality of tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells. In yet another specific embodiment, the isolated placental stem cell population comprises placental stem cells that (a) adhere to a substrate, (b) express OCT-4, (c) form embryoid-like bodies when cultured under conditions allowing the formation of embryoid-like bodies, and (d) have been determined to detectably suppress proliferation of said plurality of tumor cells, as compared to a plurality of tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells.

The invention also provides compositions comprising any of the isolated placental stem cell populations described above. In a specific embodiment, the composition also comprises a plurality of non-placental cells, e.g., non-placental stem cells, e.g. mesenchymal stem cells, e.g., bone marrow-derived mesenchymal stem cells. In a specific embodiment, the composition also comprises a plurality of fibroblasts. In some embodiments, the fibroblasts are autologous to the subject being administered a placental stem cell composition described herein.

In the above methods, isolated placental stem cell populations and compositions, the placental stem tells may be defined by or selected on the basis of additional markers. For example, said placental stem cells that express CD200 and HLA-G also express CD73 and CD105, that is, are $CD73^+$ and $CD105^+$. In another specific embodiment, said placental cells are $CD34^-$, $CD38^-$ or $CD45^-$. In a more specific embodiment, said placental stem cells are $CD34^-$, $CD38^-$, $CD45^-$, $CD73^+$ and $CD105^+$. In another specific embodiment, said plurality of placental stem cells facilitates the development of one or more embryoid-like bodies from a population of isolated placental cells comprising the placental stem cells when said population is cultured under conditions that allow formation of embryoid-like bodies.

In another more specific embodiment, said placental stem cells that express CD73, CD105, and CD200 are also HLA-$G^+$. In another specific embodiment, said placental stem cells are $CD34^-$, $CD38^-$ or $CD45^-$. In another specific embodiment, said placental stem cells are $CD34^-$, $CD38^-$ and $CD45^-$. In a more specific embodiment, said placental stem cells are $CD34^-$, $CD38^-$, $CD45^-$, and HLA-$G^+$. In another specific embodiment, said placental stem cells facilitate the development of one or more embryoid-like bodies from a population of isolated placental cells comprising the placental stem cells when said population is cultured under conditions that allow formation of embryoid-like bodies.

In another more specific embodiment, said placental stem cells that express CD200 and OCT-4 also express $CD73^+$ and $CD105^+$. In another specific embodiment, said placental stem cells are HLA-$G^+$. In another specific embodiment, said placental stem cells are $CD34^-$, $CD38^-$ or $CD45^-$. In another specific embodiment, said placental stem cells are $CD34^-$, $CD38^-$ and $CD45^-$. In a more specific embodiment, said placental stem cells are $CD34^-$, $CD38^-$, $CD45^-$, $CD73^+$, $CD105^+$ and HLA-$G^+$. In another specific embodiment, said placental stem cells facilitate the formation of one or more embryoid-like bodies from a population of isolated placental cells comprising placental stem cells when said population is cultured under conditions that allow formation of embryoid-like bodies.

In another more specific embodiment, said placental stem cells that express CD73, CD105, and HLA-G are also $CD34^-$, $CD38^-$ or $CD45^-$. In another specific embodiment, said placental stem cells are $CD34^-$, $CD38^-$ and $CD45^-$. In another specific embodiment, said placental stem cells are OCT-$4^+$. In another specific embodiment, said placental stem cells are $CD200^+$. In a more specific embodiment, said placental stem cells are $CD34^-$, $CD38^-$, $CD45^-$, OCT-$4^+$ and $CD200^+$. In another specific embodiment, said stem cells facilitate the formation of one or more embryoid-like bodies from a population of isolated placental cells comprising the placental stem cells when said population is cultured under conditions that allow formation of embryoid-like bodies.

In another more specific embodiment, said placental stem cells that express CD73 and CD105, and facilitate the formation of one or more embryoid-like bodies in a population of placental cells that comprise the placental stem cells when said population is cultured under conditions that allow formation of embryoid-like bodies, are also $CD34^-$, $CD38^-$ or $CD45^-$. In another specific embodiment, said placental stem cells are OCT-$4^+$. In another specific embodiment, said placental stem cells are CD200$^+$. In another specific embodiment, said placental stem cells are OCT-4$^+$, CD200$^+$, CD34$^-$, CD38$^-$ and CD45$^-$.

In another more specific embodiment, said placental stem cells that express OCT-4, and facilitate the formation of one or more embryoid-like bodies in a population of placental cells that comprise the placental stem cells when said population is cultured under conditions that allow formation of embryoid-like bodies, are also CD73$^+$ and CD105$^+$. In another specific embodiment, said placental stem cells are CD34$^-$, CD38$^-$ and CD45$^-$. In another specific embodiment, said placental stem cells are CD200$^+$. In another specific embodiment, said placental stem cells are CD73$^+$, CD105$^+$, CD200$^+$, CD34$^-$, CD38$^-$ and CD45$^-$.

Placental stem cells used in the methods, isolated populations and compositions herein can be derived from the whole placenta, or from any part of the placenta. For example, in various embodiments, said placental stem cells are derived primarily, or only, from amnion, or amnion and chorion. In another embodiment, stem cells used in the methods of the invention are obtained from umbilical cord.

The invention further provides isolated cell populations comprising placental stem cells produced by any of the methods described herein for selecting tumor cell suppressive placental cell populations. For example, in one embodiment, the invention provides a cell population comprising isolated placental stem cell, wherein said placental stem cells: (a) adhere to a substrate; (b) express CD200 and HLA-G, or express CD73, CD105, and CD200, or express CD200 and OCT-4, or express CD73, CD105, and HLA-G, or express CD73 and CD105, and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells, when said population is cultured under conditions that allow formation of embryoid-like bodies; and (c) detectably suppress the proliferation of a tumor cell or plurality of tumor cells, or growth of a tumor.

The invention further provides cryopreserved stem cell populations, e.g., a cell population comprising placental stem cells, wherein the cell population is tumor cell suppressive, that are described herein. For example, the invention provides a population of CD200$^+$, HLA-G$^+$ placental stem cells that detectably suppress proliferation of said plurality of tumor cells, as compared to a plurality of tumor cells not contacted with placental stem cells, wherein said cells have been cryopreserved, and wherein said population is contained within a container. The invention also provides a population of CD73$^+$, CD105$^+$, CD200$^+$ placental stem cells that detectably suppress proliferation of said plurality of tumor cells, as compared to a plurality of tumor cells not contacted with placental stem cells, wherein said stem cells have been cryopreserved, and wherein said population is contained within a container. The invention also provides a population of CD200$^+$, OCT-4$^+$ placental stem cells that detectably suppress proliferation of said plurality of tumor cells, as compared to a plurality of tumor cells not contacted with placental stem cells, wherein said stem cells have been cryopreserved, and wherein said population is contained within a container. The invention also provides a population of CD73$^+$, CD105$^+$ placental stem cells that detectably suppress proliferation of said plurality of tumor cells, as compared to a plurality of tumor cells not contacted with placental stem cells, wherein said cells have been cryopreserved, and wherein said population is contained within a container, and wherein said stem cells facilitate the formation of one or more embryoid-like bodies when cultured with a population of placental cells under conditions that allow for the formation of embryoid-like bodies. The invention further provides a population of CD73$^+$, CD105$^+$, HLA-G$^+$ placental stem cells that detectably suppress proliferation of said plurality of tumor cells, as compared to a plurality of tumor cells not contacted with placental stem cells, wherein said cells have been cryopreserved, and wherein said population is contained within a container. The invention also provides a population of OCT-4$^+$ placental stem cells that detectably suppress proliferation of said plurality of tumor cells, as compared to a plurality of tumor cells not contacted with placental stem cells, wherein said cells have been cryopreserved, wherein said population is contained within a container, and wherein said stem cells facilitate the formation of one or more embryoid-like bodies when cultured with a population of placental cells under conditions that allow for the formation of embryoid-like bodies.

In a specific embodiment of any of the foregoing cryopreserved populations, said container is a bag. In various specific embodiments, said population comprises about, at least, or at most $1\times10^6$ said stem cells, $5\times10^6$ said stem cells, $1\times10^7$ said stem cells, $5\times10^7$ said stem cells, $1\times10^8$ said stem cells, $5\times10^8$ said stem cells, $1\times10^9$ said stem cells, $5\times10^9$ said stem cells, or $1\times10^{10}$ said stem cells. In other specific embodiments of any of the foregoing cryopreserved populations, said stem cells have been passaged about, at least, or no more than 5 times, no more than 10 times, no more than 15 times, or no more than 20 times. In another specific embodiment of any of the foregoing cryopreserved populations, said stem cells have been expanded within said container.

The invention further provides tumor cell suppressive compositions, that is, compositions that detectably suppress the proliferation of a tumor cell or population of tumor cells, or suppress the growth of a tumor. In one embodiment, the invention provides a composition comprising supernatant from a culture of any of the isolated placental cell populations described herein. In another embodiment, the invention provides a composition comprising culture medium from a culture of isolated placental stem cells, wherein said placental cells (a) adhere to a substrate; (b) express CD200 and HLA-G, or express CD73, CD105, and CD200, or express CD200 and OCT-4, or express CD73, CD105, and HLA-G, or express CD73 and CD105, and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells, when said population is cultured under conditions that allow formation of embryoid-like bodies; and (c) detectably suppress the proliferation of a tumor cell or population of tumor cells, or the growth of a tumor, wherein said culture of placental stem cells have been cultured in said medium for 24 hours or more.

In another specific embodiment, any of the foregoing compositions comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons.

The present invention also provides pharmaceutical compositions comprising placental stem cells that have been genetically engineered to produce recombinant or exogenous cytokines associated with tumor suppression. For example, in one embodiment, the invention provides a pharmaceutical compound comprising a plurality of placental stem cells, wherein said placental stem cells have been engineered to express exogenous IFN-β or IL-2. In a specific embodiment, said placental stem cells express exogenous IFN-β or IL-2 in an amount that results in detectably greater suppression of tumor cell proliferation, when said tumor cells are contacted with said placental stem cells, compared to placental stem cells not expressing exogenous IFN-β or IL-2. In more specific embodiments, said placental stem cells (a) adhere to a substrate, (b) express CD200 and HLA-G, or express CD73, CD105, and CD200, or express CD200 and OCT-4, or express CD73, CD105, and HLA-G, or express CD73 and CD105, and facilitate the formation of one or more embryoid-like bodies in a population of placental cells that comprise the stem cell, when said population is cultured under conditions that allow formation of embryoid-like bodies, or express OCT-4, and facilitate the formation of one or more embryoid-like bodies in a population of placental cells that comprise the stem cell, when said population is cultured under conditions that allow formation of embryoid-like bodies; and (c) detectably suppress proliferation of a tumor cell or plurality of tumor cells, or growth of a tumor.

3.1 DEFINITIONS

As used herein, the term "about denotes, e.g., a ±10% deviation from a stated value.

As used herein, the term "SH2" refers to an antibody that binds an epitope on the marker CD105. Thus, cells that are referred to as SH2$^+$ are CD105$^+$. See, e.g., U.S. Pat. No. 5,486,359.

As used herein, the terms "SH3" and SH4" refer to antibodies that bind epitopes present on the marker CD73. Thus, cells that are referred to as SH3$^+$ and/or SH4$^+$ are CD73$^+$. See, e.g., U.S. Pat. No. 5,486,359.

As used herein, the term "isolated stem cell" means a stem cell that is substantially separated from other, non-stem cells of the tissue, e.g., placenta, from which the stem cell is derived. A stem cell is "isolated" if at least 50%, 60%, 70%, 75%, 80%, 90%, 95%, or at least 99% of the non-stem cells with which the stem cell is naturally associated are removed from the stem cell, e.g., during collection and/or culture of the stem cell.

As used herein, the term "isolated population of cells" means a population of cells that is substantially separated from other cells of the tissue, e.g., placenta, from which the population of cells is derived. A stem cell is "isolated" if at least 50%, 60%, 70%, 75%, 80%, 90%, 95%, or at least 99% of the cells with which the population of cells, or cells from which the population of cells is derived, is naturally associated are removed from the stem cell, e.g., during collection and/or culture of the stem cell.

As used herein, the term "placental stem cell" refers to a stem cell or progenitor cell, that is derived from a mammalian placenta, regardless of morphology, cell surface markers, or the number of passages after a primary culture, which adheres to a tissue culture substrate (e.g., tissue culture plastic or a fibronectin-coated tissue culture plate). The term "placental stem cell" encompasses stem cells or progenitor cells derived from any portion of a mammalian placenta, including the amnion, chorion, amnion-chorion plate, and/or the umbilical cord, as well as cells derived from perfusion of the placenta. The term "placental stem cell" as used herein does not, however, refer to a trophoblast or a cell obtained from cord blood. A cell is considered a "stem cell" if the cell retains at least one attribute of a stem cell, e.g., the ability to differentiate into at least one other cell type.

As used herein, a stem cell is "positive" for a particular marker when that marker is detectable. For example, a placental stem cell is positive for, e.g., CD73 (that is, is CD73$^+$) because CD73 is detectable on placental stem cells in an amount detectably greater than background (in comparison to, e.g., an isotype control). A cell is also positive for a marker when that marker can be used to distinguish the cell from at least one other cell type, or can be used to select or isolate the cell when present or expressed by the cell.

A "tumor cell" in the context of this method means any cell exhibiting a non-normal growth pattern, and includes benign but hyperplasic cells, cancer cells, metastatic cells, and the like. A "tumor cell" can be, e.g., a cell in a solid tumor, or a cell having the potential or ability to form a solid tumor, or a cell of a non-solid tumor, e.g. the cell of a blood cancer. In certain embodiments, the tumor cell is derived from a cell of epithelial, glandular, or hematopoietic origin. In certain embodiments, the tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells.

As used herein, "suppress the proliferation of a tumor cell, or a plurality of tumor cells" means to reduce the amount of proliferation of a tumor cell or plurality of tumor cells in comparison to a control or standard. For example, the proliferation of a tumor cell or plurality of tumor cells in the presence of, e.g., a plurality of placental stem cells, is compared to the proliferation of the same type of tumor cell or plurality of tumor cells in the absence of the placental stem cells. The term encompasses a detectable reduction in the proliferation of the tumor cell or plurality of tumor cells, a cessation of proliferation, or a reduction in the number of tumor cells.

4. BRIEF DESCRIPTION OF THE FIGURES

FIG. 1: Viability of placental stem cells from perfusion (A), amnion (B), chorion (C), or amnion-chorion plate (D); or umbilical cord stem cells (E). Numbers on X-axis designate placenta from which stem cells were obtained.

Figure 2:
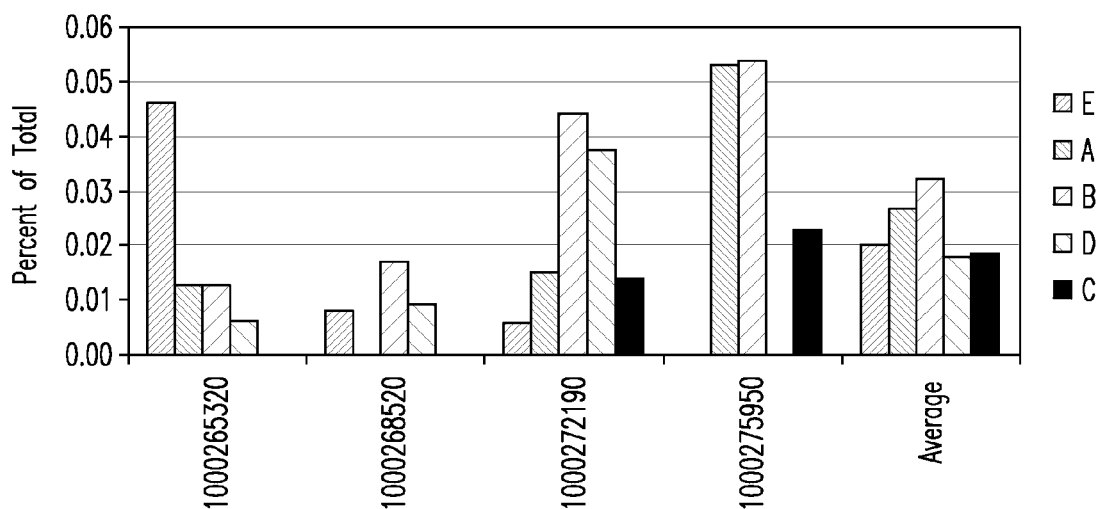

FIG. 2: Percent HLA ABC$^-$/CD45$^-$/CD34$^-$/CD133$^+$ cells from perfusion (A), amnion (B), chorion (C), amnion-chorion plate (D) or umbilical cord (E) as determined by FACSCalibur. Numbers on X-axis designate placenta from which stem cells were obtained.

Figure 3:
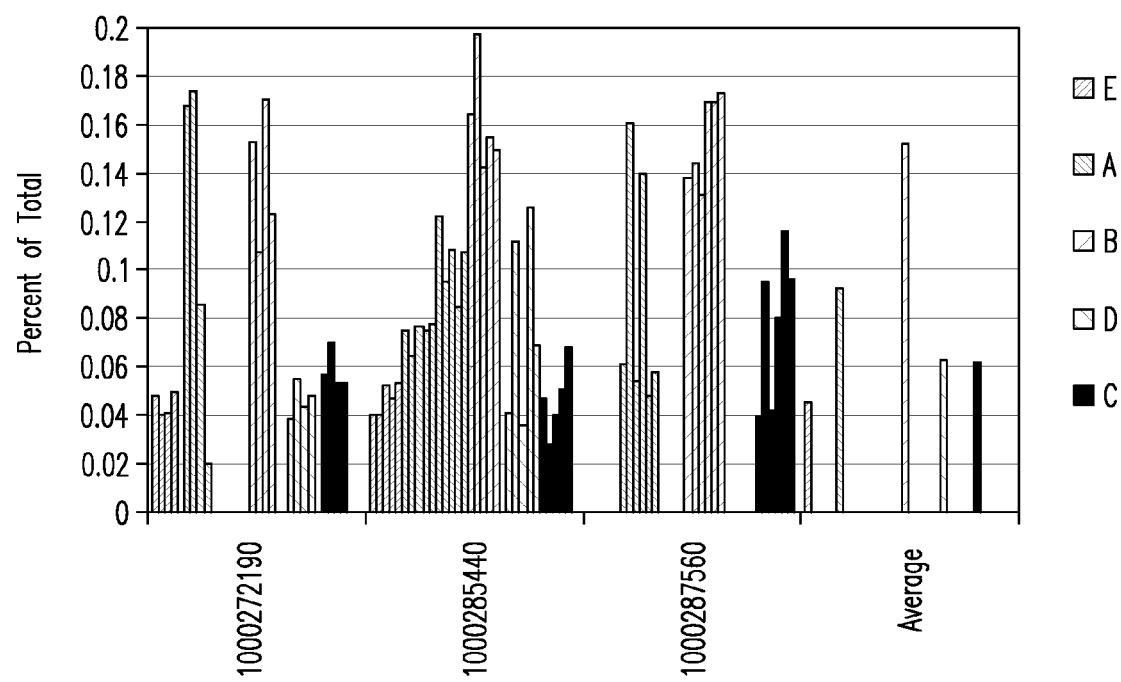
Figure 4A:
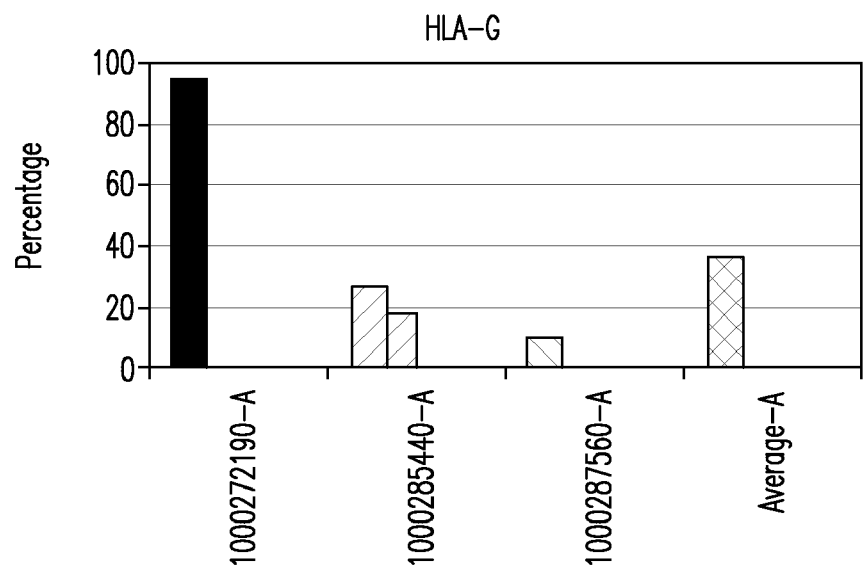
Figure 4B:
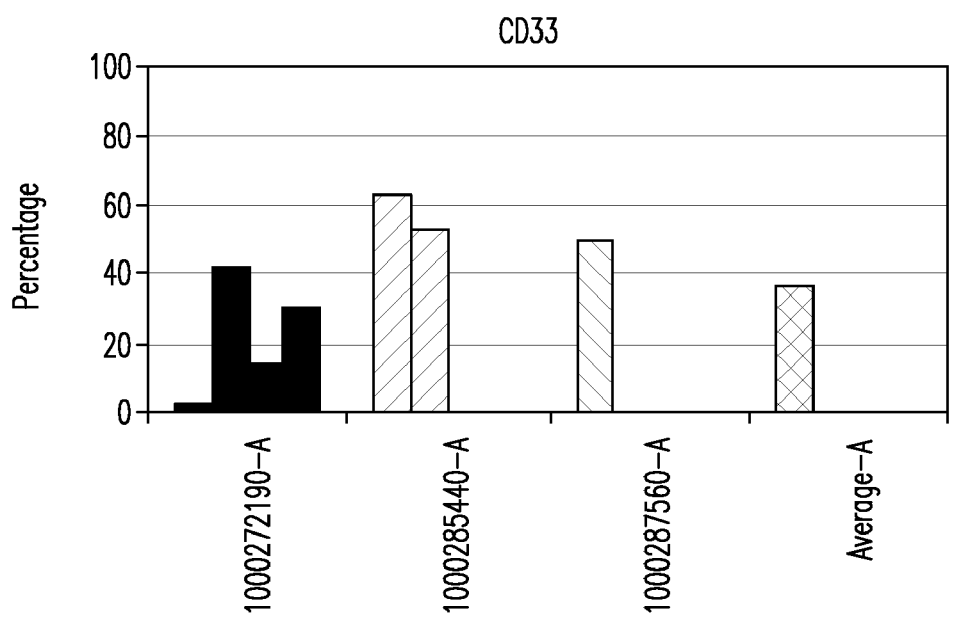
Figure 4C:
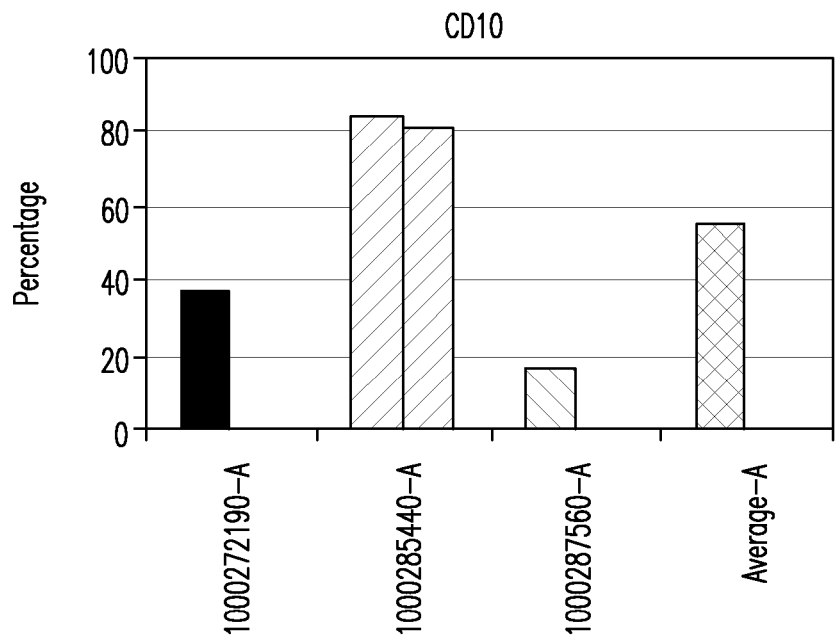
Figure 4D:
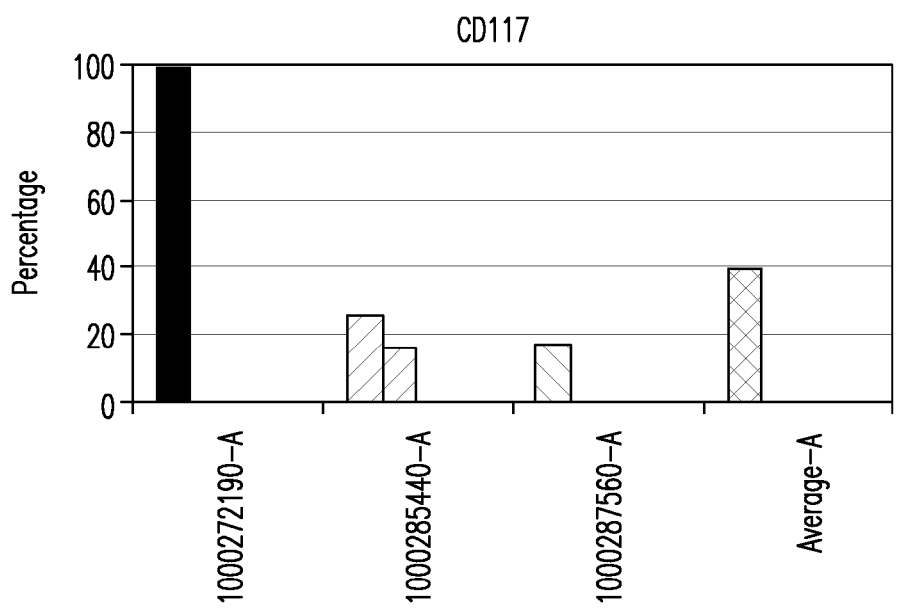
Figure 4E:
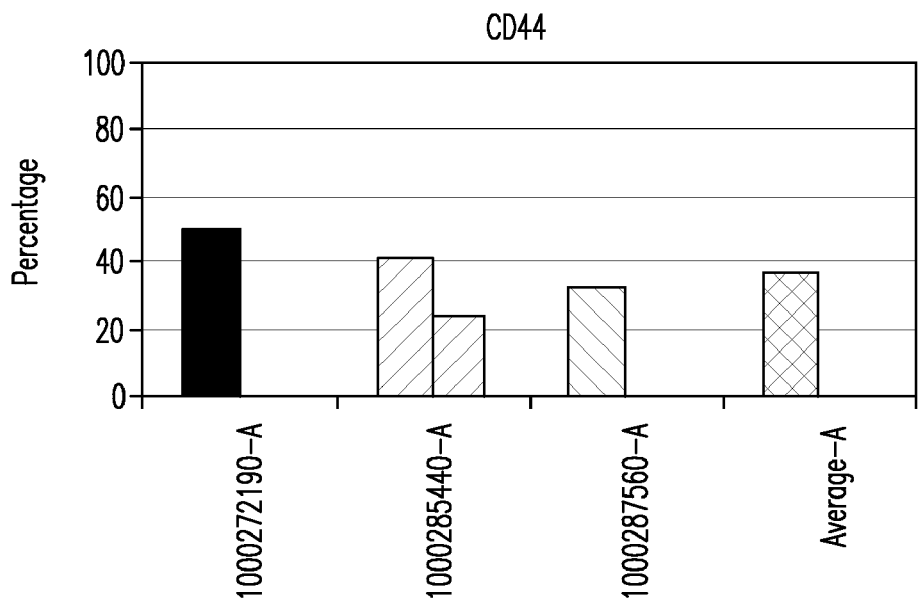
Figure 4F:
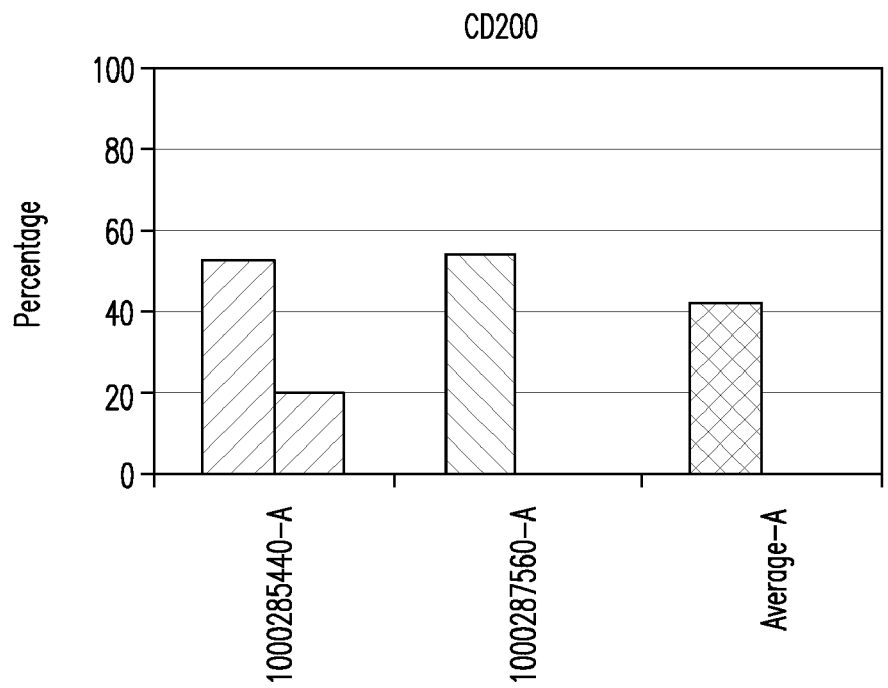
Figure 4G:
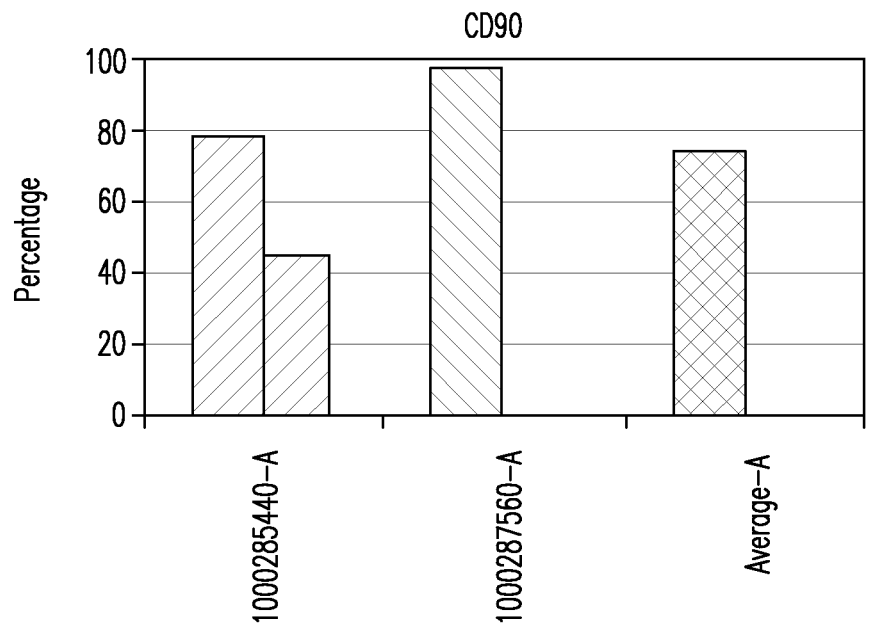
Figure 4H:
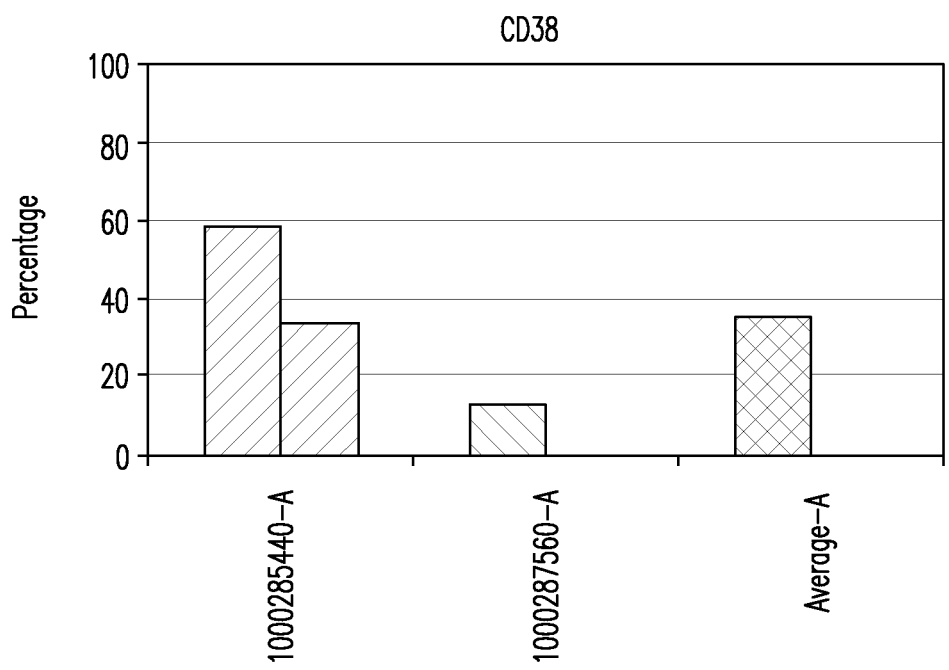
Figure 4I:
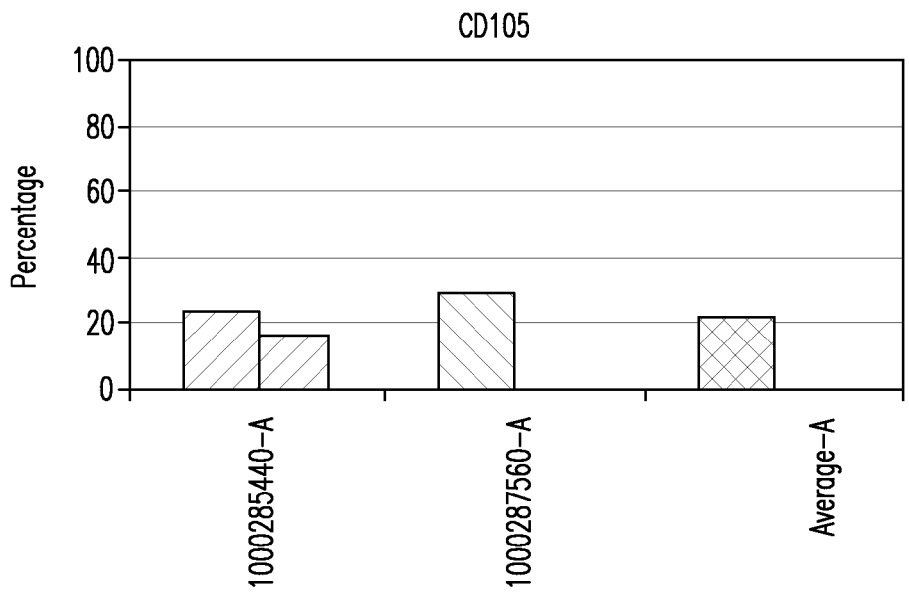
Figure 4J:
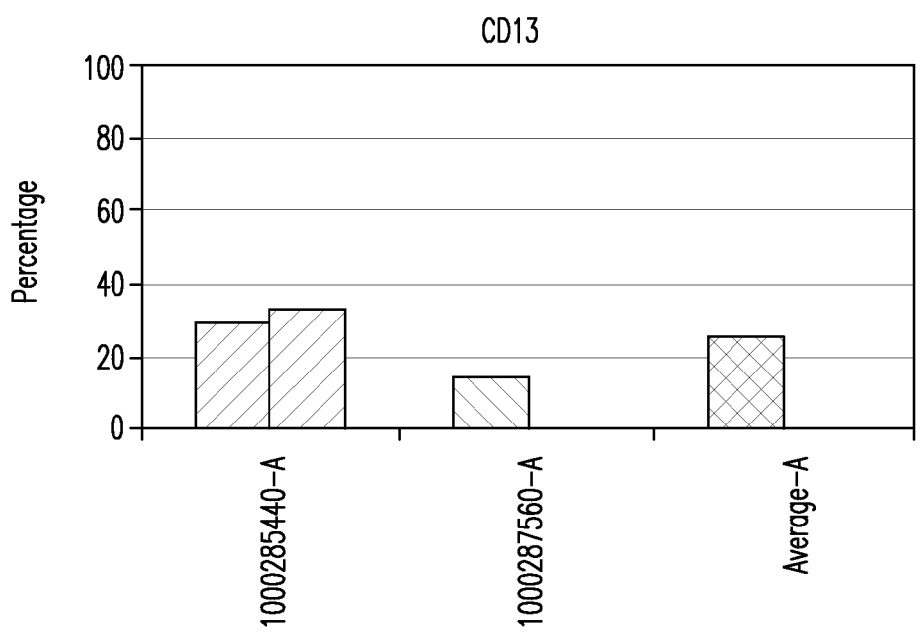
Figure 5A:
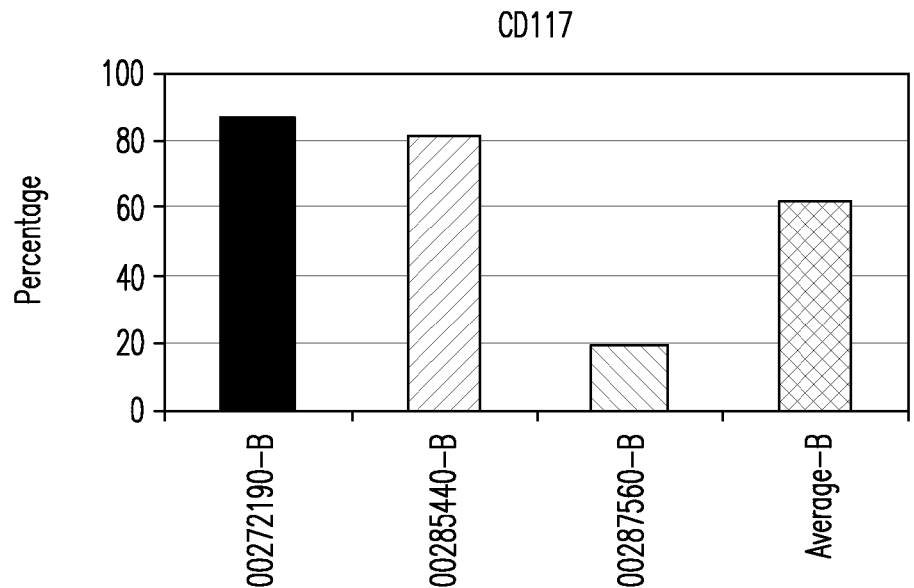
Figure 5B:
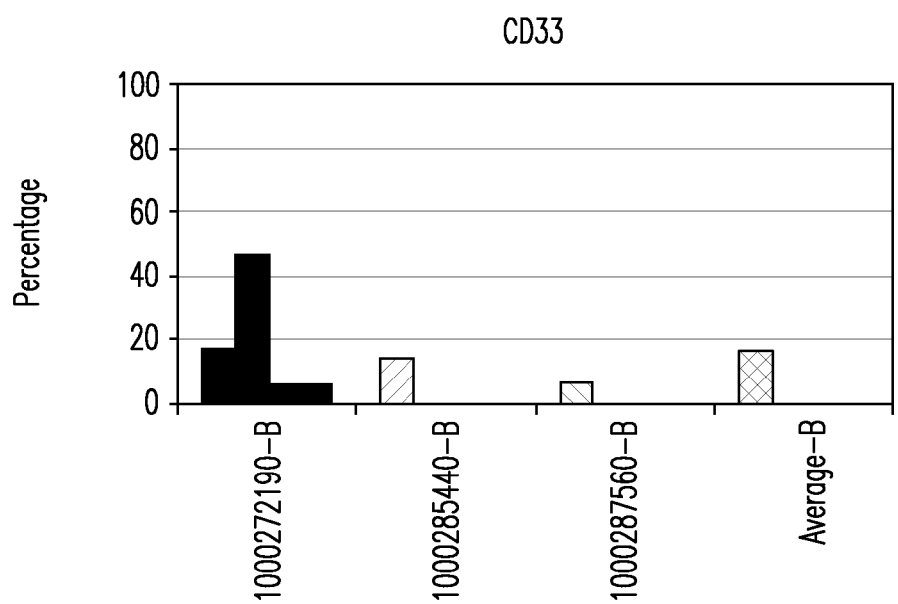
Figure 5C:
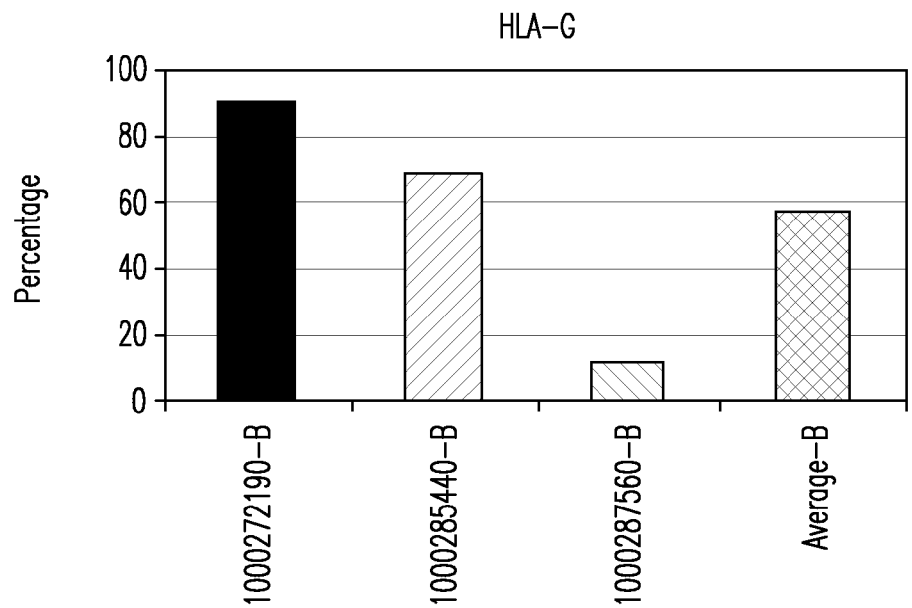
Figure 5D:
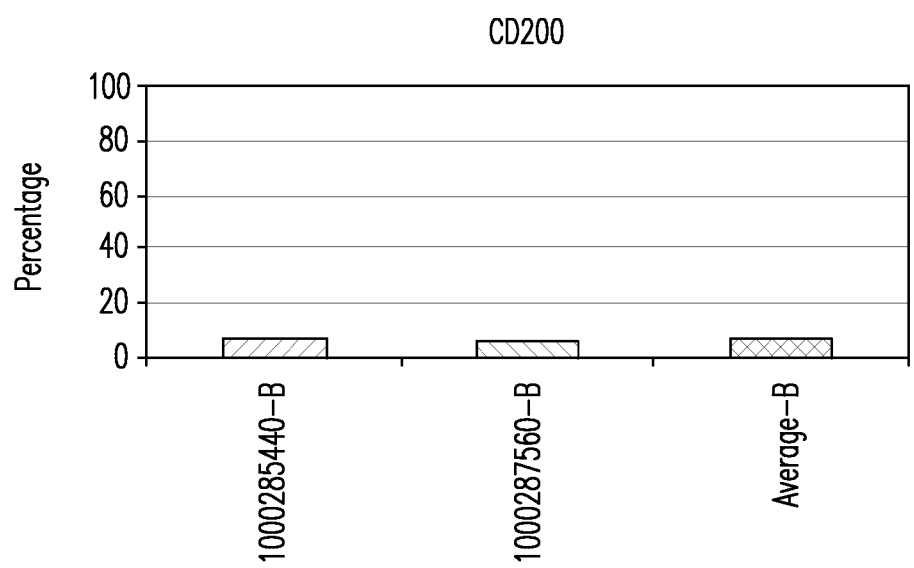
Figure 5E:
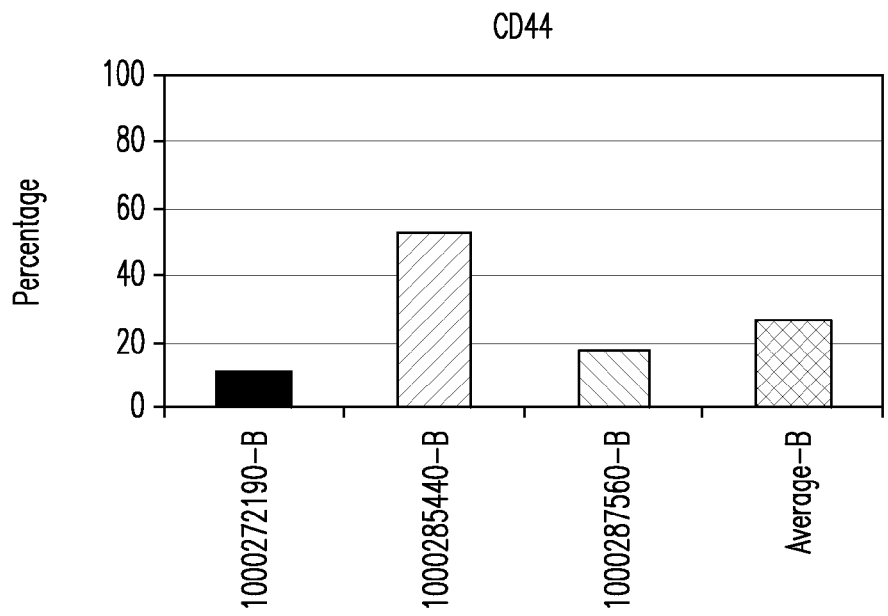
Figure 5F:
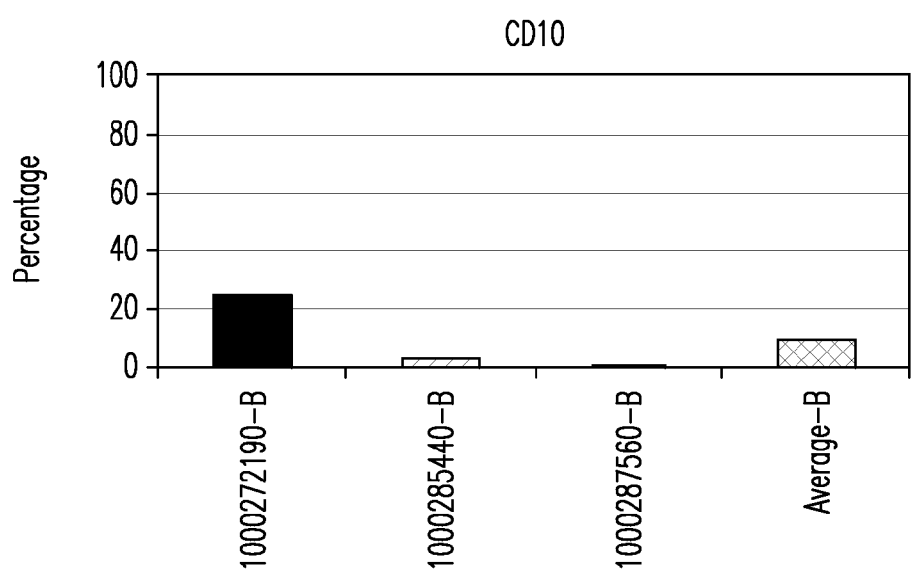
Figure 5G:
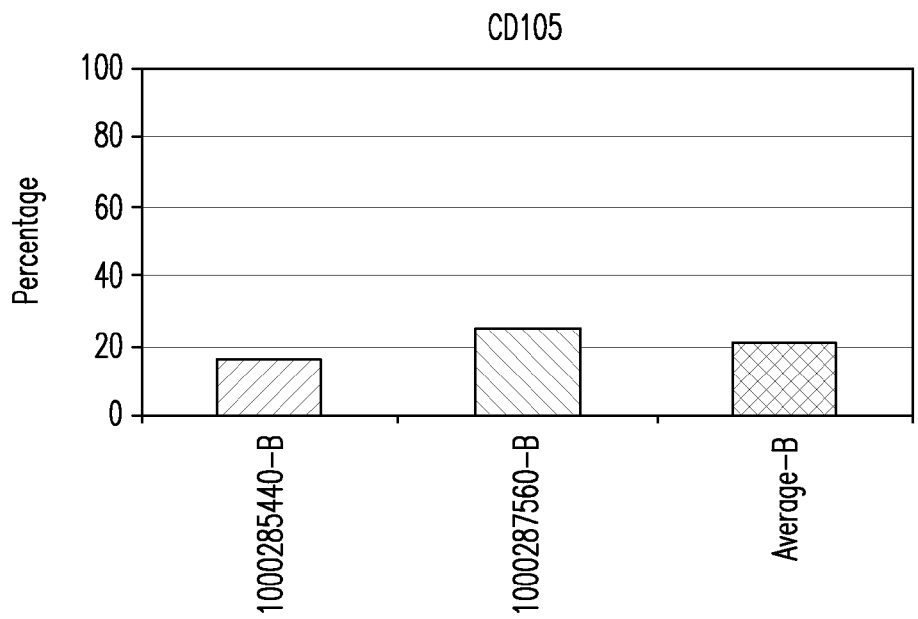
Figure 5H:
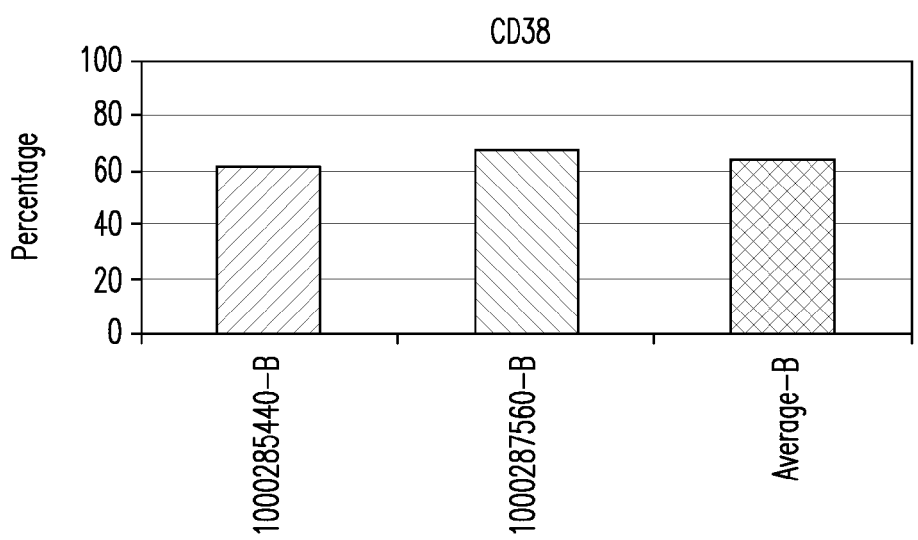
Figure 5I:
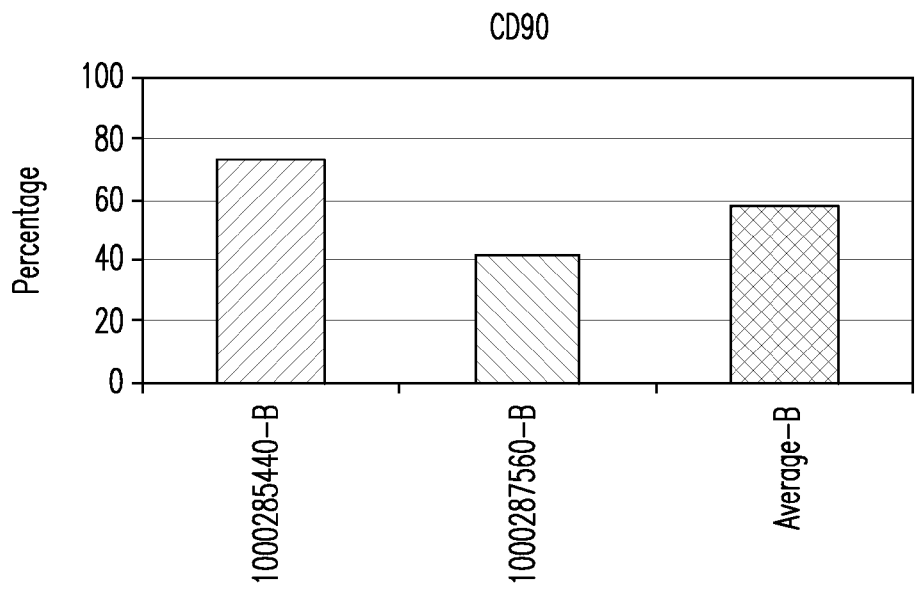
Figure 5J:
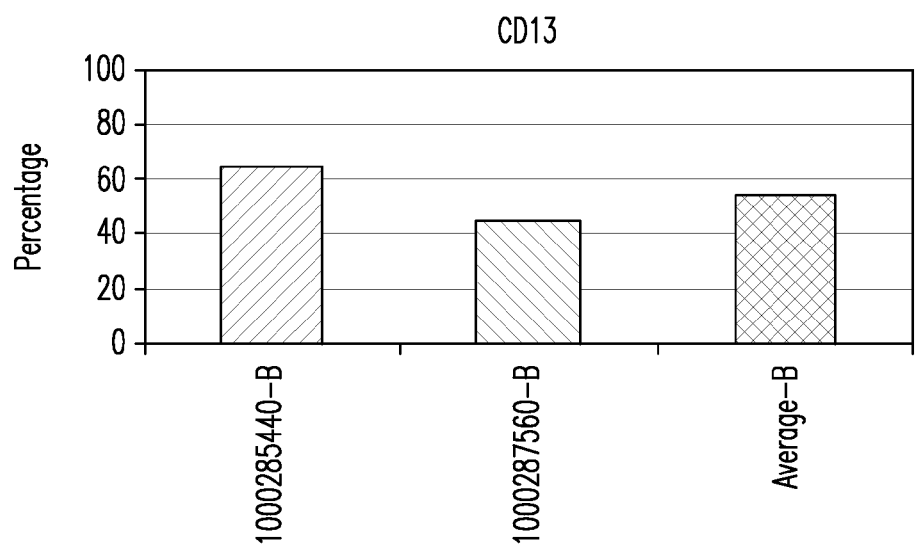
Figure 6A:
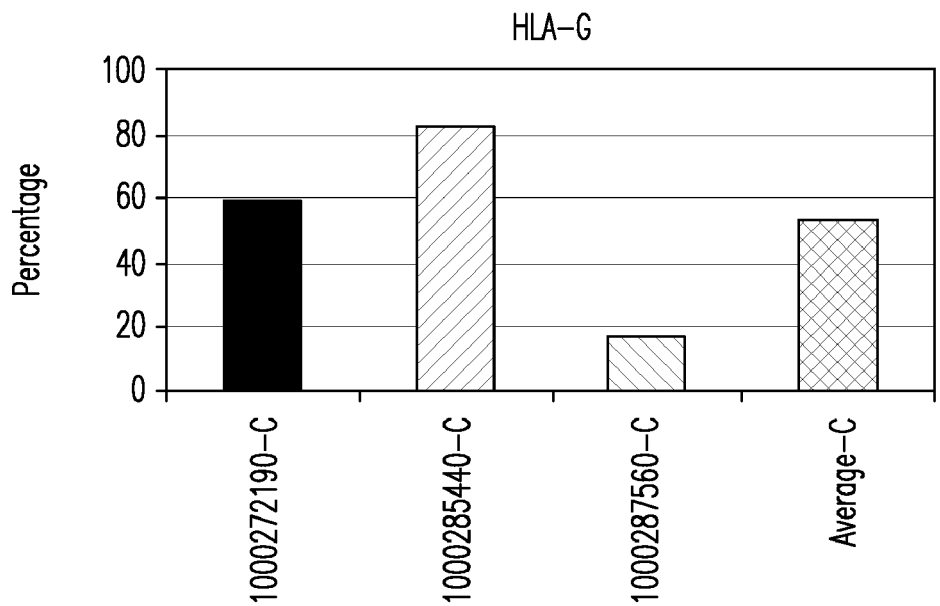
Figure 6B:
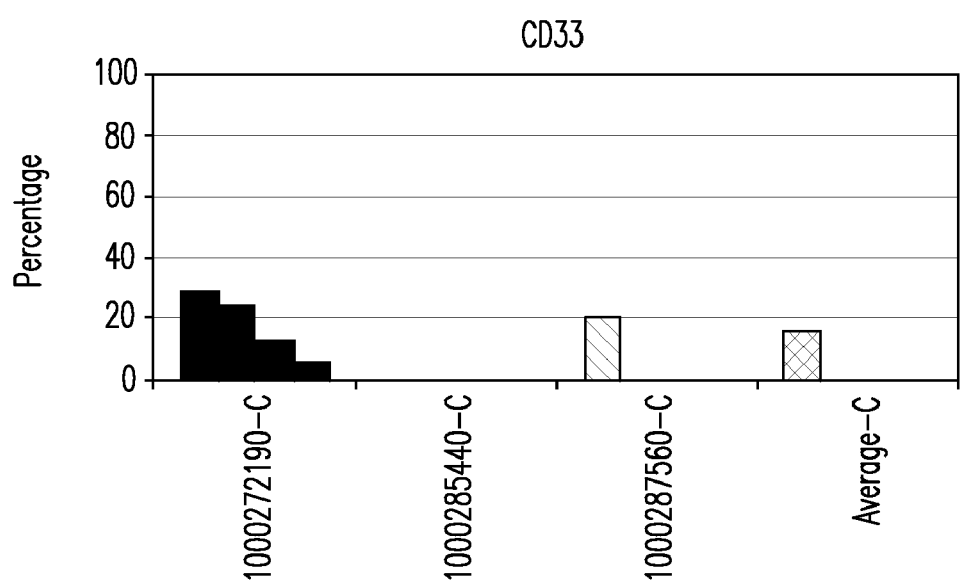
Figure 6C:
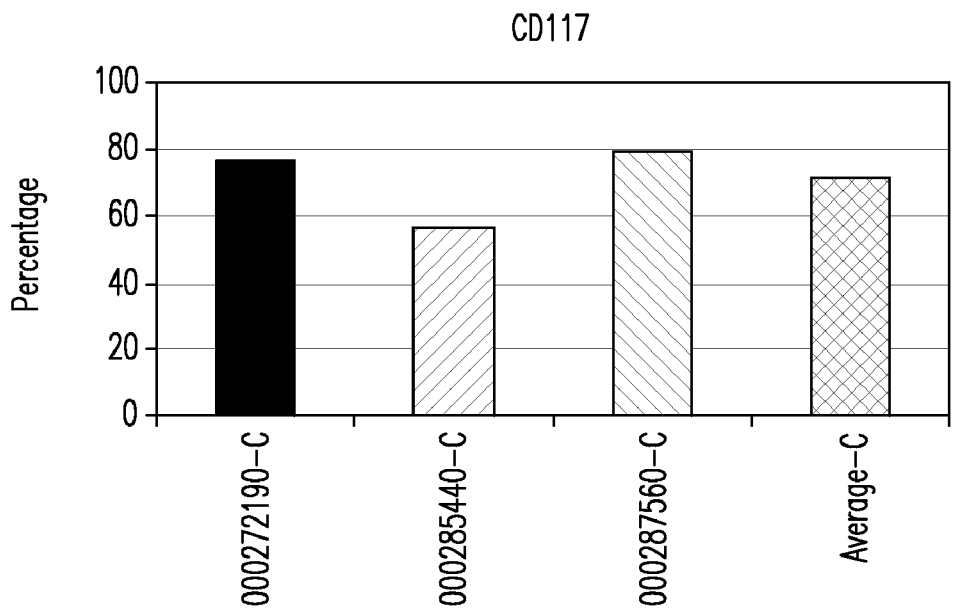
Figure 6D:
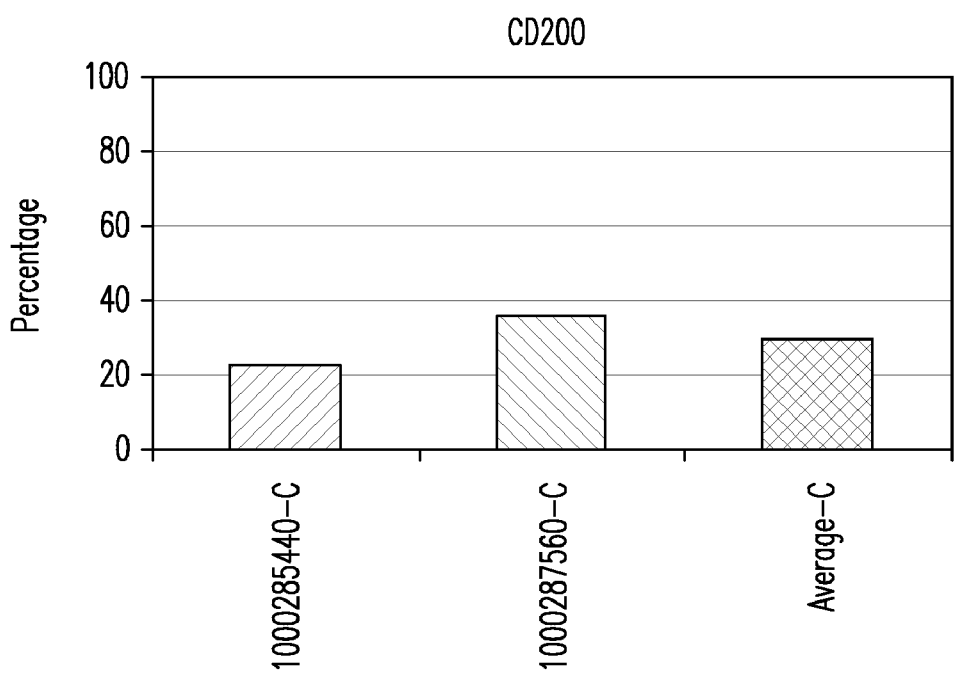
Figure 6E:
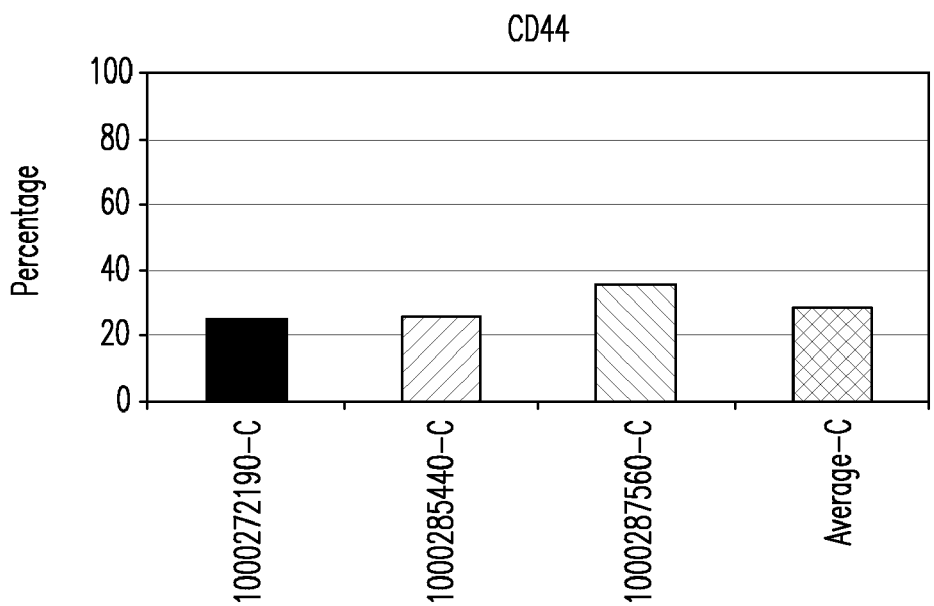
Figure 6F:
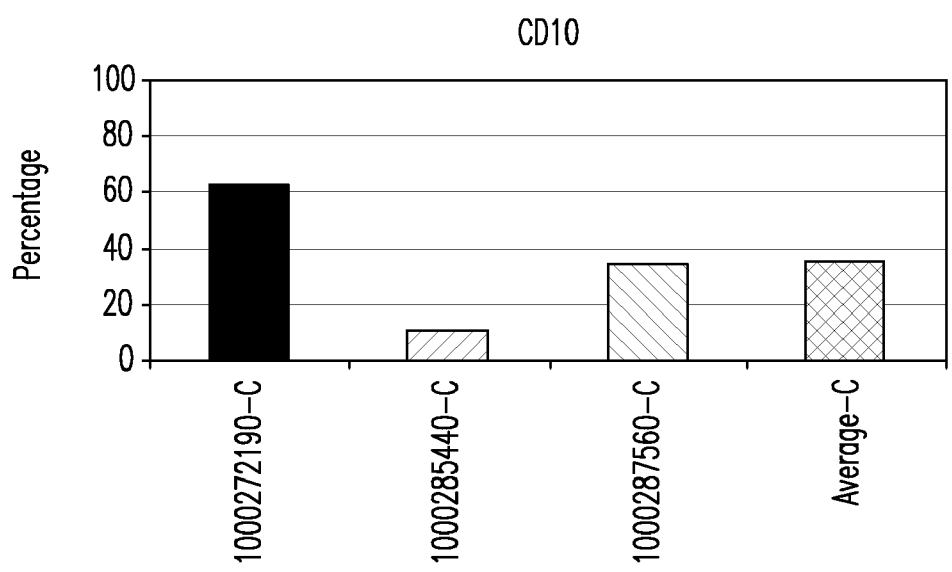
Figure 6G:
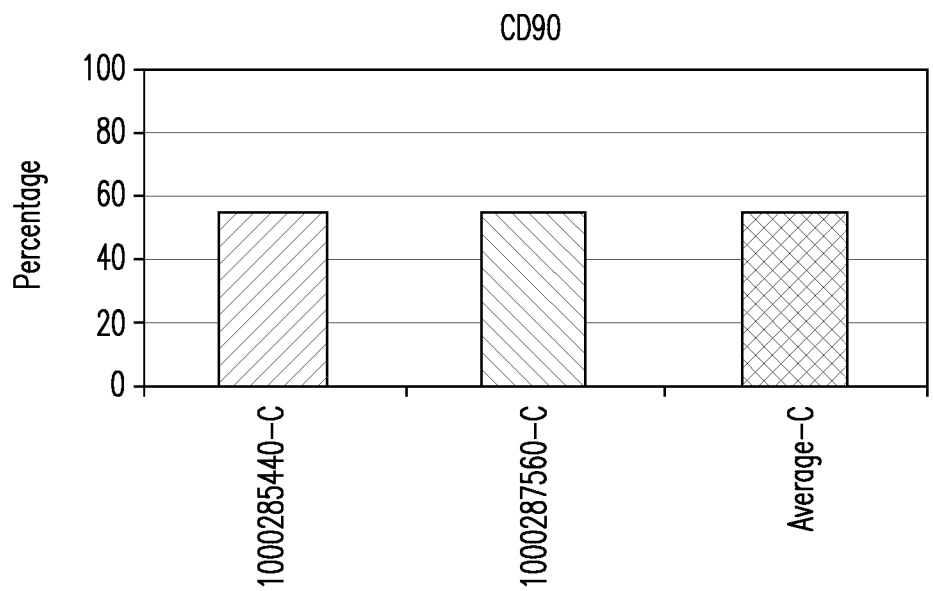
Figure 6H:
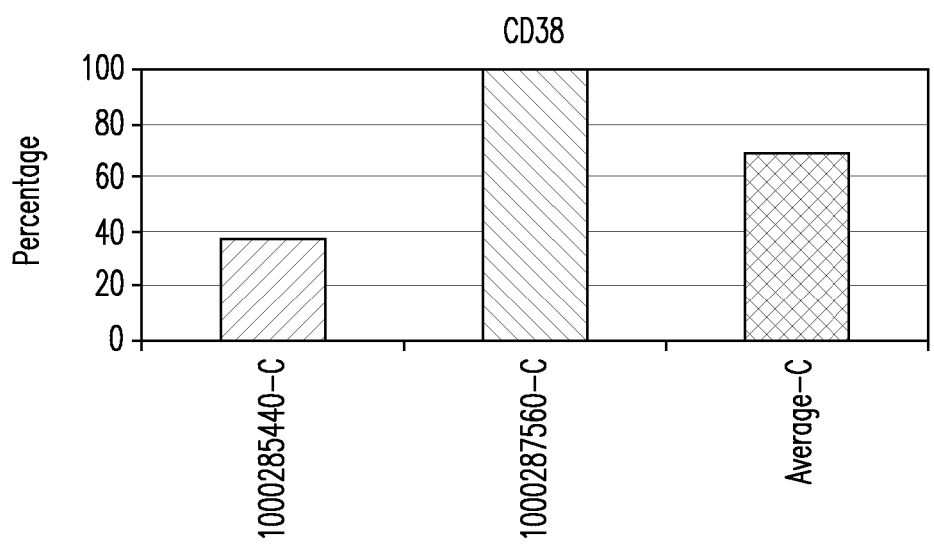
Figure 6I:
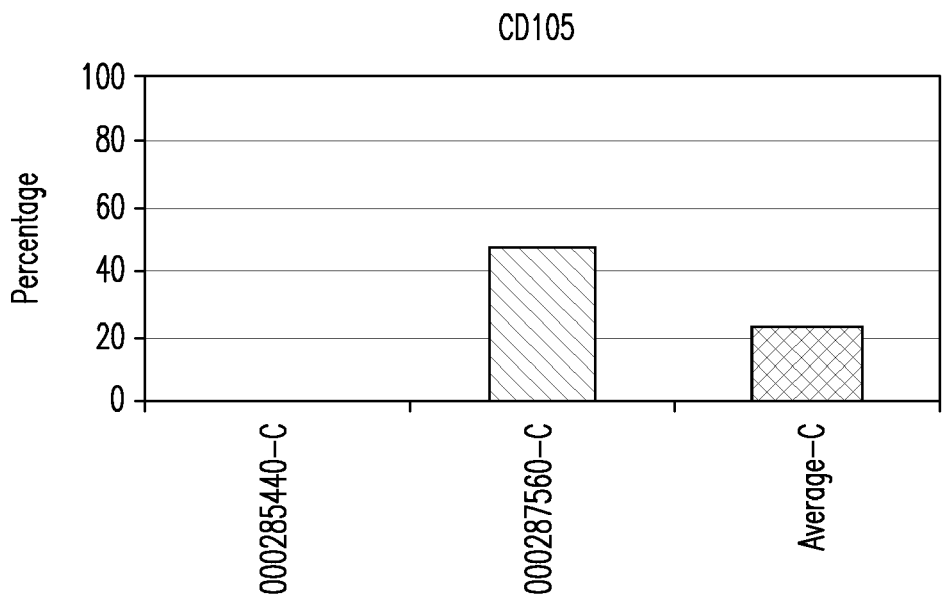
Figure 6J:
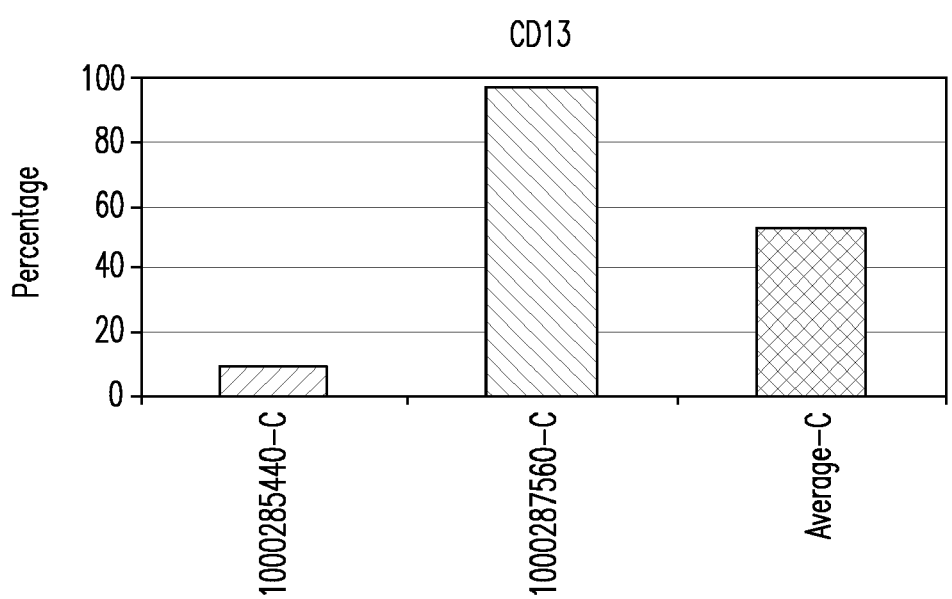
Figure 7A:
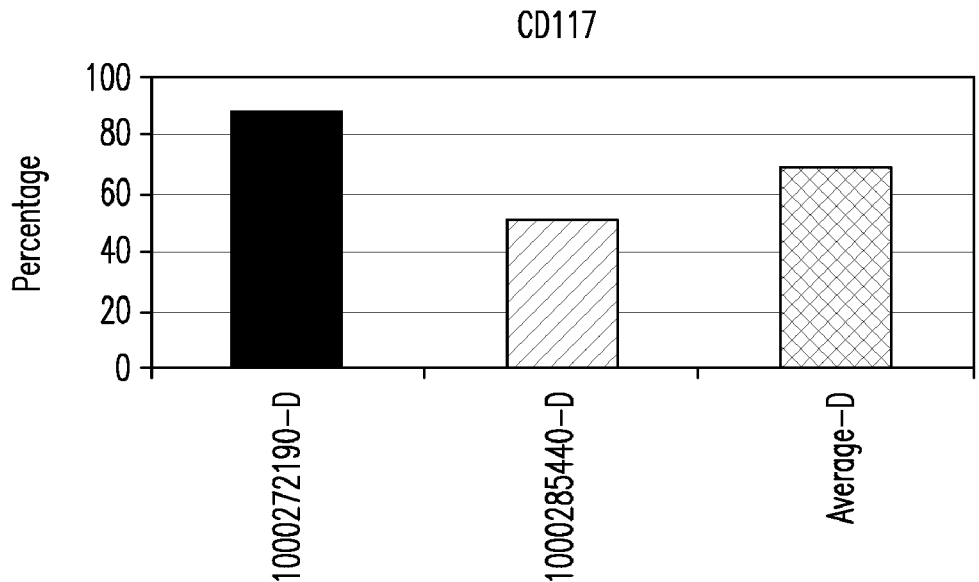
Figure 7B:
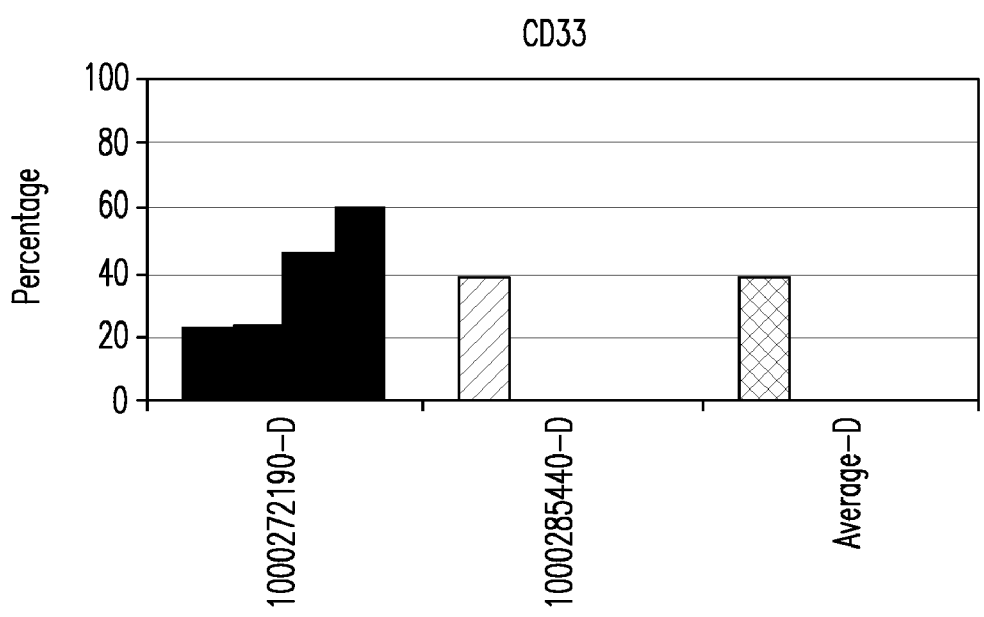
Figure 7C:
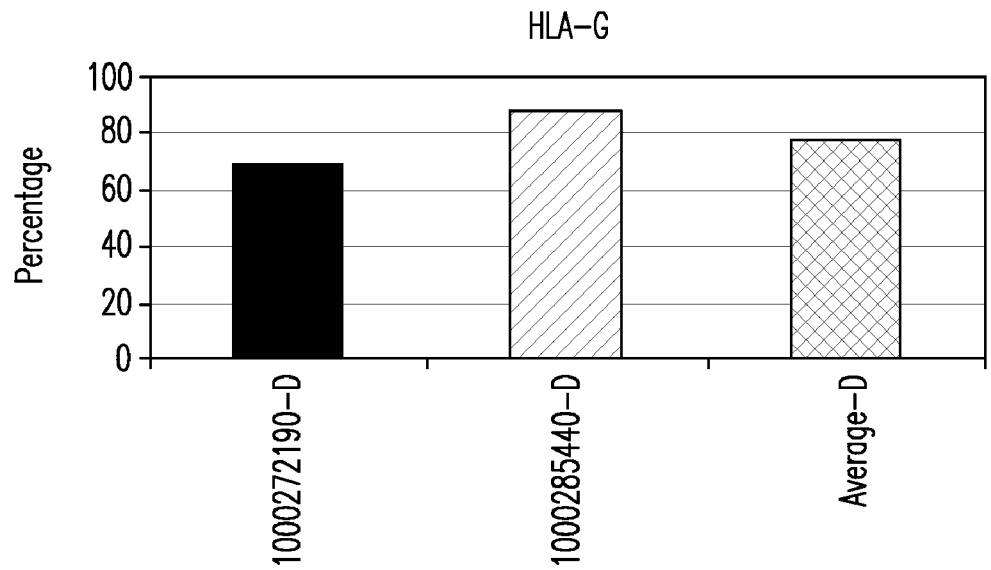
Figure 7D:
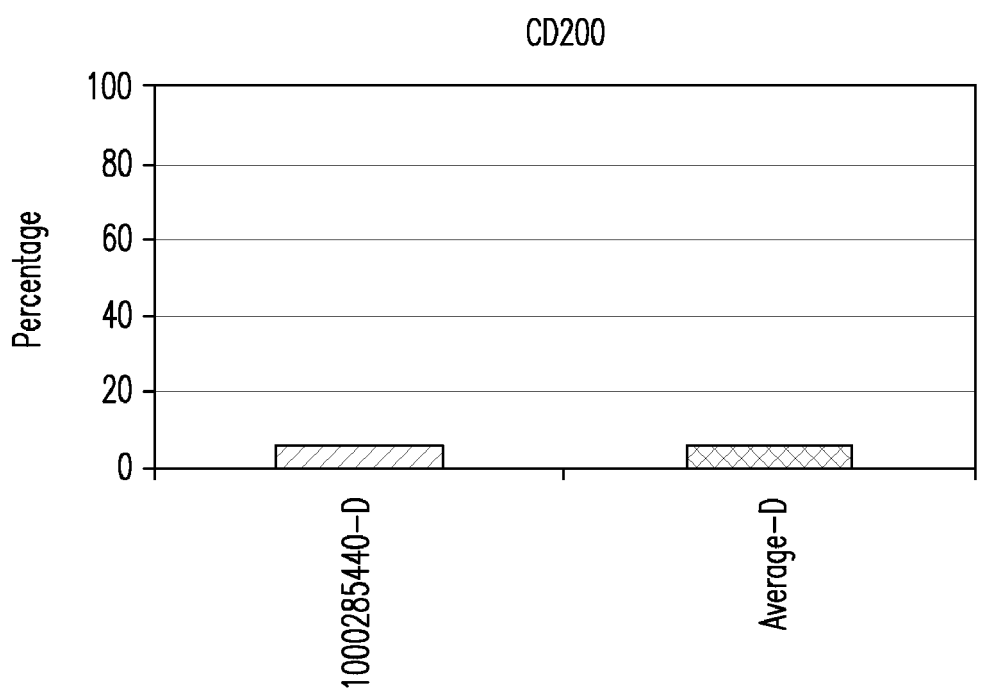
Figure 7E:
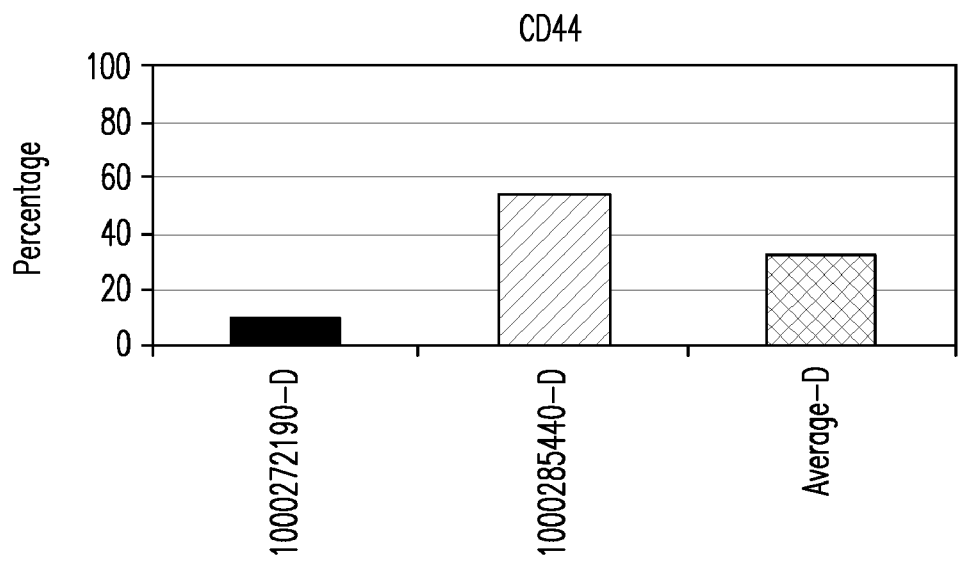
Figure 7F:
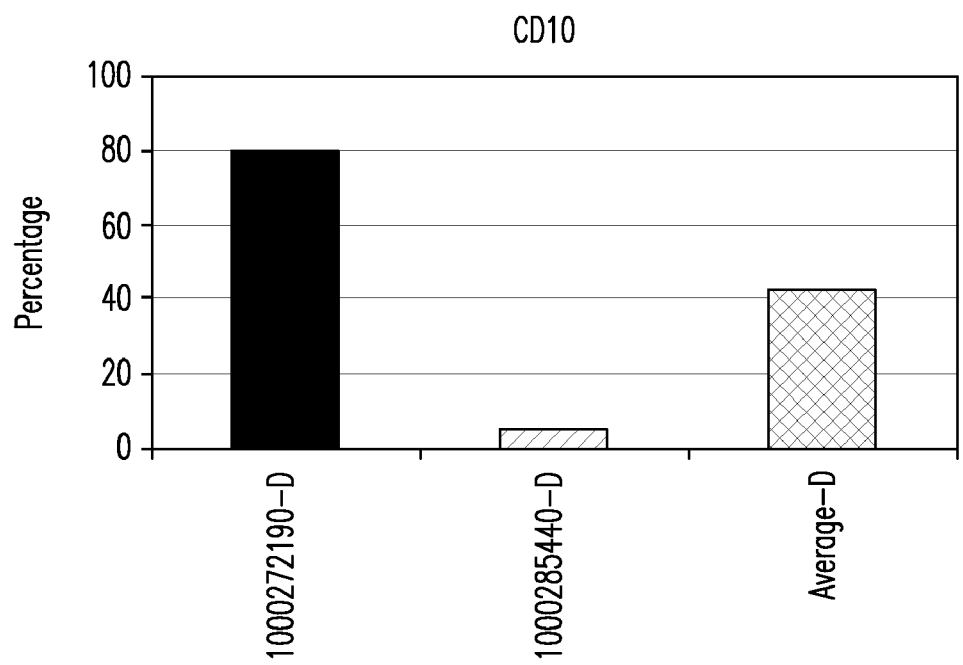
Figure 7G:
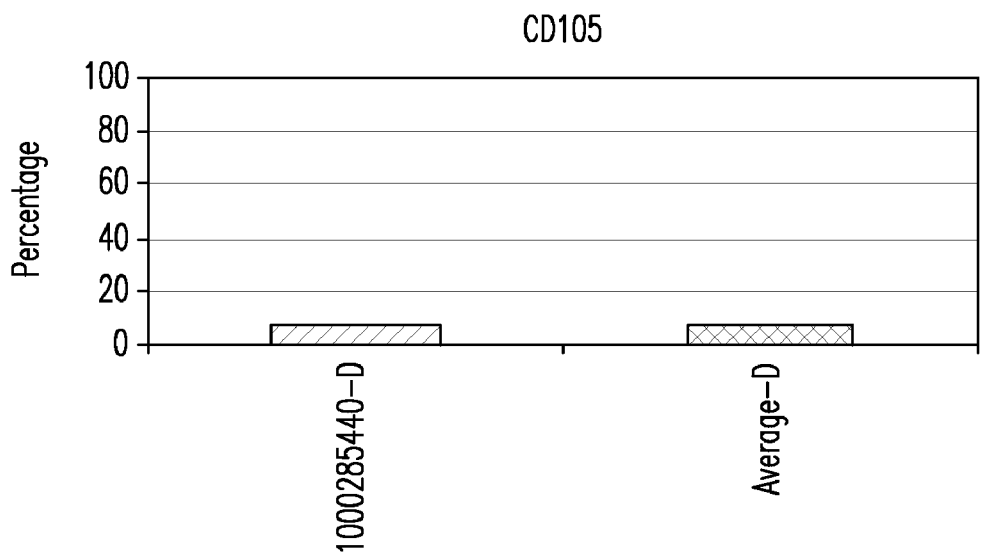
Figure 7H:
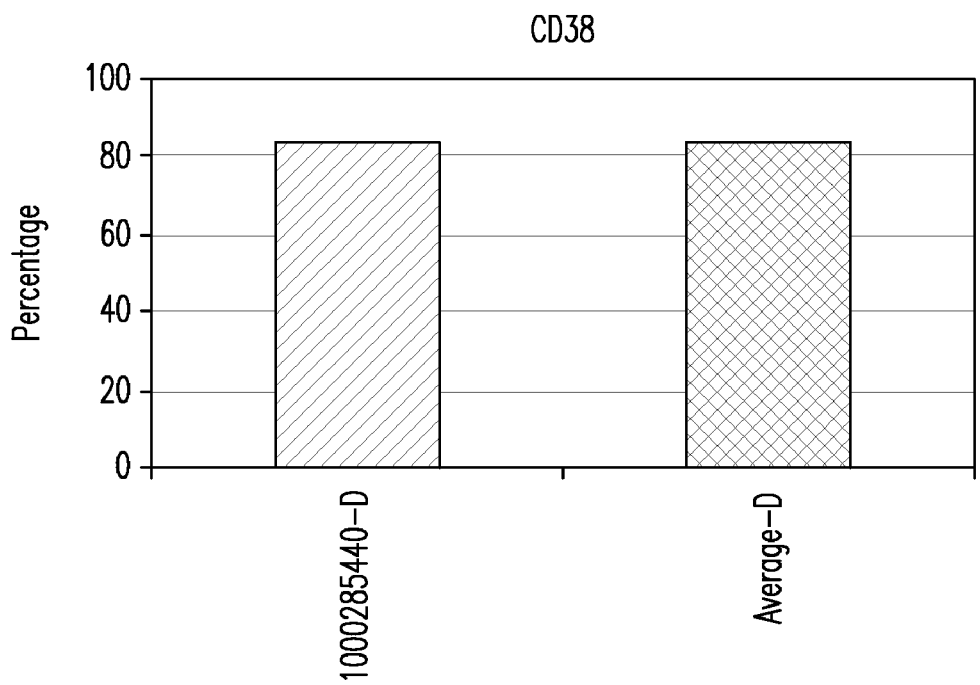
Figure 7I:
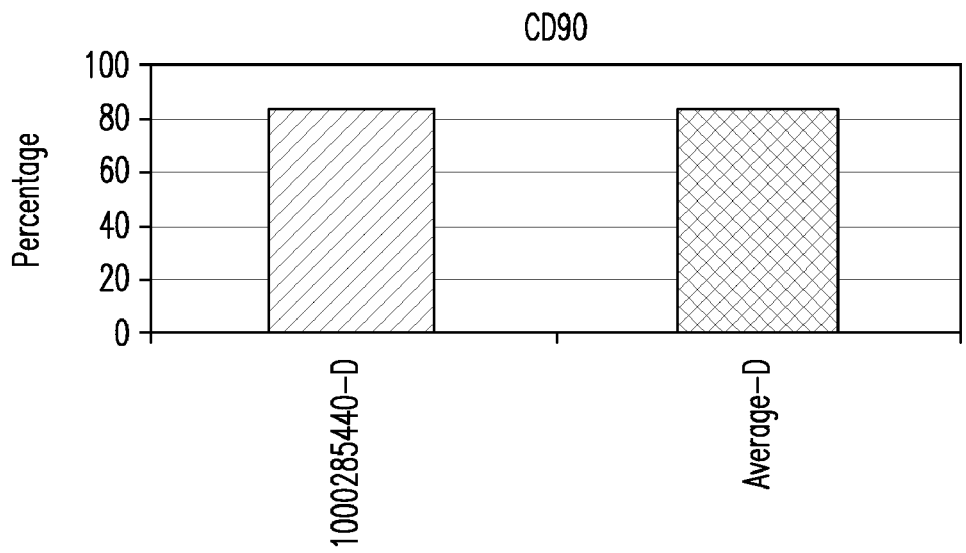
Figure 7J:
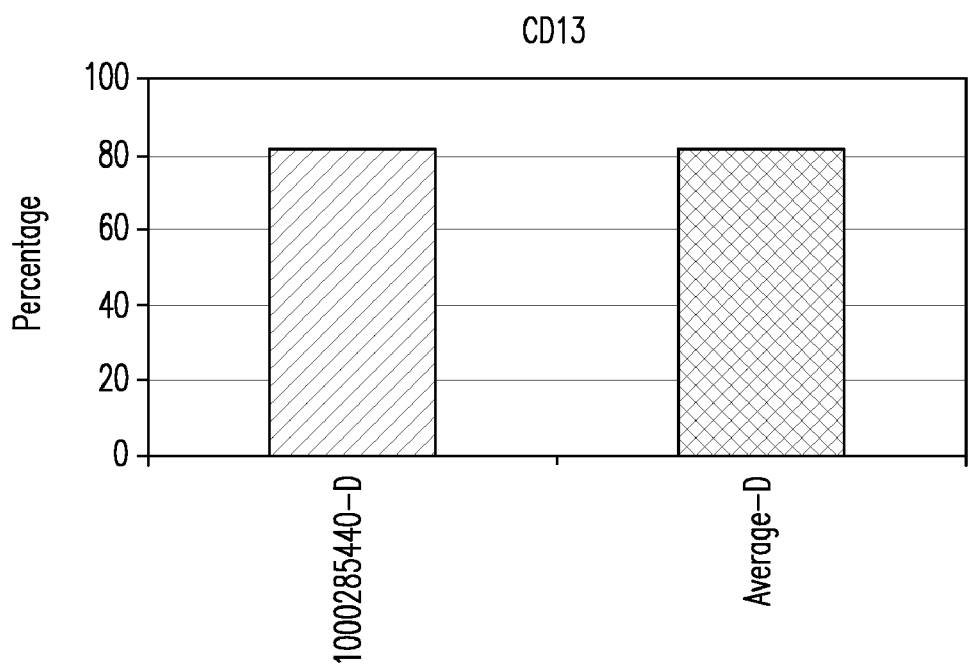
Figure 8A:
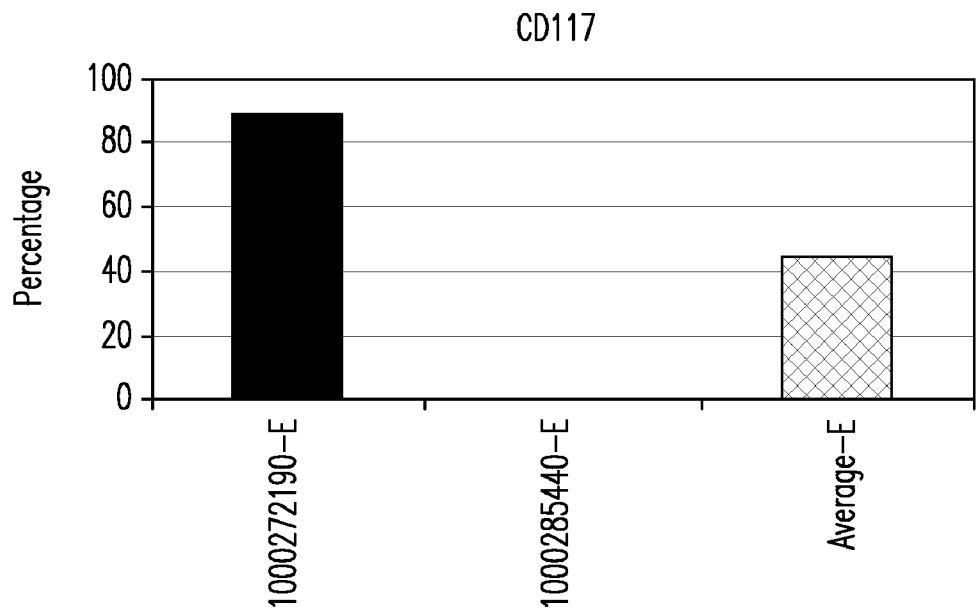
Figure 8B:
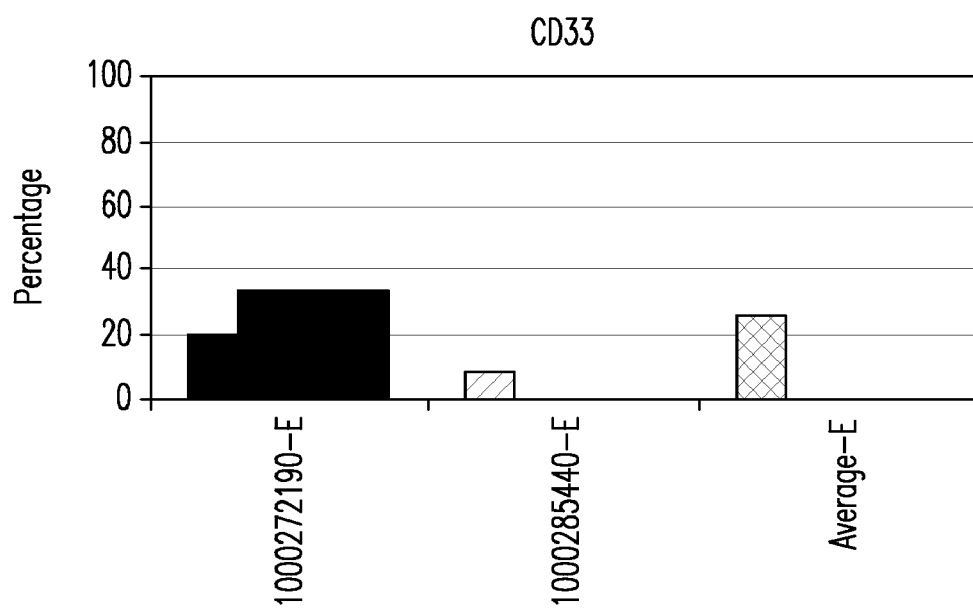
Figure 8C:
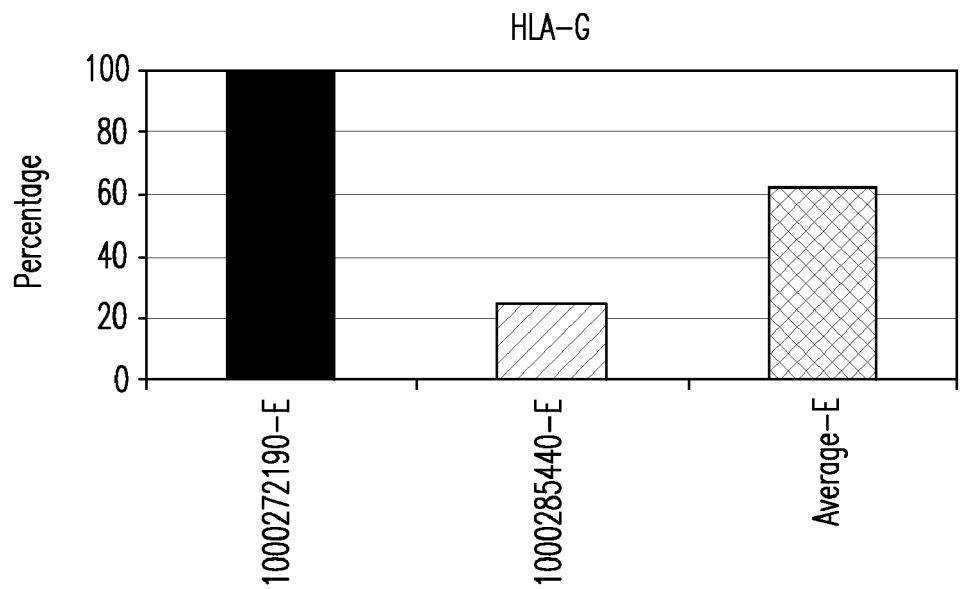
Figure 8D:
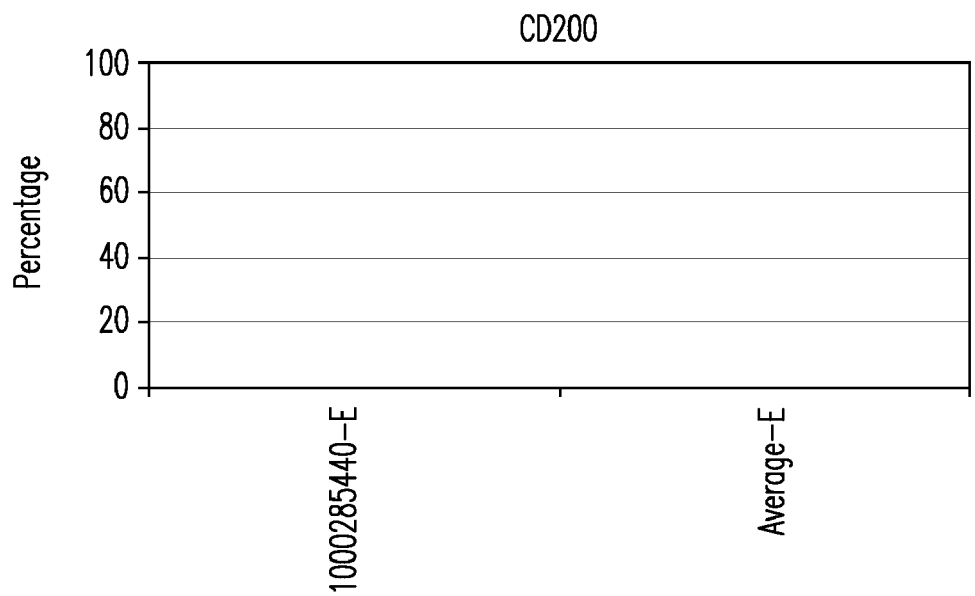
Figure 8E:
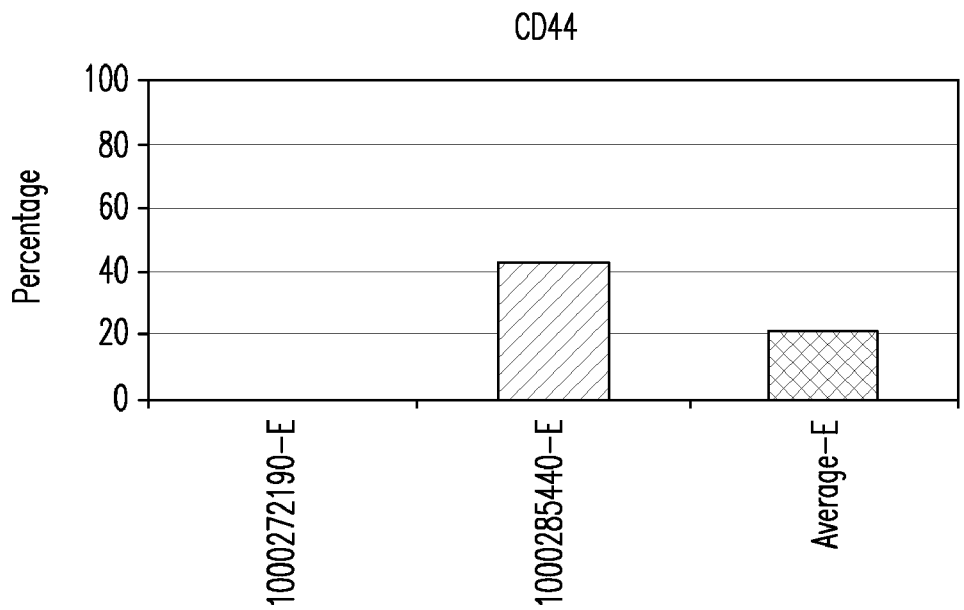
Figure 8F:
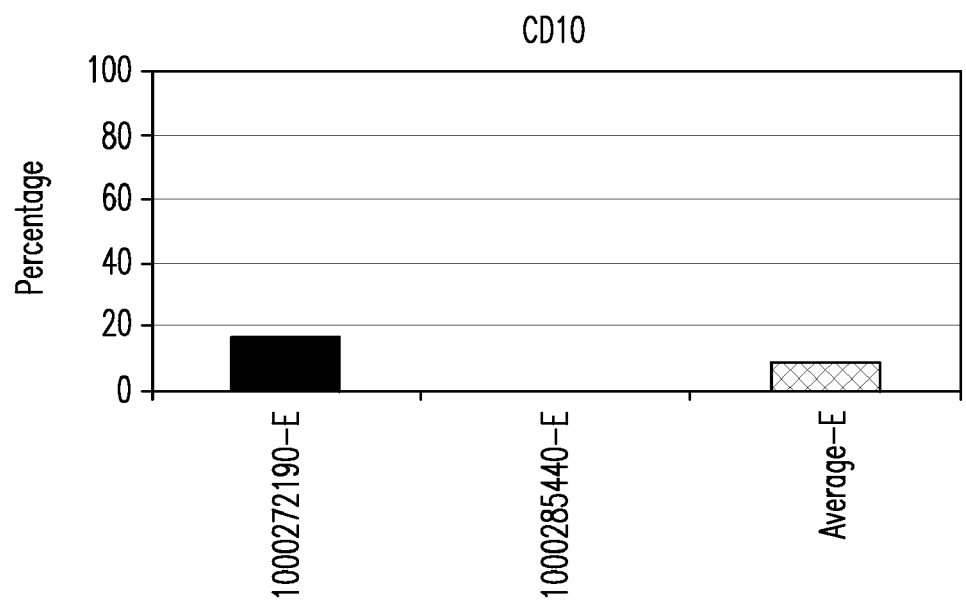
Figure 8G:
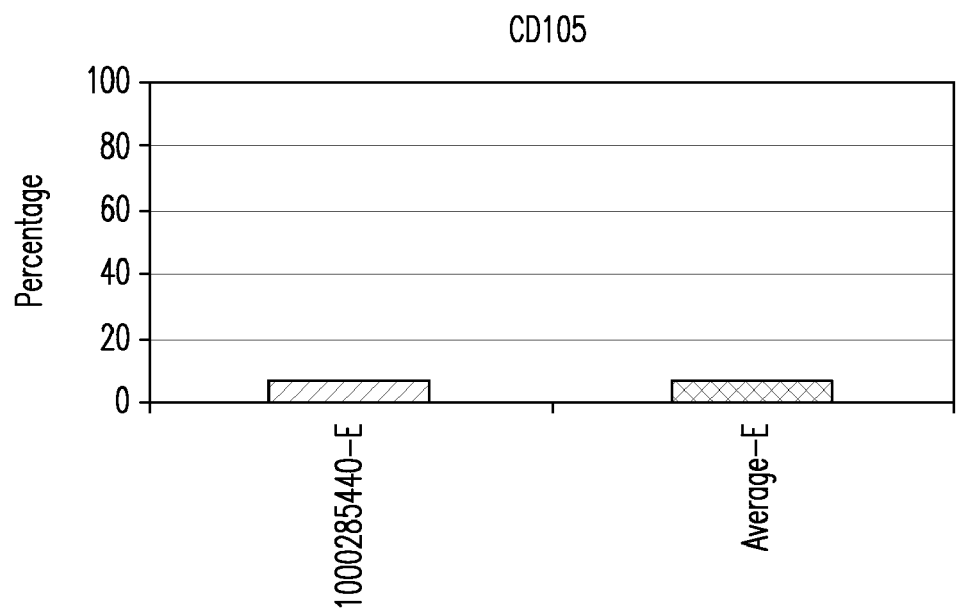
Figure 8H:
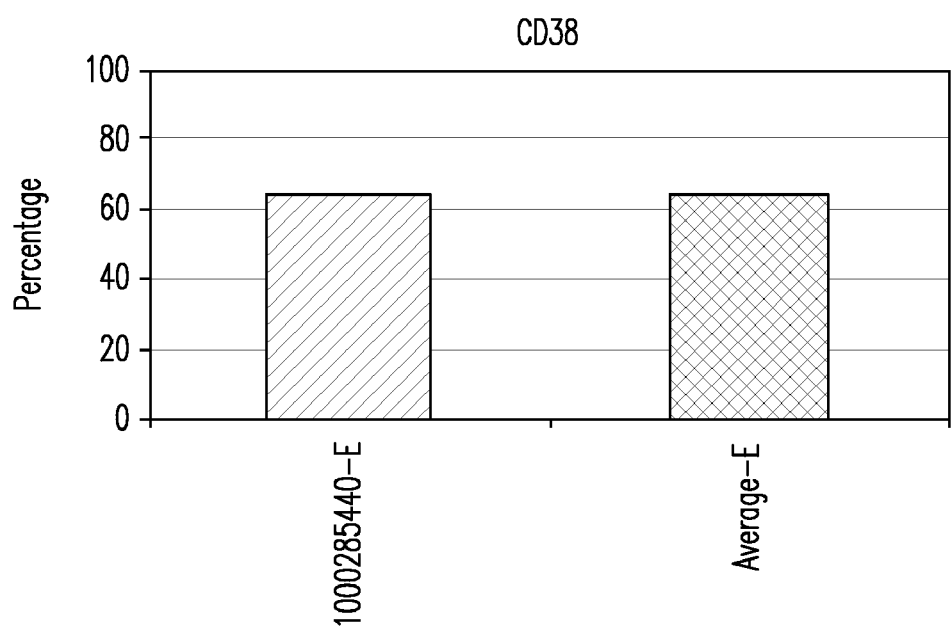
Figure 8I:
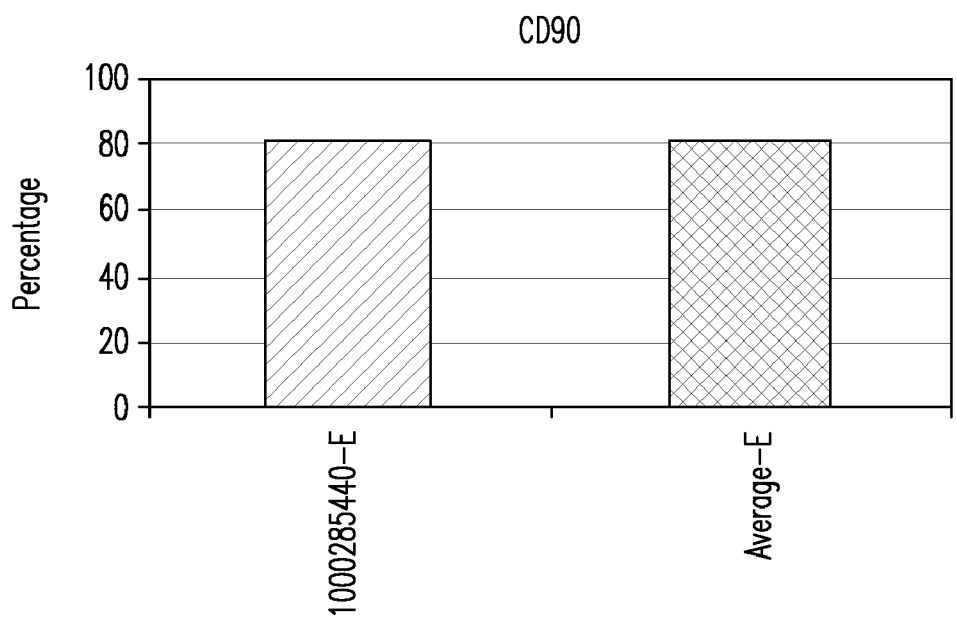
Figure 8J:
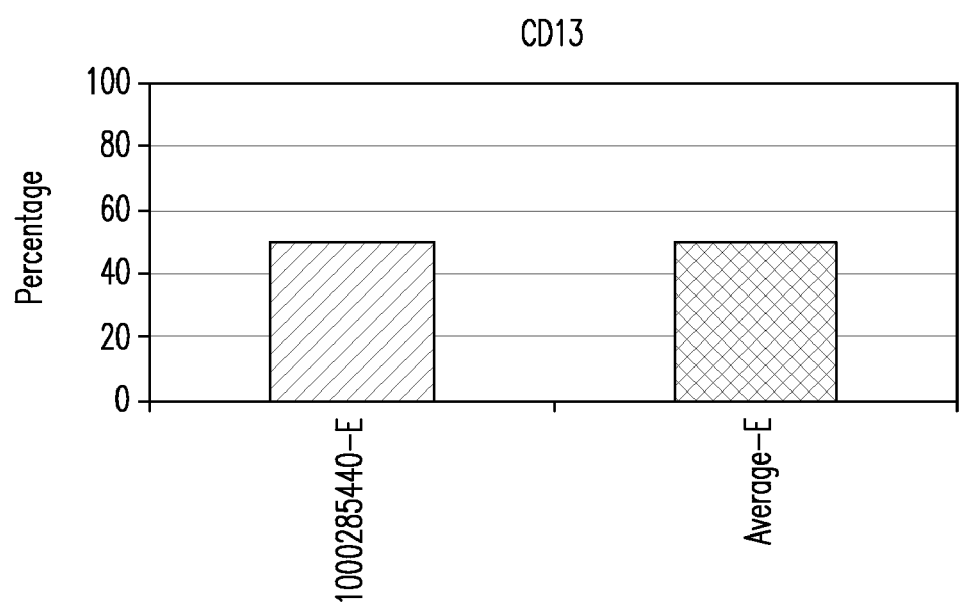

FIG. 3: Percent HLA ABC$^-$/CD45$^-$/CD34$^-$/CD133$^+$ cells from perfusion (A), amnion (B), chorion (C), amnion-chorion plate (D) or umbilical cord (E), as determined by FACS Aria. Numbers on X-axis designate placenta from which stem cells were obtained.

FIG. 4: HLA-G, CD10, CD13, CD33, CD38, CD44, CD90, CD105, CD117, CD200 expression in stem cells derived from placental perfusate.

FIG. 5: HLA-G, CD10, CD13, CD33, CD38, CD44, CD90, CD105, CD117, CD200 expression in stem cells derived from amnion.

FIG. 6: HLA-G, CD10, CD13, CD33, CD38, CD44, CD90, CD105, CD117, CD200 expression in stem cells derived from chorion.

FIG. 7: HLA-G, CD10, CD13, CD33, CD38, CD44, CD90, CD105, CD117, CD200 expression in stem cells derived from amnion-chorion plate.

FIG. 8: HLA-G, CD10, CD13, CD33, CD38, CD44, CD90, CD105, CD117, CD200 expression in stem cells derived from umbilical cord.

Figure 9:
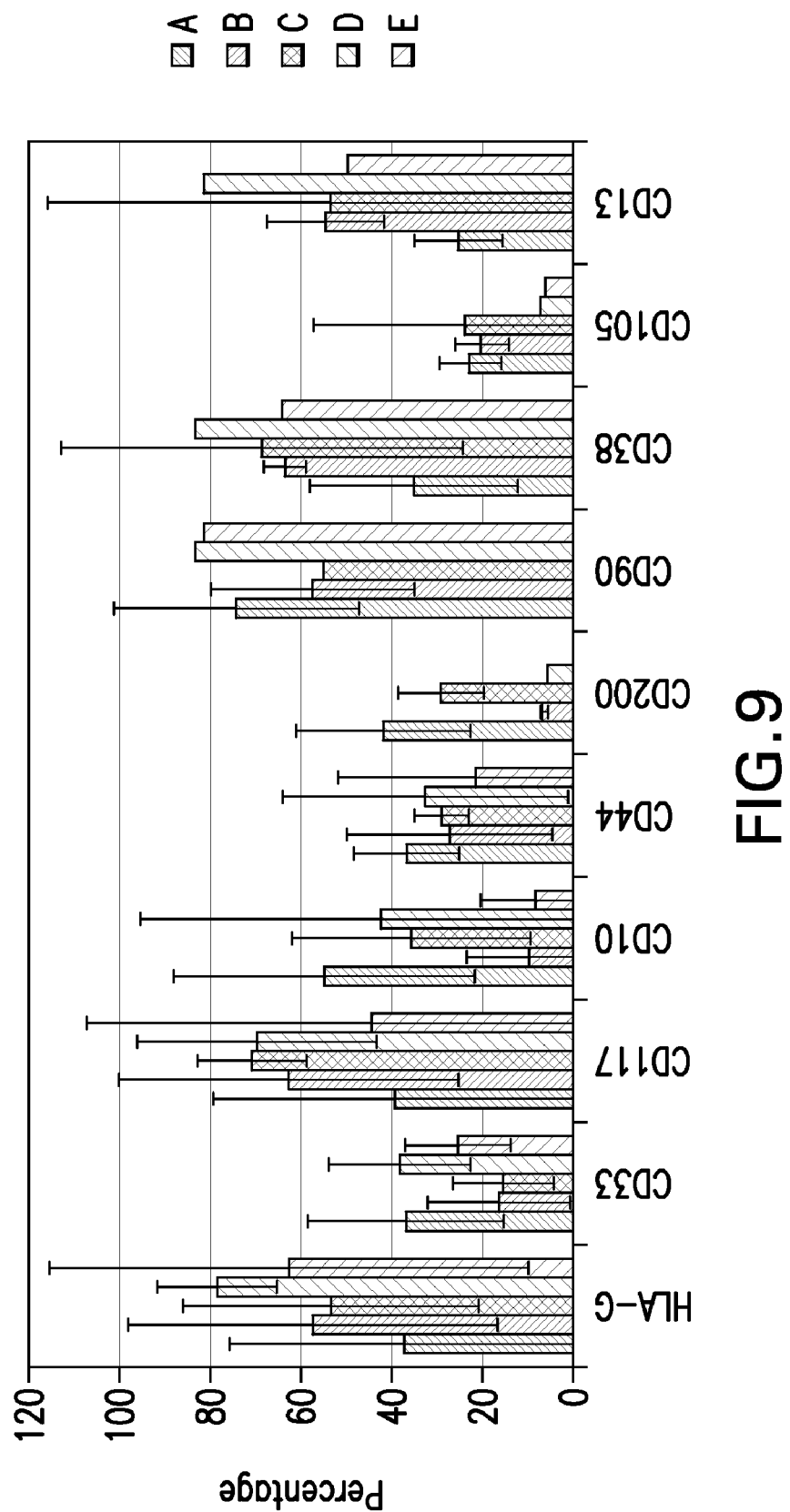

FIG. 9: Average expression of HLA-G, CD10, CD13, CD33, CD38, CD44, CD90, CD105, CD117, CD200 expression in stem cells derived from perfusion (A), amnion (B), chorion (C), amnion-chorion plate (D) or umbilical cord (E).

Figure 10:
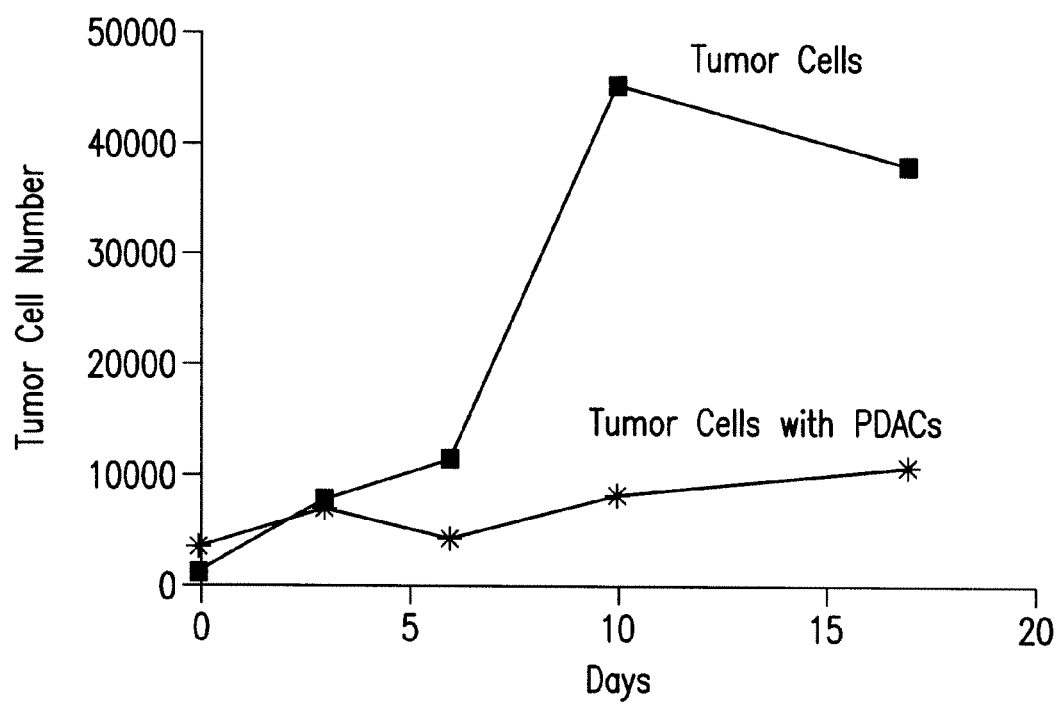

FIG. 10: Placental stem cells and umbilical cord stem cells inhibit lymphoblastoid cell line (LCL) tumor cell growth. LCL were cultured either alone, or with placental stem cells from amnion-chorion (AC) or amniotic membrane (AM), or stem cells from umbilical cord (UC), for 17 days. The ratio of placental stem cells to LCL was 2:1. Large AAD⁻ cells were counted (n=3 for UC)).

Figure 11:
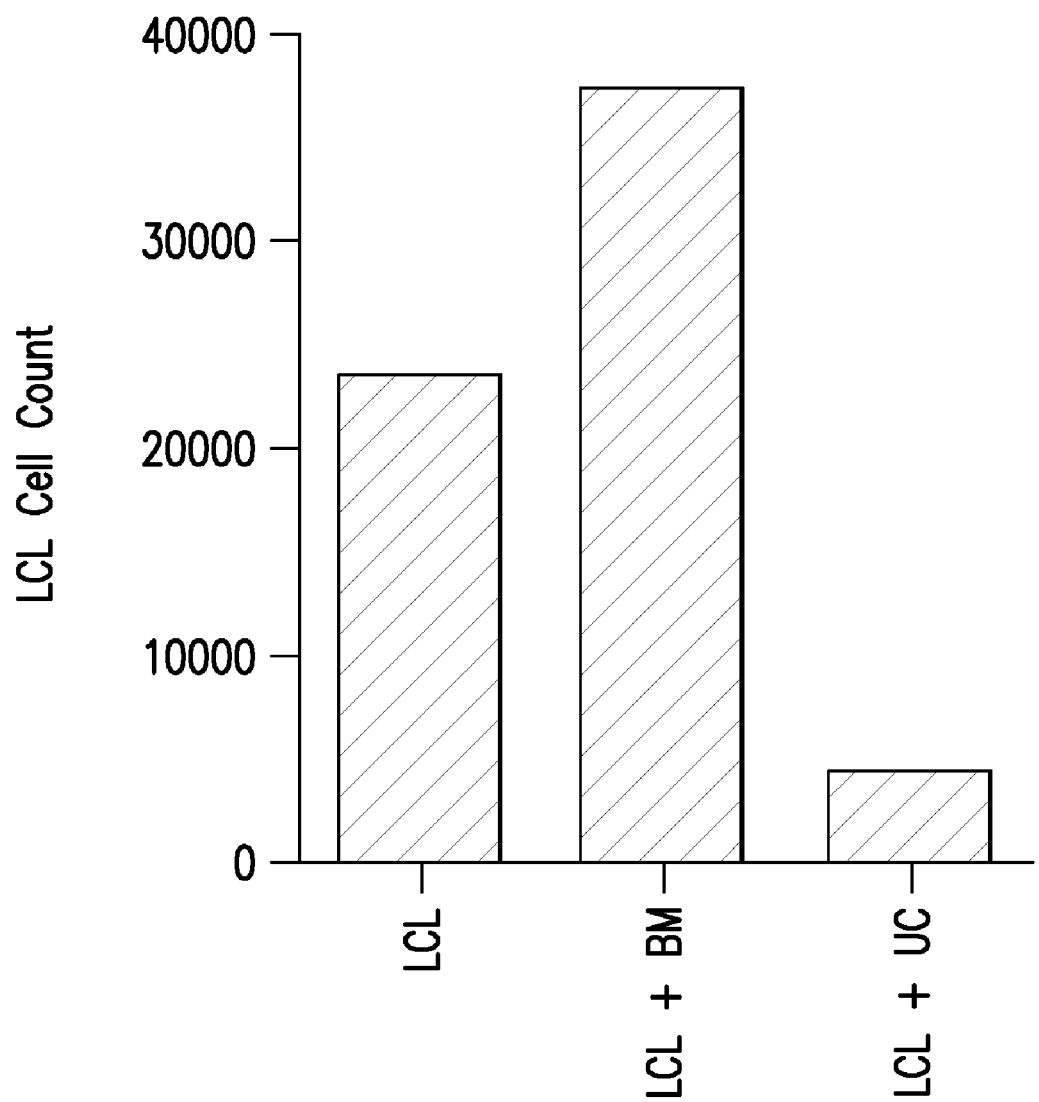

FIG. 11: Placental stem cells kill tumor cells as effectively as do bone marrow-derived mesenchymal stem cells (BM-MSCs). A six-day co-culture of LCL with either BM-MSCs or umbilical cord (UC) stem cells is shown (n=1).

Figure 12:
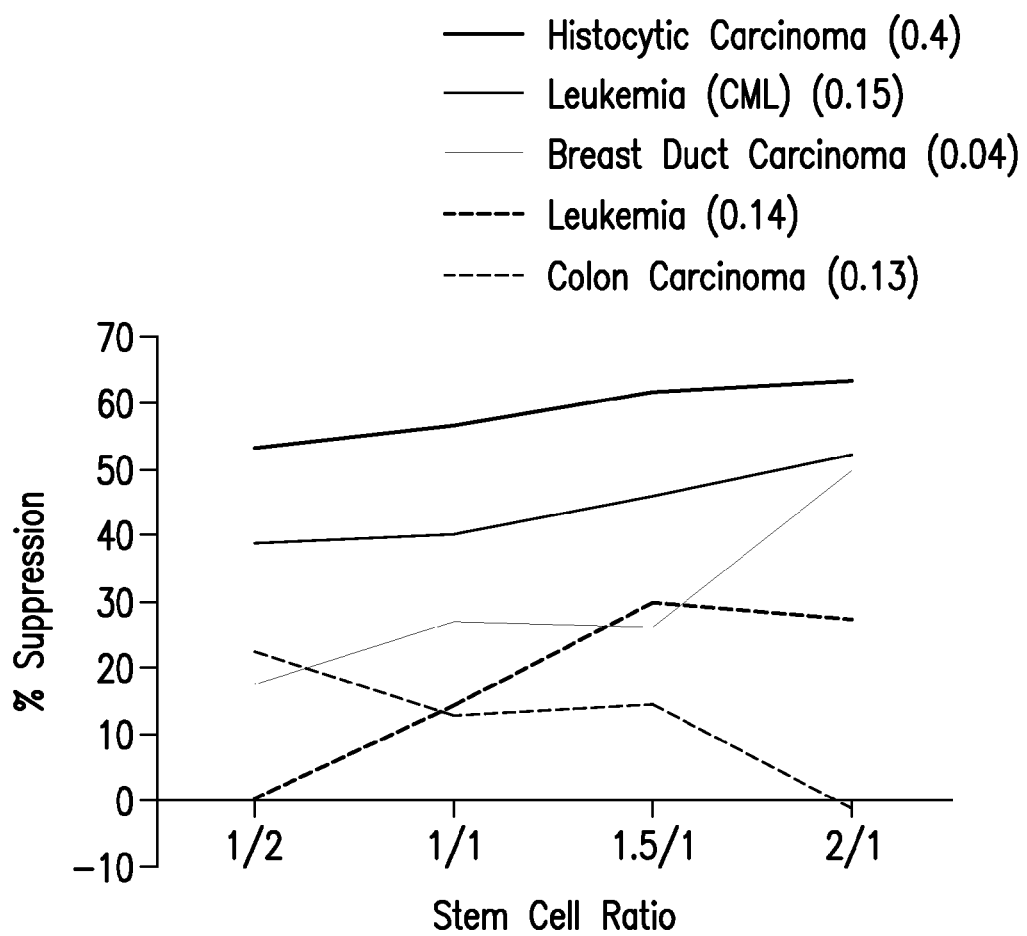

FIG. 12: Dose dependency of placental stem cell tumor suppression. Histiocytic carcinoma, chronic myelogenous leukemia (CML), breast carcinoma, acute lymphocytic leukemia (ALL) and colon carcinoma cells were incubated either alone or with placental stem cells at ratios of 1:2, 1:1, 1.5:1 and 2:1. After co-culture, the number of live 7-AAD⁻ cells was determined. Placental stem cell suppression of the free growing cultures was then calculated. The absolute numbers of free growing tumor cells are given in parentheses following each cell line description in the legend (numbers indicate $10^5$ cells). N=2, except for LCL, n=4.

Figure 13A:
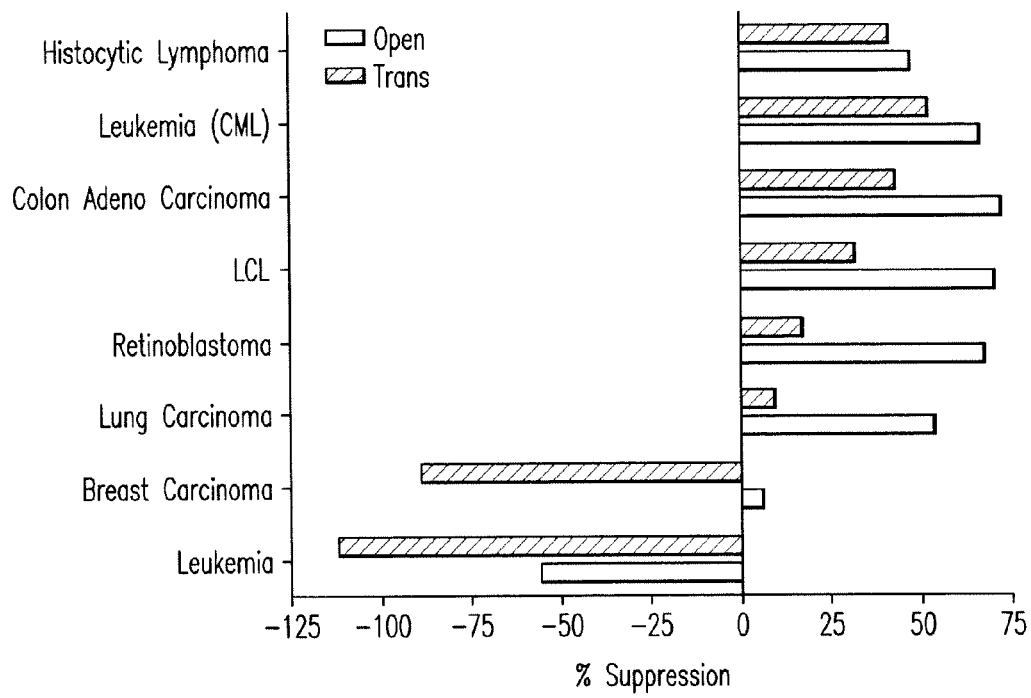
Figure 13B:
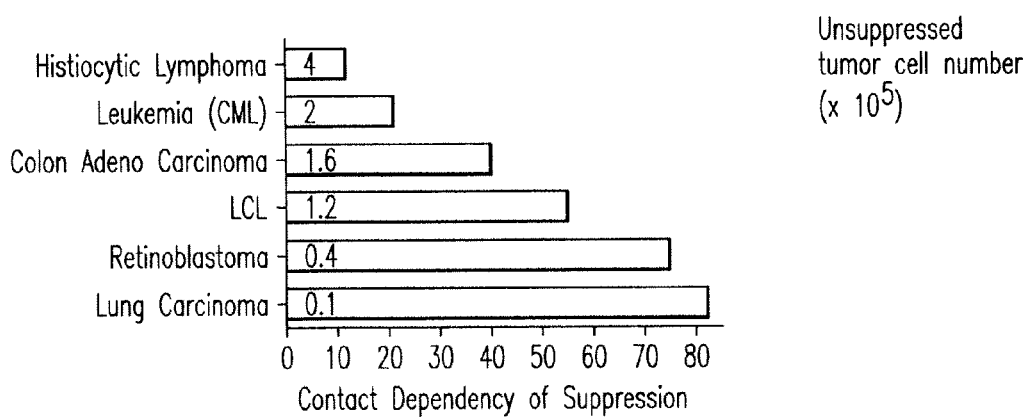

FIGS. 13A and 13B: Suppression and contact dependency of placental stem cell tumor suppression. A: In transwells (black bars) or open wells (A, open bars), histiocytic carcinoma, chronic myelogenous leukemia, breast duct carcinoma, LCL, retinoblastoma, lung carcinoma, breast carcinoma, and ALL cells were incubated alone or with placental stem cells in a 1:1 ratio. After six days, live 7-AAD⁻ cells were counted, and suppression was calculated based on the cell count in the free growing culture (B, numbered inserts). B: From the suppression data, the contact dependency was calculated. Transwell: n=1, except LCL n=2.

FIG. 14: Highly expressed cytokines in supernatants from the experiments the results of which are shown in FIGS. 13A and 13B. Among the 25 cytokines tested, IL-6, IL-8 and MCP-1 are shown for LCL and histiocytic lymphoma. Compare FIGS. 15A and 15B. OP=open wells. TW=transwells.

Figure 15A:
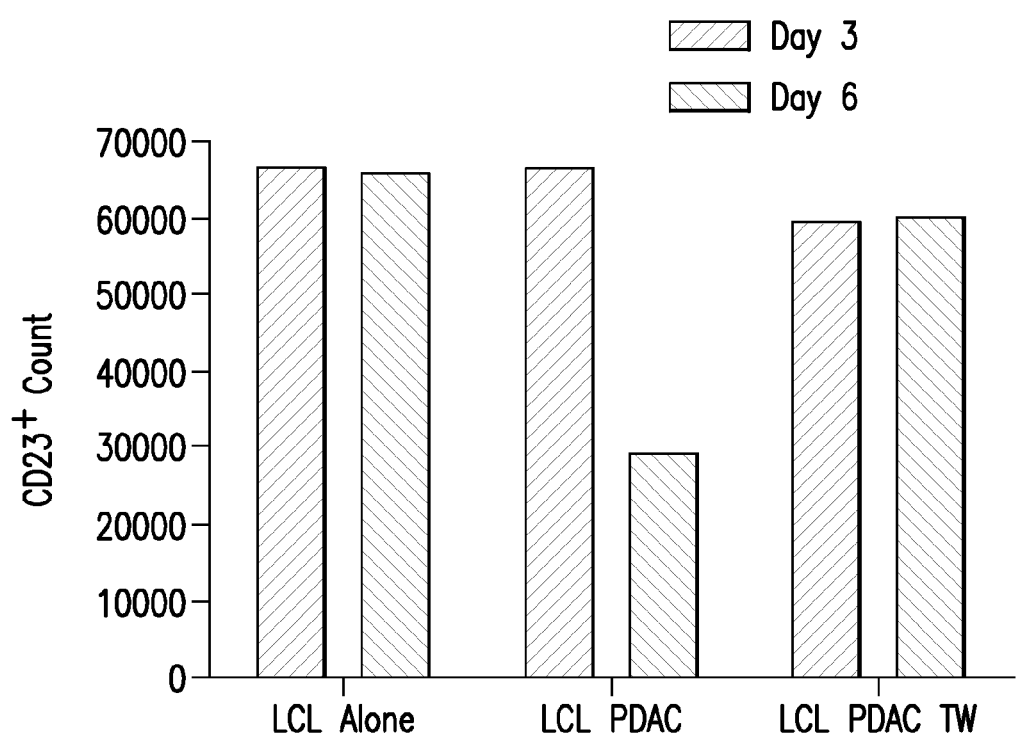
Figure 15B:
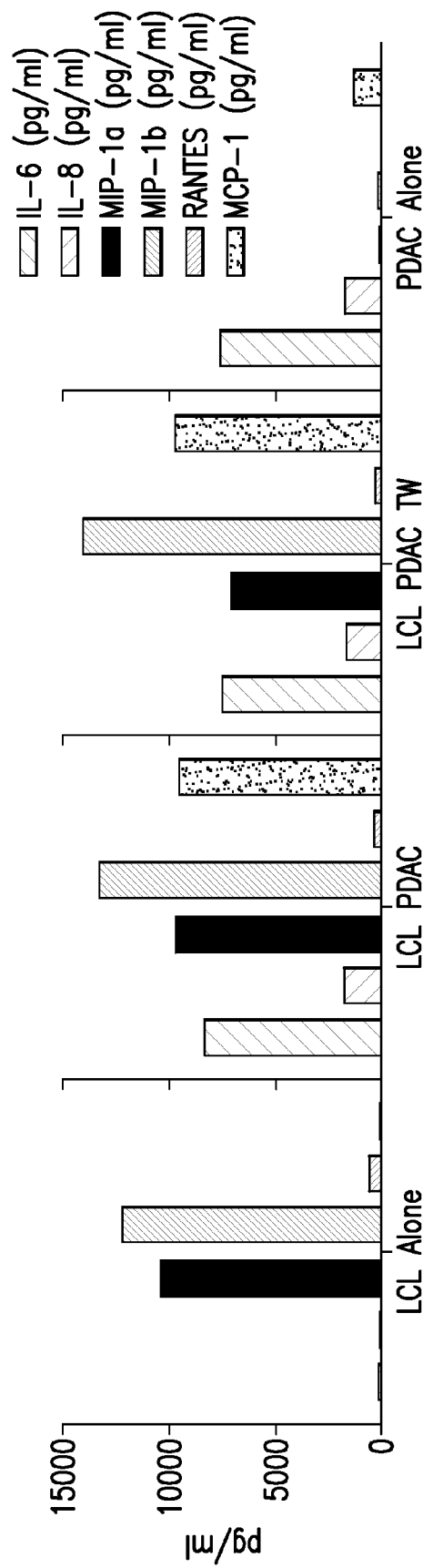

FIGS. 15A and 15B. Cytokine secretion profile of LCL/placental stem cell co-culture. A; LCL were cultured either alone or with placental stem cells in open wells (LCL PDAC) or transwells (LCL PDAC TW). Live CD23⁺ cells were counted on a flow cytometer. B; Supernatants from the experiment in A were analyzed on the Luminex. N=2.

Figure 16A:
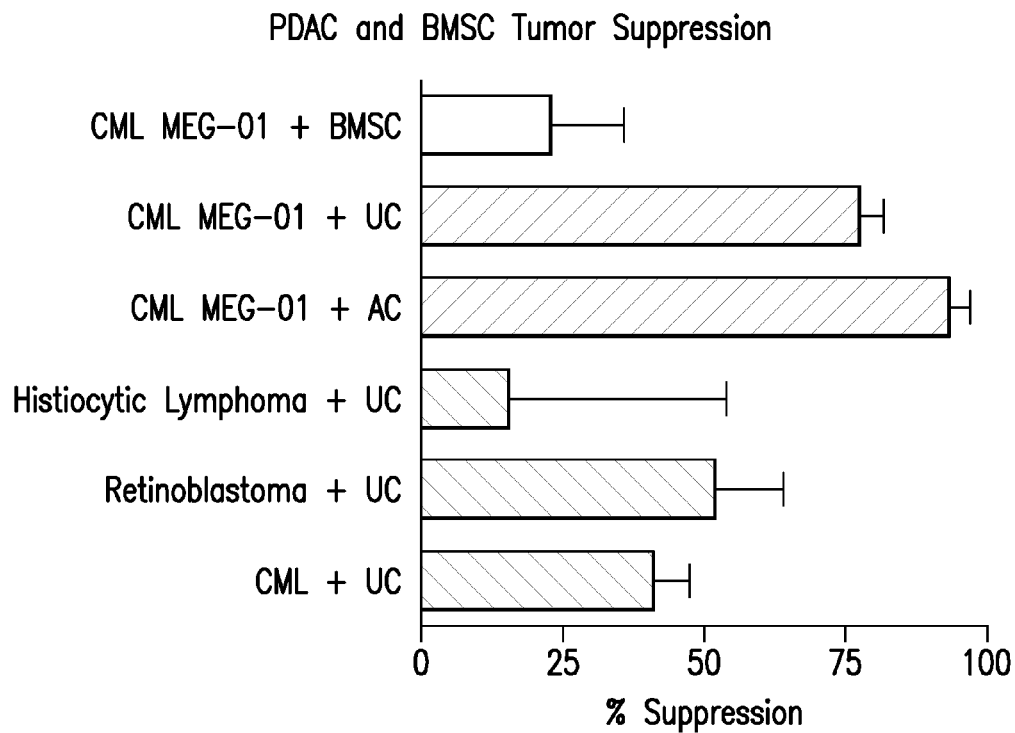
Figure 16B:
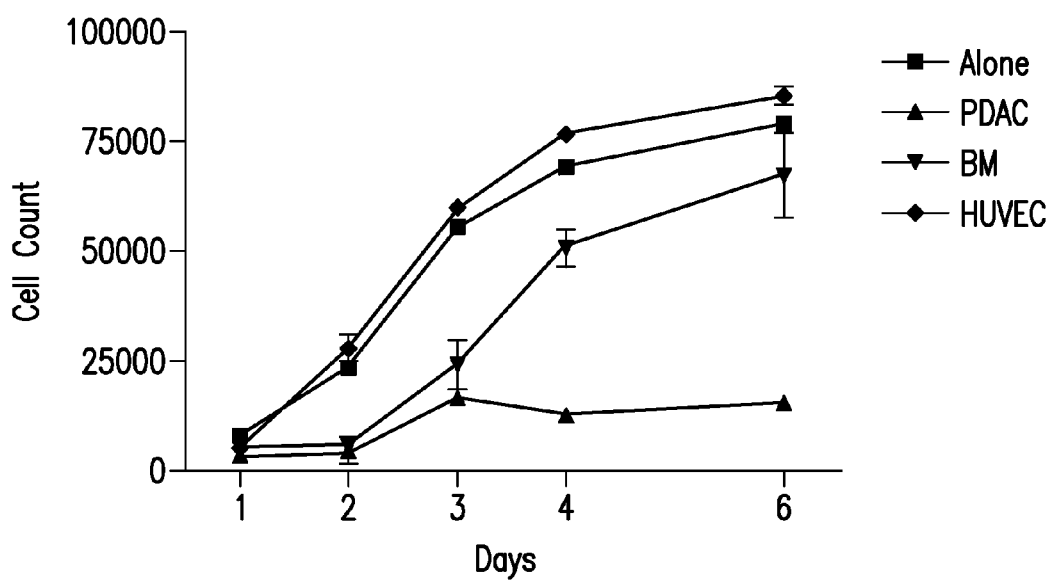

FIGS. 16A and 16B: A: Suppression of tumor cell lines by placental stem cells and bone marrow mesenchymal stem cells (BM-MSC). Megakaryocyte leukemia cell line MEG-01, histiocytic lymphoma, retinoblastoma, and chronic myelogenous leukemia cells were incubated either alone or with umbilical cord stem cells (UC), amnion-chorion placental stem cells (AC), or BM-MSCs. After co-culture for six days, the number of live AAD⁻ cells was determined for each co-culture. B: Time course of tumor cell suppression by placental stem cells. MEG-01 cells were incubated either alone, or co-cultured with human umbilical vein endothelial cells (HUVEC), BM-MSCs, or placental stem cells (PDAC). The number of live (Annexin V⁻, 7-AAD⁻) cells was determined for each culture at 1, 2, 3, 4 and 6 days following initiation of co-culture.

Figure 17:
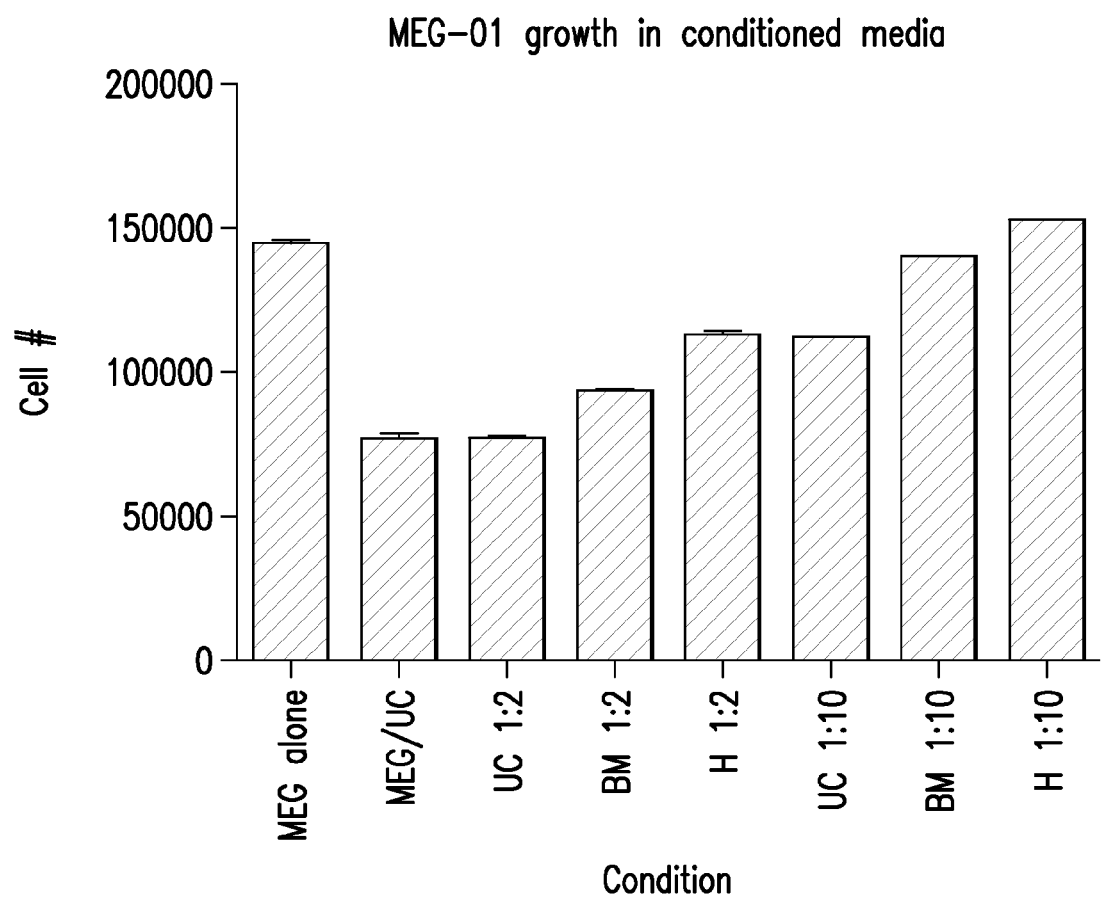
Figure 18A:
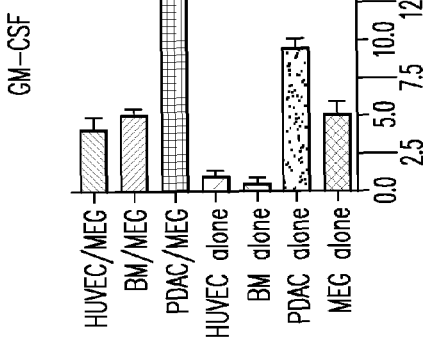
Figure 18B:
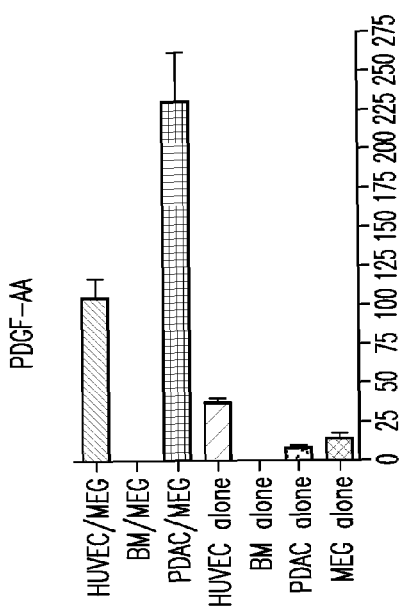
Figure 18C:
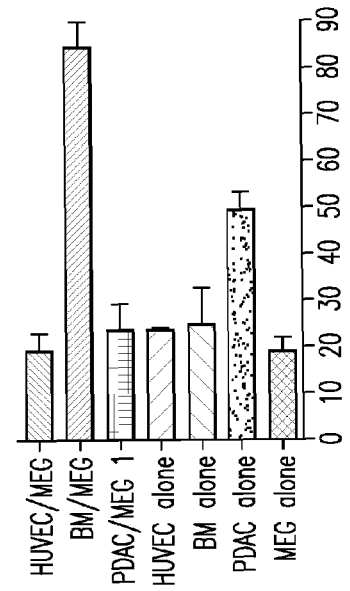
Figure 18D:
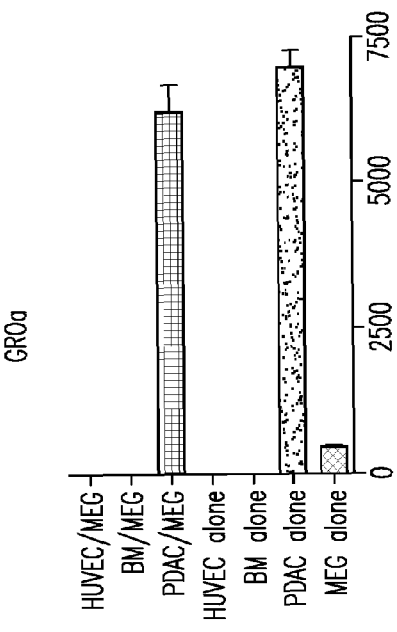

FIG. 17: Contact dependency of placental stem cell tumor suppression of MEG-01 cells. Conditioned media from MEG-01/umbilical cord stem cell co-cultures inhibit megakaryocyte leukemia cell line (MEG-01) tumor cell growth. MEG-01 cells were cultured either alone, directly co-cultured with umbilical cord stem cells (MEG/UC), or cultured in conditioned media (split 1:2 or 1:10) harvested from suppressed MEG-01/umbilical cord stem cell co-cultures (UC), MEG-01/bone marrow mesenchymal stem cell co-cultures (BM), or MEG-01/HUVEC co-cultures (H). After six days of co-culture, the number of live cells (Annexin V⁻, 7-AAD⁻) was determined.

FIG. 18: Cytokine secretion profile in MEG-01/placental stem cell co-culture. MEG-01, placental stem cells (PDAC), BM-MSCs, and HUVEC cells were cultured alone, or co-cultured in the following combinations: MEG-01/HUVEC; MEG-01/BM-MSC; or MEG-01/PDAC. Supernatants from 7-day cultures were harvested and analyzed on the Luminex for platelet-derived growth factor-AA (PDGF-AA), granulocyte-monocyte colony stimulating factor (GM-CSF), growth-related oncogen-alpha (GROα), and leukemia inhibitory factor (LIF) secretion. Amounts shown are in pg/ml.

Figure 19:
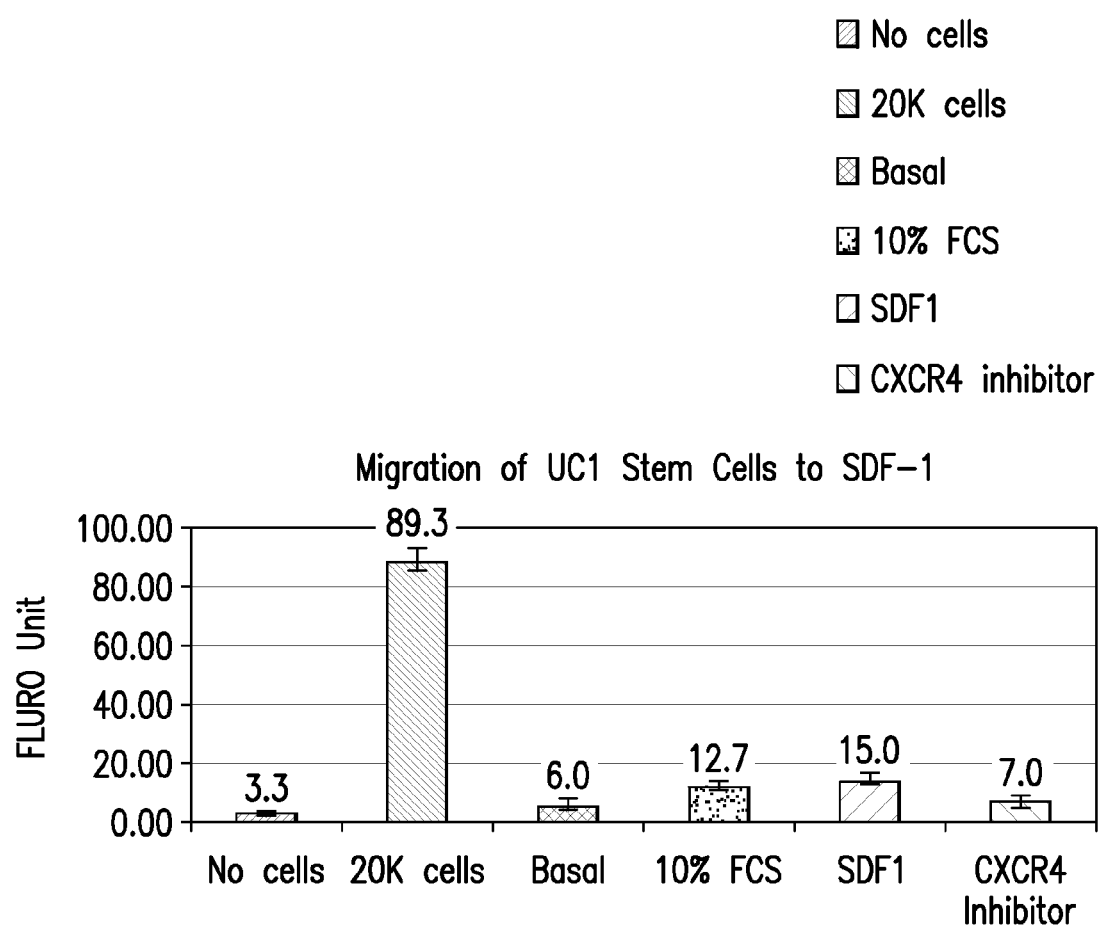

FIG. 19: Migration of umbilical cord stem cells (UC1) in response to stromal cell-derived factor 1 (SDF-1). UC1 placental stem cells were incubated for 24 hours in serum free media only (basal), or in media containing 10% FBS, SDF-1, or SDF-1 plus the CXCR4 inhibitor AMD3100. Following the addition of CYQUANT® GR dye to the cells, fluorescence was measured with a fluorescence plate reader at 480 nm/520 nm.

5. DETAILED DESCRIPTION OF THE INVENTION

5.1 Tumor Cell Suppression Using Placental Stem Cells

The present invention provides for the suppression of the proliferation of tumor cells, and the suppression of the growth of tumors, using placental stem cells. In one embodiment, the invention provides a method of suppressing the proliferation of a tumor cell or plurality of tumor cells, or the growth of a tumor, or the proliferation of a non-solid tumor cell or a plurality of non-solid tumor cells, comprising contacting the tumor cell or cells, or tumor, with a plurality of placental stem cells for a time sufficient for said placental stem cells to detectably suppress proliferation of the tumor cell or cells, or growth of the tumor.

Placental stem cells are, e.g., the placental stem cells described elsewhere herein (see Section 5.2). Placental stem cells used for tumor cell suppression can be derived or obtained from a single placenta or multiple placentas. Placental stem cells used for tumor cell suppression can also be derived from a single species, e.g., the species of the intended recipient or the species of the tumor cells the function of which is to be reduced or suppressed, or can be derived from multiple species. Placental stem cells can be derived from the whole placenta, or from any portion thereof, for example, the amnion, the chorion, the amnion-chorion plate, or the umbilical cord. Placental stem cells derived from any portion of the placenta can be used in the methods of the invention. Placental stem cells can be collected from the placenta, or portion thereof, by any means known to those of skill in the art, e.g., perfusion or enzymatic digestion.

A tumor cell can be any cell exhibiting neoplastic cell growth and proliferation, whether malignant or benign, and includes pre-cancerous as well as cancerous cells. Examples of tumor cells include but are not limited to, carcinoma cells, lymphoma cells, blastoma cells, sarcoma cells, and leukemia cells. More particular examples of tumor cells include breast cancer cells, prostate cancer cells, colon cancer cells, squamous cell cancer cells, small-cell lung cancer cells, non-small cell lung cancer cells, gastrointestinal cancer cells, pancreatic cancer cells, glioblastoma, cervical cancer cells, ovarian cancer cells, liver cancer cells, bladder cancer cells, hepatoma cells, colorectal cancer cells, endometrial carcinoma cells, salivary gland carcinoma cells, kidney cancer cells, liver cancer cells, vulval cancer cells, thyroid cancer cells, hepatic carcinoma cells and various types of head and neck cancer cells. In specific embodiments, the tumor cells are megakaryoblastic lymphoma cells, acute lymphoblast leukemia cells, acute T-cell leukemia cells, histiocytic lymphoma cells, bone marrow acute myelogenous leukemia cells, chronic myelogenous leukemia cells, colon adenocarcinoma cells, retinoblastoma cells or lung carcinoma cells.

The presence of tumor cells in an individual may be determined by performing a biopsy on tissue suspected to be cancerous, or determined from body fluid samples, e.g., from cells purified or isolated from a blood sample. Cancerous cells or tissues can then be characterized using a variety of biological, molecular, morphological, and cytological means. Specifically, biological and molecular markers can be used to assess characteristics such as the type of cell origin (such as an epithelial cell), specific type of cell (such as organ type like breast or prostate), cell growth or cell growth potential, cell growth arrest, and hyperploidy status. These cellular markers are selected from, but not limited to, molecular, biochemical, and biological markers and probes that are used alone or in combination.

"Contacting" in the context of the present invention encompasses bringing the placental stem cells and tumor cells together in vitro, e.g., in a single container (e.g., culture dish, flask, vial, etc.). "Contacting" also encompasses bringing placental stem cells and tumor cells together or in vivo, for example, the same individual (e.g., mammal, for example, mouse, rat, dog, cat, sheep, goat, horse, human, etc.), for example, by providing the placental stem cells to the individual intravenously, by direct injection into the site of a tumor, or the like. In certain embodiments of in vivo contacting, said placental stem cells and said tumor cells are cells in cell culture. In certain other embodiments, said cells are co-cultured in the same physical space, e.g., in the same culture dish or well in a culture dish. In another embodiment, said contacting does not require direct physical contact between said placental stem cells and said tumor cells. For example, said contacting can comprise culturing said placental stem cells and said tumor cells in separate physical spaces, e.g., separate wells in a cell culture dish, wherein the medium in which said placental stem cells and said tumor cells is shared between the placental stem cells and tumor cells. In certain embodiments of in vivo contacting, both the placental stem cells and the tumor cells are exogenous to the individual, that is, neither type of cell originated within the individual. In another embodiment, the tumor cells are tumor cells that arose within the individual through tumorigenesis, i.e., the tumor cells are endogenous to the individual. In a preferred embodiment, the contacting (either in vitro or in vivo) is for a time sufficient, and with a number of placental stem cells sufficient, to cause a detectable suppression of the proliferation of the tumor cell or tumor cells, for a period of time after said contacting. More preferably, in various embodiments, said contacting is sufficient to suppress proliferation of a tumor cell or tumor cells by at least 50%, 60%, 70%, 75%, 80%, 90% or 95%, compared to the immune function in the absence of the placental stem cells, for a period of time after said contacting. Even more preferably, proliferation of the tumor cell or plurality of tumor cells is completely suppressed, such that the tumor cells do not proliferate, or do not proliferate enough to increase the total number of tumor cells, for a period of time after said contacting. In various embodiments, the period of time is 1, 2, 3, 4, 5, 6 or 7 days, or 1, 2, 3, 4, 5, 6, 7, 8, 9, 10 weeks or more.

Suppression of tumor cells, e.g., tumor cells in an individual, can employ as many placental stem cells as are required to effect a detectable suppression of tumor cell proliferation or growth of a tumor. For example, in various embodiments of the method, a plurality of placental stem cells is contacted with a plurality of tumor cells, e.g., tumor cells in an individual, wherein the plurality of placental stem cells comprises about $1 \times 10^5$ placental stem cells, about $1 \times 10^6$ placental stem cells, about $1 \times 10^7$ placental stem cells, about $1 \times 10^8$ placental stem cells, about $1 \times 10^9$ placental stem cells, about $1 \times 10^{10}$ placental stem cells, about $1 \times 10^{11}$ placental stem cells, about $1 \times 10^{12}$ placental stem cells or more.

In other embodiments, the method comprises administering at least about $1 \times 10^5$, at least about $1 \times 10^6$, at least about $1 \times 10^7$, or at least about $1 \times 10^8$ placental stem cells to said individual per kilogram of the individual's body weight. In a specific embodiment, about 1 million placental stem cells is administered to an individual comprising a plurality of tumor cells, per kilogram of the individual's body weight.

In various more specific embodiments, the method comprises administering a number of placental stem cells about one time, two times, three times, four times, five times, or more than five times the number of tumor cells in an individual. Any art known method may be used to determine the number of tumor cells in an individual. Exemplary methods of tumor cell quantification are described in U.S. Pat. Nos. 6,365,362 and 6,645,731; by Méhes et al., *Haematologia* 31(2):97-109 (2001); and Hardingham et al., *Cancer Research* 53:3455-3458 (1993), the contents of which are hereby incorporated by reference in their entireties. In various more specific embodiments, the method comprises administering a number of placental stem cells based on the weight of the individual. For example, the method comprises administering about $1 \times 10^3$ placental stem cells/kg, $5 \times 10^3$ placental stem cells/kg, $1 \times 10^4$ placental stem cells/kg, $5 \times 10^4$ placental stem cells/kg, $1 \times 10^5$ placental stem cells/kg, $5 \times 10^5$ placental stem cells/kg, $1 \times 10^6$ placental stem cells/kg, $5 \times 10^6$ placental stem cells/kg, $1 \times 10^7$ placental stem cells/kg, $5 \times 10^7$ placental stem cells/kg, or $1 \times 10^8$ placental stem cells/kg to said individual. In various more specific embodiments, the method comprises administering at least about $1 \times 10^3$ placental stem cells/kg, at least about $5 \times 10^3$ placental stem cells/kg, at least about $1 \times 10^4$ placental stem cells/kg, at least about $5 \times 10^4$ placental stem cells/kg, at least about $1 \times 10^5$ placental stem cells/kg, at least about $5 \times 10^5$ placental stem cells/kg, at least about $1 \times 10^6$ placental stem cells/kg, at least about $5 \times 10^6$ placental stem cells/kg, at least about $1 \times 10^7$ placental stem cells/kg, at least about $5 \times 10^7$ placental stem cells/kg, or at least about $1 \times 10^8$ placental stem cells/kg to said individual.

In various other more specific embodiments, said placental stem cells have been proliferated in vitro for no more than 30 population doublings, no more than 20 population doublings, no more than 10 population doublings, or no more than 5 population doublings. In another specific embodiment, said placental stem cells have been cryopreserved and thawed prior to said contacting. In other specific embodiments of the method, said placental stem cells suppress said tumor cell proliferation by about 20%, 30%, 40%, 50%, 60%, 70%, 75%, 80%, 90%, or 95%, compared to proliferation of an equivalent number of tumor cells in the absence of said placental stem cells.

Advantageously, the placental stem cells, e.g., placental stem cells from a particular individual or pool of individuals, from particular tissues, or the like, are screened for tumor-suppressive activity prior to use, e.g., to suppress tumor cell growth or proliferation in an individual. In a specific embodiment, therefore, the method of suppressing tumor cell proliferation or growth using placental stem cells comprises screening said placental stem cells in vitro for tumor cell growth suppressive activity prior to administration of said placental stem cells to said individual. In more specific embodiments of the method, said placental stem cells are confirmed to suppress tumor cell proliferation in vitro by, e.g., at least about 20%, 30%, 40%, 50%, 60%, 70%, 75%, 80%, 90%, or 95%, compared to proliferation of an equivalent number of tumor cells in the absence of said placental stem cells, prior to administration to said individual, where the proliferation is measured by the number of cells produced under equivalent conditions over a period of time. The placental stem cells can suppress tumor cells by direct contact, through soluble factors, or both. Thus, in other more specific embodiments of the method, said placental stem cells are confirmed to suppress tumor cell proliferation in vitro in a direct culture assay, in a transwell assay, or more preferably, in both a direct culture assay and a transwell assay, prior to administration to said individual.

The placental stem cells can be screened for suppression of tumor cell proliferation or growth using any tumor cells, but more useful screens are those that replicate, or attempt to replicate, tumor suppression within an affected individual. For example, in another specific embodiment, said placental stem cells are screened in vitro for tumor growth suppressive activity against a tumor cell of the same cell type, e.g. epithelial, squamous, etc., the same tissue of origin, e.g. breast, prostate, etc., or more preferably, both the same cell type and tissue of origin as a tumor cell in the individual to be administered said placental stem cells. In another more specific embodiment, said placental stem cells are screened in vitro for tumor growth suppressive activity against tumor cells obtained from a tumor cell biopsy from said individual, or tumor cells purified or isolated from a blood sample of said individual.

In various more specific embodiments of the method, said placental stem cells are from amnion, chorion, amnion-chorion, or umbilical cord, or from placental perfusate, and are confirmed to suppress tumor cell proliferation in vitro by, e.g., at least about 20%, 30%, 40%, 50%, 60%, 70%, 75%, 80%, 90%, or 95%, compared to proliferation of an equivalent number of tumor cells in the absence of said stem cells, prior to administration to said individual.

For in vivo contacting of placental stem cells and an endogenous tumor, e.g., solid tumor or blood cancer, the placental stem cells can be introduced into the individual in any manner known to those of skill in the art to be effective at introducing live cells to an individual. For example, the placental stem cells can be introduced into the individual by intravenous transfusion, or can be introduced intramuscularly, intraperitoneally, intradermally, and the like. In a preferred embodiment, the placental stem cells are injected into the individual into, at the site of, or at the periphery of the tumor or tumor cells. Cells can also be introduced by the transplantation of, e.g., a natural or man-made matrix, e.g, gelatin, in which the placental stem cells are enmeshed and out of which the cells can grow once transplanted. Non-limiting examples of such matrices are provided in Section 5.6.1.4, below.

Introduction of the placental stem cells into the individual by any of these methods, or others known to those skilled in the art, is sufficient to facilitate contact between said placental stem cells and the tumor cells. Introduction of the placental stem cells into an individual, particularly an individual having endogenous tumor cells, can comprise a single introduction, or multiple introductions over the course of several hours, several days, several weeks, several months, or several years. Each introduction of placental stem cells can comprise a number of stem cells sufficient, in and of itself, to detectably suppress proliferation of a plurality of tumor cells, or can be sufficient in the aggregate. For in vivo administration, the placental stem cells can be formulated as a pharmaceutical composition, as described in Section 5.6.1, below.

The degree of suppression in an in vivo context can be determined in an in vitro assay, for example, by comparing the number of tumor cells produced by a tumor cell or plurality of tumor cells under optimal growth conditions for a period of time compared to a number of tumor cells produced by an equivalent number of tumor cells in contact with placental stem cells for the same amount of time. Proliferation of cells, including tumor cells, can be assessed by any art-known method. For example, cells in culture or in an individual can be sampled at various time points and counted with a hemacytometer or similar device. The tumor cells can be stained with a non-degrading dye designed to be segregated into daughter cells, e.g., staining with bromodeoxyuridine (BrDU), carboxyfluorescein diacetate (CFSE) or Oregon Green 488 carboxylic acid diacetate (Invitrogen), and the degree of staining determined with a cytometer. Placental stem cells suppress tumor cell growth where the tumor cells, in contact with placental stem cells, show a detectably lower amount of the stain per cell (e.g., a detectably lower average amount of stein per cell) than tumor cells not contacted with placental stem cells. The degree of suppression in an in vitro assay can be extrapolated, for a particular number of placental stem cells and a number of tumor cells, to a degree of tumor or tumor cell suppression in an individual.

Suppression of the growth of a tumor can be assessed by any means known in the art for imaging or detecting tumors in vivo. For example, the cells of the tumor can be labeled with a tumor-specific antibody and imaged using, e.g., a PET scan or CAT scan, or can be imaged using X-rays. A determination of suppression of tumor growth can be ascertained, e.g., by visual inspection of an image of the tumor, by determining the intensity of labeling of the tumor, by determining the area of the tumor in an image of the tumor, etc. A determination of suppression of growth of a tumor in vivo can also be made by detecting or noting any elimination of, improvement in, or lessening of worsening of a symptom related to the tumor.

The individual can be a mammal, e.g., a human. In another more specific embodiment, said contacting comprises administering said placental cells to said individual intravenously. In another more specific embodiment, said contacting comprises administering said placental cells to said individual at or adjacent to the site of a tumor.

The placental stem cells can also be administered with one or more second types of stem cells, e.g., mesenchymal stem cells from bone marrow. Such second stem cells can be administered to an individual with placental stem cells in a ratio of, e.g., about 1:10 to about 10:1.

The placental stem cells can also be administered with one or more types of cells that are not stem cells. In a specific embodiment, the placental stem cells are administered to an individual along with a second plurality of cells that are autologous to the individual. In a more specific embodiment, the placental stem cells are co-administered with fibroblasts. In certain embodiments, the fibroblasts are autologous fibroblasts. The fibroblasts can be administered to an individual with placental stem cells in a ratio of, e.g. about 1:10 to about 10:1.

The placental stem cells can also be administered with one or more stem cell chemoattractants. In a specific embodiment, the stem cell chemoattractant is SDF-1.

5.2 Placental Stem Cells and Placental Stem Cell Populations

The methods of suppression of tumor cell proliferation of the present invention use placental stem cells, that is, stem cells obtainable from a placenta or part thereof, that (1) adhere to a tissue culture substrate; (2) have the capacity to differentiate into non-placental cell types; and (3) have, in sufficient numbers, the capacity to detectably suppress the proliferation of a tumor cell or plurality of tumor cells, or detectably suppress the growth of a tumor. Placental stem cells are not derived from blood, e.g., placental blood or umbilical cord blood. The placental stem cells used in the methods and compositions of the present invention have the capacity, and are selected for their capacity, to suppress proliferation of a cancer cell or plurality of cancer cells in vitro or in vivo, or to suppress growth of a tumor in vivo.

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

5.2.1 Physical and Morphological Characteristics

The placental stem cells used in the present invention, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cytoplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

5.2.2 Cell Surface, Molecular and Genetic Markers

Placental stem cells, and populations of placental stem cells, useful in the methods and compositions of the present invention, express a plurality of markers that can be used to identify and/or isolate the stem cells, or populations of cells that comprise the stem cells. The placental stem cells, and stem cell populations of the invention (that is, two or more placental stem cells) include stem cells and stem cell-containing cell populations obtained directly from the placenta, or any part thereof (e.g., amnion, chorion, amnion-chorion plate, placental cotyledons, umbilical cord, and the like). Placental stem cell populations also includes populations of (that is, two or more) placental stem cells in culture, and a population in a container, e.g., a bag. Placental stem cells are not, however, trophoblasts.

Placental stem cells generally express the markers CD73, CD105, CD200, HLA-G, and/or OCT-4, and do not express CD34, CD38, or CD45. Placental stem cells can also express HLA-ABC (MHC-1) and HLA-DR. These markers can be used to identify placental stem cells, and to distinguish placental stem cells from other stem cell types. Because the placental stem cells can express CD73 and CD105, they can have mesenchymal stem cell-like characteristics. However, because the placental stem cells can express CD200 and HLA-G, a fetal-specific marker, they can be distinguished from mesenchymal stem cells, e.g., bone marrow-derived mesenchymal stem cells, which express neither CD200 nor HLA-G. In the same manner, the lack of expression of CD34, CD38 and/or CD45 identifies the placental stem cells as non-hematopoietic stem cells.

In one embodiment, the invention provides an isolated cell population comprising a plurality of placental stem cells that are $CD200^+$, $HLA-G^+$, wherein said stem cells detectably suppress cancer cell proliferation or tumor growth. In a specific embodiment of the isolated populations, said stem cells are also $CD73^+$ and $CD105^+$. In another specific embodiment, said stem cells are also $CD34^-$, $CD38^-$ or $CD45^-$. In a more specific embodiment, said stem cells are also $CD34^-$, $CD38^-$, $CD45^-$, $CD73^+$ and $CD105^+$. In another embodiment, said isolated population produces one or more embryoid-like bodies when cultured under conditions that allow the formation of embryoid-like bodies.

In another embodiment, the invention provides an isolated cell population comprising a plurality of placental stem cells that are $CD73^+$, $CD105^+$, $CD200^+$, wherein said stem cells detectably suppress cancer cell proliferation or tumor growth. In a specific embodiment of said populations, said stem cells are $HLA-G^+$. In another specific embodiment, said stem cells are $CD34^-$, $CD38^-$ or $CD45^-$. In another specific embodiment, said stem cells are $CD34^-$, $CD38^-$ and $CD45^-$. In a more specific embodiment, said stem cells are $CD34^-$, $CD38^-$, $CD45^-$, and $HLA-G^+$. In another specific embodiment, said population of cells produces one or more embryoid-like bodies when cultured under conditions that allow the formation of embryoid-like bodies.

The invention also provides an isolated cell population comprising a plurality of placental stem cells that are $CD200^+$, $OCT-4^+$, wherein said stem cells detectably suppress cancer cell proliferation or tumor growth. In a specific embodiment, said stem cells are $CD73^+$ and $CD105^+$. In another specific embodiment, said stem cells are $HLA-G^+$. In another specific embodiment, said stem cells are $CD34^-$, $CD38^-$ and $CD45^-$. In a more specific embodiment, said stem cells are $CD34^-$, $CD38^-$, $CD45^-$, $CD73^+$, $CD105^+$ and $HLA-G^+$. In another specific embodiment, the population produces one or more embryoid-like bodies when cultured under conditions that allow the formation of embryoid-like bodies.

The invention also provides an isolated cell population comprising a plurality of placental stem cells that are $CD73^+$, $CD105^+$ and $HLA-G^+$, wherein said stem cells detectably suppress T cell proliferation in a mixed lymphocyte reaction (MLR) assay. In a specific embodiment of the above plurality, said stem cells are also $CD34^-$, $CD38^-$ or $CD45^-$. In another specific embodiment, said stem cells are also $CD34^-$, $CD38^-$ and $CD45^-$. In another specific embodiment, said stem cells are also $OCT-4^+$. In another specific embodiment, said stem cells are also CD200$^+$. In a more specific embodiment, said stem cells are also CD34$^-$, CD38$^-$, CD45$^-$, OCT-4$^+$ and CD200$^+$.

The invention also provides an isolated cell population comprising a plurality of tumor cell suppressive placental stem cells that are CD73$^+$, CD105$^+$ stem cells, wherein said plurality forms one or more embryoid-like bodies under conditions that allow formation of embryoid-like bodies, and wherein said stem cells detectably suppress cancer cell proliferation or tumor growth. In a specific embodiment, said stem cells are also CD34$^-$, CD38$^-$ or CD45$^-$. In another specific embodiment, said stem cells are also CD34$^-$, CD38$^-$ and CD45$^-$. In another specific embodiment, said stem cells are also OCT-4$^+$. In a more specific embodiment, said stem cells are also OCT-4$^+$, CD34$^-$, CD38$^-$ and CD45$^-$.

The invention also provides an isolated cell population comprising a plurality of placental stem cells that are OCT-4$^+$ stem cells, wherein said population forms one or more embryoid-like bodies when cultured under conditions that allow the formation of embryoid-like bodies, and wherein said stem cells have been identified as detectably suppressing cancer cell proliferation or tumor growth.

In various embodiments, at least 10%, at least 20%, at least 30%, at least 40%, at least 50% at least 60%, at least 70%, at least 80%, at least 90%, or at least 95% of said isolated placental cells are OCT4$^+$ stem cells. In a specific embodiment of the above populations, said stem cells are CD73$^+$ and CD105$^+$. In another specific embodiment, said stem cells are CD34$^-$, CD38$^-$, or CD45$^-$. In another specific embodiment, said stem cells are CD200$^+$. In a more specific embodiment, said stem cells are CD73$^+$, CD105$^+$, CD200$^+$, CD34$^-$, CD38$^-$, and CD45$^-$. In another specific embodiment, said population has been expanded, for example, passaged at least once, at least three times, at least five times, at least 10 times, at least 15 times, or at least 20 times.

In any of the above embodiments, the method can additionally comprise selecting placental cells that express ABC-p (a placenta-specific ABC transporter protein; see, e.g., Allikmets et al., *Cancer Res.* 58(23):5337-9 (1998)). The method can also comprise selecting cells exhibiting at least one characteristic specific to, e.g., a mesenchymal stem cell, for example, expression of CD29, expression of CD44, expression of CD90, or expression of a combination of the foregoing.

In another embodiment, the invention provides an isolated cell population comprising a plurality of tumor cell-suppressive placental stem cells that are CD29$^+$, CD44$^+$, CD73$^+$, CD90$^+$, CD105$^+$, CD200$^+$, CD34$^-$ and CD133$^-$.

In a specific embodiment of the above-mentioned placental stem cells, the placental stem cells constitutively secrete IL-6, IL-8 and monocyte chemoattractant protein (MCP-1).

Each of the above-referenced pluralities of placental stem cells can comprise placental stem cells obtained and isolated directly from a mammalian placenta, or placental stem cells that have been cultured and passaged at least 1, 2, 3, 4, 5, 6, 7, 8, 9, 10, 12, 14, 16, 18, 20, 25, 30 or more times, or a combination thereof.

The tumor cell suppressive pluralities of placental stem cells described above can comprise about, at least, or no more than, 1×10$^5$, 5×10$^5$, 1×10$^6$, 5×10$^6$, 1×10$^7$, 5×10$^7$, 1×10$^8$, 5×10$^8$, 1×10$^9$, 5×10$^9$, 1×10$^{10}$, 5×10$^{10}$, 1×10$^{11}$ or more placental stem cells.

5.2.3 Selecting and Producing Placental Stem Cell Populations

In another embodiment, the invention also provides a method of selecting a plurality of placental stem cells from a plurality of placental cells, comprising selecting a population of placental cells wherein at least 10%, at least 20%, at least 30%, at least 40%, at least 50%, at least 60%, at least 70%, at least 80%, at least 90%, or at least 95% of said cells are CD200$^+$, HLA-G$^+$ placental stem cells, and wherein said placental stem cells detectably suppress cancer cell proliferation or tumor growth. In a specific embodiment, said selecting comprises selecting stem cells that are also CD73$^+$ and CD105$^+$. In another specific embodiment, said selecting comprises selecting stem cells that are also CD34$^-$, CD38$^-$ or CD45$^-$. In another specific embodiment, said selecting comprises selecting placental stem cells that are also CD34$^-$, CD38$^-$, CD45$^-$, CD73$^+$ and CD105$^+$. In another specific embodiment, said selecting also comprises selecting a plurality of placental stem cells that forms one or more embryoid-like bodies when cultured under conditions that allow the formation of embryoid-like bodies.

In another embodiment, the invention also provides a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$, CD200$^+$ placental stem cells, and wherein said placental stem cells detectably suppress cancer cell proliferation or tumor growth. In a specific embodiment, said selecting comprises selecting stem cells that are also HLA-G$^+$. In another specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, and HLA-G$^+$. In another specific embodiment, said selecting additionally comprises selecting a population of placental cells that produces one or more embryoid-like bodies when the population is cultured under conditions that allow the formation of embryoid-like bodies.

In another embodiment, the invention also provides a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD200$^+$, OCT-4$^+$ placental stem cells, and wherein said placental stem cells detectably suppress cancer cell proliferation or tumor growth. In a specific embodiment, said selecting comprises selecting placental stem cells that are also CD73$^+$ and CD105$^+$. In another specific embodiment, said selecting comprises selecting placental stem cells that are also HLA-G$^+$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, CD73$^+$, CD105$^+$ and HLA-G$^+$.

In another embodiment, the invention also provides a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73$^+$, CD105$^+$ and HLA-G+placental stem cells, and wherein said placental stem cells detectably suppresses T cell proliferation in a mixed lymphocyte reaction (MLR) assay. In a specific embodiment, said selecting comprises selecting placental stem cells that are also CD34$^-$, CD38$^-$ or CD45$^-$. In another specific embodiment, said selecting comprises selecting placental stem cells that are also CD34⁻, CD38⁻ and CD45⁻. In another specific embodiment, said selecting comprises selecting placental stem cells that are also CD200⁺. In another specific embodiment, said selecting comprises selecting placental stem cells that are also CD34⁻, CD38⁻, CD45⁻, OCT-4⁺ and CD200⁺.

In another embodiment, the invention also provides a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said cells are CD73⁺, CD105⁺ placental stem cells, and wherein said plurality forms one or more embryoid-like bodies under conditions that allow formation of embryoid-like bodies, and wherein said stem cells detectably suppress cancer cell proliferation or tumor growth. In a specific embodiment, said selecting comprises selecting placental stem cells that are also CD34⁻, CD38⁻ or CD45⁻. In another specific embodiment, said selecting comprises selecting placental stem cells that are also CD34⁻, CD38⁻ and CD45⁻. In another specific embodiment, said selecting comprises selecting placental stem cells that are also OCT-4⁺. In a more specific embodiment, said selecting comprises selecting placental stem cells that are also OCT-4⁺, CD34⁻, CD38⁻ and CD45⁻.

In another embodiment, the invention also provides a method of selecting a plurality of placental stem cells from a plurality of placental cells, comprising selecting a plurality of placental cells wherein at least 10%, at least 20%, at least 30%, at least 40%, at least 50% at least 60%, at least 70%, at least 80%, at least 90%, or at least 95% of said isolated placental cells are OCT4⁺ stem cells, and wherein said plurality forms one or more embryoid-like bodies under conditions that allow formation of embryoid-like bodies, and wherein said stem cells detectably suppress cancer cell proliferation or tumor growth. In a specific embodiment, said selecting comprises selecting placental stem cells that are also CD73⁺ and CD105⁺. In another specific embodiment, said selecting comprises selecting placental stem cells that are also CD34⁻, CD38⁻, or CD45⁻. In another specific embodiment, said selecting comprises selecting placental stem cells that are also CD200⁺. In a more specific embodiment, said selecting comprises selecting placental stem cells that are also CD73⁺, CD105⁺, CD200⁺, CD34⁻, CD38⁻, and CD45⁻.

The invention also provides methods of producing populations, of placental stem cells that can suppress the proliferation of tumor cells. For example, the invention provides a method of producing a cell population, comprising selecting any of the pluralities of placental stem cells described above, and isolating the plurality of placental stem cells from other cells, e.g., other placental cells. In a specific embodiment, the invention provides a method of producing a cell population comprising selecting placental cells, wherein said placental cells (a) adhere to a substrate, (b) express CD200 and HLA-G, or express CD73, CD105, and CD200, or express CD200 and OCT-4, or express CD73, CD105, and HLA-G, or express CD73 and CD105, and facilitate the formation of one or more embryoid-like bodies in a population of placental cells that comprise the stem cell, when said population is cultured under conditions that allow formation of embryoid-like bodies, or express OCT-4, and facilitate the formation of one or more embryoid-like bodies in a population of placental cells that comprise the stem cell, when said population is cultured under conditions that allow formation of embryoid-like bodies; and (c) detectably suppress cancer cell proliferation or tumor growth; and isolating said placental cells from other cells to form a cell population.

In a more specific embodiment, the invention provides a method of producing a cell population comprising selecting placental stem cells that (a) adhere to a substrate, (b) express CD200 and HLA-G, and (c) detectably suppress cancer cell proliferation or tumor growth; and isolating said placental stem cells from other cells to form a cell population. In another specific embodiment, the invention provides a method of producing a cell population comprising selecting placental stem cells that (a) adhere to a substrate, (b) express CD73, CD105, and CD200, and (c) detectably suppress cancer cell proliferation or tumor growth; and isolating said placental stem cells from other cells to form a cell population. In another specific embodiment, the invention provides a method of producing a cell population comprising selecting placental stem cells that (a) adhere to a substrate, (b) express CD200 and OCT-4, and (c) detectably suppress cancer cell proliferation or tumor growth; and isolating said placental stem cells from other cells to form a cell population. In another specific embodiment, the invention provides a method of producing a cell population comprising selecting placental stem cells that (a) adhere to a substrate, (b) express CD73 and CD105, (c) form embryoid-like bodies when cultured under conditions allowing the formation of embryoid-like bodies, and (d) detectably suppress cancer cell proliferation or tumor growth; and isolating said placental stem cells from other cells to form a cell population. In another specific embodiment, the invention provides a method of producing a cell population comprising selecting placental stem cells that (a) adhere to a substrate, (b) express CD73, CD105, and HLA-G, and (c) detectably suppress CD4+ or CD8+ T cell proliferation in an MLR; and isolating said placental stem cells from other cells to form a cell population. A method of producing a cell population comprising selecting placental stem cells that (a) adhere to a substrate, (b) express OCT-4, (c) form embryoid-like bodies when cultured under conditions allowing the formation of embryoid-like bodies, and (d) detectably suppress cancer cell proliferation or tumor growth; and isolating said placental stem cells from other cells to form a cell population.

For the above methods of selecting placental stem cell populations, the selection can comprise determining whether a sample of said placental stem cells suppresses cancer cell proliferation, or suppresses the growth of a tumor, and selecting the population of placental stem cells if the sample of placental stem cells detectably suppresses cancer cell proliferation or tumor growth.

5.2.4 Growth in Culture

The growth of the placental stem cells described herein, as for any mammalian cell, depends in part upon the particular medium selected for growth. Under optimum conditions, placental stem cells typically double in number in 3-5 days. During culture, the placental stem cells of the invention adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells of the invention, when cultured under appropriate conditions, form embryoid-like bodies, that is, three-dimensional clusters of cells that grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental stem cells thus facilitate the growth of one or more embryoid-like bodies in a population of placental cells that comprise the adherent placental stem cells. Without wishing to be bound by theory, the cells of the embryoid-like bodies are thought to grow on the adherent placental stem cells much as embryonic stem cells grow on a feeder layer of cells. Mesenchymal stem cells, e.g., bone marrow-derived mesenchymal stem cells, do not develop embryoid-like bodies in culture.

5.3 Methods of Obtaining Placental Stem Cells

5.3.1 Stem Cell Collection Composition

The present invention further provides methods of collecting and isolating placental stem cells. Generally, stem cells are obtained from a mammalian placenta using a physiologically-acceptable solution, e.g., a stem cell collection composition. A stem cell collection composition is described in detail in related U.S. Provisional Application No. 60/754,969, entitled "Improved Composition for Collecting and Preserving Placental Stem Cells and Methods of Using the Composition" filed on Dec. 29, 2005.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa*, *Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.3.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental stem cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.3.3 Physical Disruption and Enzymatic Digestion of Placental Tissue

In one embodiment, stem cells are collected from a mammalian placenta by physical disruption, e.g., enzymatic digestion, of the organ. For example, the placenta, or a portion thereof, may be, e.g., crushed, sheared, minced, diced, chopped, macerated or the like, while in contact with the stem cell collection composition of the invention, and the tissue subsequently digested with one or more enzymes. The placenta, or a portion thereof, may also be physically disrupted and digested with one or more enzymes, and the resulting material then immersed in, or mixed into, the stem cell collection composition of the invention. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The placenta can be dissected into components prior to physical disruption and/or enzymatic digestion and stem cell recovery. For example, placental stem cells can be obtained from the amniotic membrane, chorion, placental cotyledons, or any combination thereof. Umbilical cord stem cells can also be used in the methods of the invention. In a specific embodiment, placental stem cells are obtained from placental tissue comprising amnion and chorion. In another specific embodiment, placental stem cells are obtained from umbilical cord. Typically, placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred stem cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

It will be appreciated that where an entire placenta, or portion of a placenta comprising both fetal and maternal cells (for example, where the portion of the placenta comprises the chorion or cotyledons), the placental stem cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

5.3.4 Placental Perfusion

Placental stem cells can also be obtained by perfusion of the mammalian placenta. Methods of perfusing mammalian placenta to obtain stem cells are disclosed, e.g., in Hariri, U.S. Pat. No. 7,045,148, and in related U.S. Provisional Application No. 60/754,969, entitled "Improved Composition for Collecting and Preserving Placental Stem Cells and Methods of Using the Composition" filed on Dec. 29, 2005.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition of the invention, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental stem cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where, according to the methods of the invention, they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion according to the methods of the invention results in the collection of significantly more placental stem cells than the number obtainable from a mammalian placenta not perfused with said solution, and not otherwise treated to obtain stem cells (e.g., by tissue disruption, e.g., enzymatic digestion). In this context, "significantly more" means at least 10% more. Perfusion according to the methods of the invention yields significantly more placental stem cells than, e.g., the number of placental stem cells obtainable from culture medium in which a placenta, or portion thereof, has been cultured.

Stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition of the invention.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

5.3.5 Isolation Sorting, and Characterization of Placental Stem Cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using LYMPHOPREP® (Nycomed Pharma, Oslo, Norway) according to the manufacturer's recommended procedure.

As used herein, "isolating" placental stem cells means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about 5-10×10$^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is CD34$^+$. Likewise, if a cell produces enough OCT-4 RNA to be detectable by RT-PCR, or significantly more OCT-4 RNA than an adult cell, the cell is OCT-4$^+$ Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers CD34, CD38, CD44, CD45, CD73, CD105, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; CD34$^-$ cells are retained, and cells that are CD200$^+$HLA-G$^+$, are separated from all other CD34$^-$ cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are CD200$^+$, HLA-G$^+$, CD73$^+$, CD105$^+$, CD34$^-$, CD38$^-$ and CD45$^-$ are isolated from other placental cells for further use.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4$^+$ placental cells that produce one or more embryoid-like bodies in culture are isolated from other placental cells.

In another embodiment, placental stem cells can be identified and characterized by a colony forming unit assay. Colony forming unit assays are commonly known in the art, such as MESEN CULT™ medium (Stem Cell Technologies, Inc., Vancouver British Columbia)

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.4 Culture of Placental Stem Cells

5.4.1 Culture Media

Isolated placental stem cells, or placental stem cell population, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GLUTAMAX™ and gentamicin; DMEM comprising 10% FBS, GLUTAMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMIEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1. (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

5.4.2 Expansion and Proliferation of Placental Stem Cells

Once an isolated placental stem cell, or isolated population of stem cells (e.g., a stem cell or population of stem cells separated from at least 50% of the placental cells with which the stem cell or population of stem cells is normally associated in vivo), the stem cell or population of stem cells can be proliferated and expanded in vitro. For example, a population of placental stem cells can be cultured in tissue culture containers, e.g., dishes, flasks, multiwell plates, or the like, for a sufficient time for the stem cells to proliferate to 70-90% confluence, that is, until the stem cells and their progeny occupy 70-90% of the culturing surface area of the tissue culture container.

Placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells preferably are grown under low oxidative stress (e.g., with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium. Typically, the new medium is the same type of medium from which the stem cells were removed. The invention encompasses populations of placental stem cells that have been passaged at least 1, 2, 3, 4, 5, 6, 7, 8, 9, 10, 12, 14, 16, 18, or 20 times, or more.

5.4.3 Placental Stem Cell Populations

The invention provides populations of placental stem cells. Placental stem cell population can be isolated directly from one or more placentas; that is, the placental stem cell population can be a population of placental cells, comprising placental stem cells, obtained from, or contained within, perfusate, or obtained from, or contained within, digestate (that is, the collection of cells obtained by enzymatic digestion of a placenta or part thereof). Isolated placental stem cells of the invention can also be cultured and expanded to produce placental stem cell populations. Populations of placental cells comprising placental stem cells can also be cultured and expanded to produce placental stem cell populations.

Placental stem cell populations of the invention comprise placental stem cells, for example, placental stem cells as described herein. In various embodiments, at least 10%, 20%, 30%, 40%, 50%, 60%, 70%, 80%, 90%, 95%, or 99% of the cells in an isolated placental stem cell population are placental stem cells. That is, a placental stem cell population can comprise, e.g., as much as 1%, 5%, 10%, 20%, 30%, 40%, 50%, 60%, 70%, 80%, 90% non-stem cells.

In the embodiments herein, the substrate can be any surface on which culture and/or selection of cells, e.g., placental stem cells, can be accomplished. Typically, the substrate is plastic, e.g., tissue culture dish or multiwell plate plastic. Tissue culture plastic can be coated with a biomolecule, e.g., laminin or fibronectin.

Cells, e.g., placental stem cells, can be selected for a placental stem cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental stem cell population can comprise placental cells that are not stem cells, or cells that are not placental cells.

Isolated placental stem cell populations can be combined with one or more populations of non-stem cells or non-placental cells. For example, an isolated population of placental stem cells can be combined with blood (e.g., placental blood or umbilical cord blood), blood-derived stem cells (e.g., stem cells derived from placental blood or umbilical cord blood), populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. Cells in an isolated placental stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental stem cell population can be combined with a plurality of cells of a plurality of cell types, as well.

In one, an isolated population of placental stem cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

5.5 Preservation of Placental Stem Cells

Placental stem cells can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Composition for Collecting and Preserving Placental Stem Cells and Methods of Using the Composition" filed on Dec. 25, 2005. In one embodiment, the invention provides a method of preserving a population of stem cells comprising contacting said population of stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said population of stem cells. In another more specific embodiment, said contacting is performed during freezing and thawing of said population of stem cells.

In another embodiment, the invention provides a method of preserving a population of placental stem cells comprising contacting said population of stem cells with an inhibitor of apoptosis and an organ-preserving compound, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stem et al., U.S. Pat. No. 5,552,267. In another embodiment, said organ-preserving compound is hydroxyethyl starch, lactobionic acid, raffinose, or a combination thereof. In another embodiment, the stem cell collection composition additionally comprises an oxygen-carrying perfluorocarbon, either in two phases or as an emulsion.

In another embodiment of the method, placental stem cells are contacted with a stem cell collection composition comprising an apoptosis inhibitor and oxygen-carrying perfluorocarbon, organ-preserving compound, or combination thereof, during perfusion. In another embodiment, said stem cells are contacted during a process of tissue disruption, e.g., enzymatic digestion. In another embodiment, placental stem cells are contacted with said stem cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of stem cells is exposed to said hypoxic condition for less than two hours during said preservation. In another more specific embodiment, said population of stem cells is exposed to said hypoxic condition for less than one hour, or less than thirty minutes, or is not exposed to a hypoxic condition, during collection, enrichment or isolation. In another specific embodiment, said population of stem cells is not exposed to shear stress during collection, enrichment or isolation.

The placental stem cells of the invention can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. Placental stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.6 Uses of Placental Stem Cells

5.6.1 Compositions Comprising Placental Stem Cells

The methods of tumor cell suppression of the present invention can use compositions comprising placental stem cells, or biomolecules therefrom. In the same manner, the pluralities and populations of placental stem cells of the present invention can be combined with any physiologically-acceptable or medically-acceptable compound, composition or device for use in, e.g., research or therapeutics.

5.6.1.1 Cryopreserved Placental Stem Cells

The tumor cell suppressive placental stem cell populations of the invention can be preserved, for example, cryopreserved for later use. Methods for cryopreservation of cells, such as stem cells, are well known in the art. Placental stem cell populations can be prepared in a form that is easily administrable to an individual. For example, the invention provides a placental stem cell population that is contained within a container that is suitable for medical use. Such a container can be, for example, a sterile plastic bag, flask, jar, or other container from which the placental stem cell population can be easily dispensed. For example, the container can be a blood bag or other plastic, medically-acceptable bag suitable for the intravenous administration of a liquid to a recipient. The container is preferably one that allows for cryopreservation of the combined stem cell population.

Cryopreserved tumor cell suppressive placental stem cell populations can comprise placental stem cells derived from a single donor, or from multiple donors. The placental stem cell population can be completely HLA-matched to an intended recipient, or partially or completely HLA-mismatched.

Thus, in one embodiment, the invention provides a composition comprising an tumor cell suppressive placental stem cell population in a container. In a specific embodiment, the stem cell population is cryopreserved. In another specific embodiment, the container is a bag, flask, or jar. In more specific embodiment, said bag is a sterile plastic bag. In a more specific embodiment, said bag is suitable for, allows or facilitates intravenous administration of said placental stem cell population. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cell population is contained within a physiologically-acceptable aqueous solution. In a more specific embodiment, said physiologically-acceptable aqueous solution is a 0.9% NaCl solution. In another specific embodiment, said placental stem cell population comprises placental cells that are HLA-matched to a recipient of said stem cell population. In another specific embodiment, said combined stem cell population comprises placental cells that are at least partially HLA-mismatched to a recipient of said stem cell population. In another specific embodiment, said placental stem cells are derived from a plurality of donors.

5.6.1.2 Pharmaceutical Compositions

Tumor cell suppressive populations of placental stem cells, or populations of cells comprising placental stem cells, can be formulated into pharmaceutical compositions for use in vivo. Such pharmaceutical compositions comprise a population of placental stem cells, or a population of cells comprising placental stem cells, in a pharmaceutically-acceptable carrier, e.g., a saline solution or other accepted physiologically-acceptable solution for in vivo administration. Pharmaceutical compositions of the invention can comprise any of the placental stem cell populations, or placental stem cell types, described elsewhere herein. The pharmaceutical compositions can comprise fetal, maternal, or both fetal and maternal placental stem cells. The pharmaceutical compositions of the invention can further comprise placental stem cells obtained from a single individual or placenta, or from a plurality of individuals or placentae.

The pharmaceutical compositions of the invention can comprise any tumor cell suppressive number of placental stem cells. For example, a single unit dose of placental stem cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

The pharmaceutical compositions of the invention comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

5.6.1.3 Placental Stem Cell Conditioned Media

The placental stem cells of the invention can be used to produce conditioned medium that is tumor cell suppressive, that is, medium comprising one or more biomolecules secreted or excreted by the stem cells that have a detectable tumor cell suppressive effect on a plurality of one or more types of tumor cells. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least 30%, 40%, 50%, 60%, 70%, 80%, 90% confluence, or up to 100% confluence. Such conditioned medium can be used to support the culture of a separate population of placental stem cells, or stem cells of another kind. In another embodiment, the conditioned medium comprises medium in which placental stem cells have been differentiated into an adult cell type. In another embodiment, the conditioned medium of the invention comprises medium in which placental stem cells and non-placental stem cells have been cultured.

Thus, in one embodiment, the invention provides a composition comprising culture medium from a culture of placental stem cells, wherein said placental stem cells (a) adhere to a substrate; (b) express CD200 and HLA-G, or express CD73, CD105, and CD200, or express CD200 and OCT-4, or express CD73, CD105, and HLA-G, or express CD73 and CD105 and facilitate the formation of one or more embryoid-like bodies in a population of placental cells that comprise the placental stem cells, when said population is cultured under conditions that allow formation of embryoid-like bodies, or express OCT-4 and facilitate the formation of one or more embryoid-like bodies in a population of placental cells that comprise the placental stem cells when said population is cultured under conditions that allow formation of embryoid-like bodies; and (c) detectably suppress the growth or proliferation of a tumor cell or population of tumor cells. In a specific embodiment, the composition further comprises a plurality of said placental stem cells. In another specific embodiment, the composition comprises a plurality of non-placental cells. In a more specific embodiment, said non-placental cells comprise CD34+ cells, e.g., hematopoietic progenitor cells, such as peripheral blood hematopoietic progenitor cells, cord blood hematopoietic progenitor cells, or placental blood hematopoietic progenitor cells. The non-placental cells can also comprise other stem cells, such as mesenchymal stem cells, e.g., bone marrow-derived mesenchymal stem cells. The non-placental cells can also be one or more types of adult cells or cell lines. In another specific embodiment, the composition comprises an anti-proliferative agent, e.g., an anti-MIP-1α or anti-MIP-1β antibody.

In a specific embodiment, placental stem cell-conditioned culture medium or supernatant is obtained from a plurality of placental stem cells co-cultured with a plurality of tumor cells at a ratio of about 1:1, about 2:1, about 3:1, about 4:1, or about 5:1 placental stem cells to tumor cells. For example, the conditioned culture medium or supernatant can be obtained from a culture comprising about $1 \times 10^5$ placental stem cells, about $1 \times 10^6$ placental stem cells, about $1 \times 10^7$ placental stem cells, or about $1 \times 10^8$ placental stem cells, or more. In another specific embodiment, the conditioned culture medium or supernatant is obtained from a co-culture comprising about $1 \times 10^5$ to about $5 \times 10^5$ placental stem cells and about $1 \times 10^5$ tumor cells; about $1 \times 10^6$ to about $5 \times 10^6$ placental stem cells and about $1 \times 10^6$ tumor cells; about $1 \times 10^7$ to about $5 \times 10^7$ placental stem cells and about $1 \times 10^7$ tumor cells; or about $1 \times 10^8$ to about $5 \times 10^8$ placental stem cells and about $1 \times 10^8$ tumor cells.

In another specific embodiment of the method of suppressing the growth or proliferation of tumor cells, the conditioned culture medium or supernatant is culture medium or supernatant from a culture comprising a number of placental stem cells, alone or co-cultured with tumor cells, wherein the number of placental cells producing the conditioned medium is based on the weight of an individual to which the conditioned medium is to be administered. For example, the conditioned culture medium or supernatant can be conditioned medium or supernatant produced by a culture comprising about $1 \times 10^3$ placental stem cells per kg of a recipient's body weight, $5 \times 10^3$ placental stem cells/kg, $1 \times 10^4$ placental stem cells/kg, $5 \times 10^4$ placental stem cells/kg, $1 \times 10^5$ placental stem cells/kg, $5 \times 10^5$ placental stem cells/kg, $1 \times 10^6$ placental stem cells/kg, $5 \times 10^6$ placental stem cells/kg, $1 \times 10^7$ placental stem cells/kg, $5 \times 10^7$ placental stem cells/kg, or $1 \times 10^8$ placental stem cells/kg. In another specific embodiment, the conditioned culture medium or supernatant can be obtained from a co-culture comprising about $1 \times 10^3$ to about $5 \times 10^3$ placental stem cells/kg and about $1 \times 10^3$ tumor cells/kg; about $1 \times 10^4$ to about $5 \times 10^4$ placental stem cells/kg and about $1 \times 10^4$ tumor cells/kg; about $1 \times 10^5$ to about $5 \times 10^5$ placental stem cells/kg and about $1 \times 10^5$ tumor cells/kg; about $1 \times 10^6$ to about $5 \times 10^6$ placental stem cells/kg and about $1 \times 10^6$ tumor cells/kg; about $1 \times 10^7$ to about $5 \times 10^7$ placental stem cells/kg and about $1 \times 10^7$ tumor cells/kg; or about $1 \times 10^8$ to about $5 \times 10^8$ placental stem cells/kg and about $1 \times 10^8$ tumor cells/kg.

In a specific embodiment, the conditioned medium suitable for administration to a 70 kg individual comprises supernatant conditioned by about 70 million placental stem cells in about 200 mL culture medium.

Conditioned medium can be condensed to prepare an administrable pharmaceutical-grade product. For example, conditioned medium can be condensed to about 90%, 80%, 70%, 60%, 50%, 40%, 30%, 20%, 10% or more by removal of water, e.g., by evaporation, lyophilization, or the like. In a specific embodiment, for example, 200 mL conditioned medium from about 70 million placental stem cells can be condensed to a volume of about 180 mL, 160 mL, 140 mL, 120 mL, 100 mL, 80 mL, 60 mL, 40 mL, 20 mL or less. The conditioned medium can also be substantially dried, e.g., to a powder.

5.6.1.4 Matrices Comprising Placental Stem Cells

The invention further comprises matrices, e.g., hydrogels, scaffolds, and the like that comprise a tumor cell suppressive population of placental stem cells, or a tumor suppressive amount of placental stem cell-conditioned medium.

Placental stem cells of the invention can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796. The matrix, e.g., hydrogel, can be soaked with, or prepared using, placental stem cell-conditioned medium.

Placental stem cells of the invention can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Placental stem cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix of the invention is biodegradable.

In some embodiments of the invention, the formulation comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells of the invention or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the invention.

Examples of scaffolds that can be used in the present invention include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

Placental stem cells of the invention can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells of the invention can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells of the invention in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

5.6.2 Combination Therapies

Placental stem cells, and the placental stem cell compositions described herein, can be part of an anticancer therapy regimen that includes one or more other anticancer agents. Such anticancer agents are well-known in the art. Specific anticancer agents that may be administered to an individual having cancer include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide;

rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

5.6.3 Assays

The placental stem cells for the present invention can be used in assays to identify compounds or compositions that enhance the ability of placental stem cells to suppress the proliferation of tumor cells. Preferably, the assay is used for a type of cancer the proliferation of which can be suppressed by tumor cells in the absence of such compounds or compositions.

In a preferred embodiment, the placental stem cells of the present invention are combined with a test compound and tumor cells, e.g., a tumor cell line, and the effect of the placental stem cells on the tumor cells is determined, e.g., in the presence and in the absence of the test compound. A test compound enhances the ability of placental stem cells to suppress tumor cell proliferation if tumor cell proliferation is detectably reduced when the test compound is present compared to when it is absent. In one embodiment, for example, the invention provides a method of identifying a compound that enhances tumor suppression by placental stem cells, comprising contacting a first plurality of stem cells with a second plurality of tumor cells in the presence of said compound under conditions that allow tumor cell proliferation, wherein if said compound causes a detectable change in tumor cell proliferation compared to a plurality of tumor cells not contacted with said compound, said compound is identified as a compound that enhances tumor suppression by placental stem cells. The first plurality and second plurality can be the same number, or different numbers, of cells. In a specific embodiment, said tumor cells are tumor cells from a biopsy. In another specific embodiment, said tumor cells are cells of a tumor cell line.

The invention also provides a method of identifying, out of a panel or set of compounds, a compound or plurality of compounds that best enhances the suppression of tumor cell proliferation by placental stem cells. Because various cancers have different genetic and biochemical origins and characteristics, and differing etiologies, different compounds may be more or less effective in enhancing tumor cell suppression by placental stem cells. For example, such a panel or set of compounds can be a panel or set of anticancer or antineoplastic compounds, such as, without limitation, anticancer or antineoplastic compounds listed in Section 5.6.2, above. In such an embodiment, for example, tumor cells obtained from an individual having cancer can be tested with a panel of compounds, in the presence of placental stem cells, to identify one or a plurality of said anticancer or antineoplastic compounds best suited to treating the individual.

Thus, in one embodiment, the invention provides a method of selecting an compound from a plurality of compounds, comprising, for each compound in said plurality of compounds, contacting a first plurality of stem cells with a second plurality of tumor cells in the presence of an compound in said plurality of compounds under conditions that allow tumor cell proliferation, and identifying one or more of said compounds in said plurality of compounds that enhance tumor cell proliferation, compared to a plurality of tumor cells not contacted with said compound, to an extent greater than a predetermined standard. Such a predetermined standard can be, for example, a compound in said plurality of compounds that shows the greatest degree of enhancement of said compounds in said plurality of compounds; the 2, 3, 4, 5, 6, 7, 8, 9 or 10 compounds in said plurality of compounds showing the greatest degree of enhancement; the top 5%, 10%, 15%, 20% of said compounds in said plurality of compounds showing the greatest degree of enhancement; any of said plurality of compounds that enhances the tumor cell suppressive effect of placental stem cells, etc. Preferably, the method is used to select 1, 2, 3, 4 or 5 compounds to administer to said individual having cancer.

6. EXAMPLES

6.1 Example 1

Culture of Placental Stem Cells

Placental stem cells are obtained from a post-partum mammalian placenta either by perfusion or by physical disruption, e.g., enzymatic digestion. The cells are cultured in a culture medium comprising 60% DMEM-LG (Gibco), 40% MCDB-201(Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

The culture flask in which the cells are cultured is prepared as follows. T75 flasks are coated with fibronectin (FN), by adding 5 ml PBS containing 5 ng/ml human FN (Sigma F0895) to the flask. The flasks with FN solution are left at 37° C. for 30 min. The FN solution is then removed prior to cell culture. There is no need to dry the flasks following treatment. Alternatively, the flasks are left in contact with the FN solution at 4° C. overnight or longer; prior to culture, the flasks are warmed and the FN solution is removed.

Placental Stem Cells Isolated by Perfusion

Cultures of placental stem cells from placental perfusate are established as follows. Cells from a Ficoll gradient are seeded in FN-coated T75 flasks, prepared as above, at 50-100×$10^6$ cells/flask in 15 ml culture medium. Typically, 5 to 10 flasks are seeded. The flasks are incubated at 37° C. for 12-18 hrs to allow the attachment of adherent cells. 10 ml of warm PBS is added to each flask to remove cells in suspension, and mixed gently. 15 mL of the medium is then removed and replaced with 15 ml fresh culture medium. All medium is changed 3-4 days after the start of culture. Subsequent culture medium changes are performed, during which 50% or 7.5 ml of the medium is removed.

Starting at about day 12, the culture is checked under a microscope to examine the growth of the adherent cell colonies. When cell cultures become approximately 80% confluent, typically between day 13 to day 18 after the start of culture, adherent cells are harvested by trypsin digestion. Cells harvested from these primary cultures are designated passage 0 (zero).

Placental Stem Cells Isolated by Physical Disruption and Enzymatic Digestion

Placental stem cell cultures are established from digested placental tissue as follows. The perfused placenta is placed on a sterile paper sheet with the maternal side up. Approximately 0.5 cm of the surface layer on maternal side of placenta is scraped off with a blade, and the blade is used to remove a placental tissue block measuring approximately 1×2×1 cm. This placenta tissue is then minced into approximately 1 mm$^3$ pieces. These pieces are collected into a 50 ml Falcon tube and digested with collagenase IA (2 mg/ml, Sigma) for 30 minutes, followed by trypsin-EDTA (0.25%, GIBCO BRL) for 10 minutes, at 37° C. in water bath. The resulting solution is centrifuged at 400 g for 10 minutes at room temperature, and the digestion solution is removed. The pellet is resuspended to approximately 10 volumes with PBS (for example, a 5 ml pellet is resuspended with 45 ml PBS), and the tubes are centrifuged at 400 g for 10 minutes at room temperature. The tissue/cell pellet is resuspended in 130 mL culture medium, and the cells are seeded at 13 ml per fibronectin-coated T-75 flask. Cells are incubated at 37° C. with a humidified atmosphere with 5% $CO_2$. Placental Stem Cells are optionally cryopreserved at this stage.

Subculturing and Expansion of Placental Stem Cells

Cryopreserved cells are quickly thawed in a 37° C. water bath. Placental stem cells are immediately removed from the cryovial with 10 ml warm medium and transferred to a 15 ml sterile tube. The cells are centrifuged at 400 g for 10 minutes at room temperature. The cells are gently resuspended in 10 ml of warm culture medium by pipetting, and viable cell counts are determined by Trypan blue exclusion. Cells are then seeded at about 6000-7000 cells per cm$^2$ onto FN-coated flasks, prepared as above (approximately 5×10$^5$ cells per T-75 flask). The cells are incubated at 37° C., 5% $CO_2$ and 90% humidity. When the cells reached 75-85% confluency, all of the spent media is aseptically removed from the flasks and discarded. 3 ml of 0.25% trypsin/EDTA (w/v) solution is added to cover the cell layer, and the cells are incubated at 37° C., 5% $CO_2$ and 90% humidity for 5 minutes. The flask is tapped once or twice to expedite cell detachment. Once >95% of the cells are rounded and detached, 7 ml of warm culture medium is added to each T-75 flask, and the solution is dispersed by pipetting over the cell layer surface several times.

After counting the cells and determining viability as above, the cells are centrifuged at 1000 RPM for 5 minutes at room temperature. Cells are passaged by gently resuspending the cell pellet from one T-75 flask with culture medium, and evenly plating the cells onto two FN-coated T-75 flasks.

Using the above methods, populations of adherent placental stem cells are identified that express markers CD105, CD117, CD33, CD73, CD29, CD44, CD10, CD90 and CD133, and do not express CD34 or CD45. The cells may or may not express HLA-ABC and/or HLA-DR.

6.2 Example 2

Isolation of Stem Cells from Placental Structures

6.2.1 Materials & Methods

6.2.1.1 Isolation of the Phenotype of Interest

Five distinct populations of placental cells were obtained from the placentas of normal, full-term pregnancies. All donors provided full written consent for the use of their placentas for research purposes. Five populations of placental cells were examined: (1) placental perfusate (from perfusion of the placental vasculature); and enzymatic digestions of (2) amnion, (3) chorion, (4) amnion-chorion plate; and (5) umbilical cord. The various placental tissues were cleaned in sterile PBS (Gibco-Invitrogen Corporation, Carlsbad, Calif.) and placed on separate sterile Petri dishes. The various tissues were minced using a sterile surgical scalpel and placed into 50 mL Falcon conical tubes. The minced tissues were digested with 1× Collagenase (Sigma-Aldrich, St. Louis, Mo.) for 20 minutes in a 37° C. water bath, centrifuged, and then digested with 0.25% Trypsin-EDTA (Gibco-Invitrogen Corp) for 10 minutes in a 37° C. water bath. The various tissues were centrifuged after digestion and rinsed once with sterile PBS (Gibco-Invitrogen Corp). The reconstituted cells were then filtered twice, once with 100 μm cell strainers and once with 30 μm separation filters, to remove any residual extracellular matrix or cellular debris.

6.2.1.2 Cellular Viability Assessment and Cell Counts

The manual trypan blue exclusion method was employed post digestion to calculate cell counts and assess cellular viability. Cells were mixed with Trypan Blue Dye (Sigma-Aldrich) at a ratio of 1:1, and the viability of the cells was determined using a hemacytometer.

6.2.1.3 Cell Surface Marker Characterization

Cells that were HLA ABC$^-$/CD45$^-$/CD34$^-$/CD133$^+$ were selected for characterization. Cells having this phenotype were identified, quantified, and characterized by two of Becton-Dickinson flow cytometers, the FACSCalibur and the FACS Aria (Becton-Dickinson, San Jose, Calif., USA). The various placental cells were stained, at a ratio of about 10 μL of antibody per 1 million cells, for 30 minutes at room temperature on a shaker. The following anti-human antibodies were used: Fluorescein Isothiocyanate (FITC) conjugated monoclonal antibodies against HLA-G (Serotec, Raleigh, N.C.), CD10 (BD Immunocytometry Systems, San Jose, Calif.), CD44 (BD Biosciences Pharmingen, San Jose, Calif.), and CD105 (R&D Systems Inc., Minneapolis, Minn.); phycoerythrin (PE) conjugated monoclonal antibodies against CD44, CD200, CD117, and CD13 (BD Biosciences Pharmingen); Phycoerythrin-Cy5 (PE Cy5) conjugated Streptavidin and monoclonal antibodies against CD117 (BD Biosciences Pharmingen); phycoerythrin-Cy7 (PE Cy7) conjugated monoclonal antibodies against CD33 and CD10 (BD Biosciences); allophycocyanin (APC) conjugated streptavidin and monoclonal antibodies against CD38 (BD Biosciences Pharmingen); and biotinylated CD90 (BD Biosciences Pharmingen). After incubation, the cells were rinsed once to remove unbound antibodies and were fixed overnight with 4% paraformaldehyde (USB, Cleveland, Ohio) at 4° C.

The following day, the cells were rinsed twice, filtered through a 30 μm separation filter, and were evaluated on a flow cytometer.

Samples that were stained with anti-mouse IgG antibodies (BD Biosciences Pharmingen) were used as negative controls and were used to adjust the Photo Multiplier Tubes (PMTs). Samples that were single stained with anti-human antibodies were used as positive controls and were used to adjust spectral overlaps/compensations.

6.2.1.4 Cell Sorting and Culture

One set of placental cells (from perfusate, amnion, or chorion) was stained with 7-Amino-Actinomycin D (7AAD; BD Biosciences Pharmingen) and monoclonal antibodies specific for the phenotype of interest. The cells were stained at a ratio of 10 μL of antibody per 1 million cells, and were incubated for 30 minutes at room temperature on a shaker. These cells were then positively sorted for live cells expressing the phenotype of interest on the BD FACS Aria and plated into culture. Sorted (population of interest) and "All" (non-sorted) placental cell populations were plated for comparisons. The cells were plated onto a fibronectin (Sigma-Aldrich) coated 96 well plate at the cell densities listed in Table 1 (cells/cm$^2$). The cell density, and whether the cell type was plated in duplicate or triplicate, was determined and governed by the number of cells expressing the phenotype of interest.

TABLE 1

Cell plating densities
96 Well Plate Culture
Density of Plated Cells

| Conditions | Sorted | All | All Max. Density |
|---|---|---|---|
| Cell Source | | A | |
| Set #1: | 40.6 K/cm$^2$ | 40.6 K/cm$^2$ | 93.8 K/cm$^2$ |
| Set #2 | 40.6 K/cm$^2$ | 40.6 K/cm$^2$ | 93.8 K/cm$^2$ |
| Set #3: | 40.6 K/cm$^2$ | 40.6 K/cm$^2$ | 93.8 K/cm$^2$ |
| Cell Source | | B | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |
| Cell Source | | C | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |

Complete medium (60% DMEM-LG (Gibco) and 40% MCDB-201 (Sigma); 2% fetal bovine serum (Hyclone Labs.); 1× insulin-transferrin-selenium (ITS); 1× linoleic acid-bovine serum albumin (LA-BSA); $10^{-9}$ M dexamethasone (Sigma); $10^{-4}$ M ascorbic acid 2-phosphate (Sigma); epidermal growth factor 10 ng/mL (R&D Systems); and platelet-derived growth factor (PDGF-BB) 10 ng/mL (R&D Systems)) was added to each well of the 96 well plate and the plate was placed in a 5% $CO_2$/37° C. incubator. On day 7, 100 μL of complete medium was added to each of the wells. The 96 well plate was monitored for about two weeks and a final assessment of the culture was completed on day 12.

6.2.1.5 Data Analysis

FACSCalibur data was analyzed in FlowJo (Tree star, Inc) using standard gating techniques. The BD FACS Aria data was analyzed using the FACSDiva software (Becton-Dickinson). The FACS Aria data was analyzed using doublet discrimination gating to minimize doublets, as well as, standard gating techniques. All results were compiled in Microsoft Excel and all values, herein, are represented as average±standard deviation (number, standard error of mean).

6.2.2 Results

6.2.2.1 Cellular Viability

Post-digestion viability was assessed using the manual trypan blue exclusion method (FIG. 1). The average viability of cells obtained from the majority of the digested tissue (from amnion, chorion or amnion-chorion plate) was around 70%. Amnion yielded cells with an average viability of 74.35%±10.31% (n=6, SEM=4.21), chorion had an average viability of 78.18%±12.65% (n=4, SEM=6.32), amnion-chorion plate had an average viability of 69.05%±10.80% (n=4, SEM=5.40), and umbilical cord had an average viability of 63.30%±20.13% (n=4, SEM=10.06). Cells from perfusion, which did not undergo digestion, retained the highest average viability, 89.98±6.39% (n=5, SEM=2.86).

6.2.2.2 Cell Quantification

The five distinct populations of placenta derived cells were analyzed to determine the numbers of HLA ABC$^-$/CD45$^-$/CD34$^-$/CD133$^+$ cells. From the analysis of the BD FACS-Calibur data, it was observed that the amnion, perfusate, and chorion contained the greatest total number of these cells, 30.72±21.80 cells (n=4, SEM=10.90), 26.92±22.56 cells (n=3, SEM=13.02), and 18.39±6.44 cells (n=2, SEM=4.55) respectively. The amnion-chorion plate and umbilical cord contained the least total number of cells expressing the phenotype of interest, 4.72±4.16 cells (n=3, SEM=2.40) and 3.94±2.58 cells (n=3, SEM=1.49) respectively.

Similarly, when the percent of total cells expressing the phenotype of interest was analyzed, it was observed that amnion and placental perfusate contained the highest percentages of cells expressing this phenotype (0.0319%±0.0202% (n=4, SEM=0.0101) and 0.0269%±0.0226% (n=3, SEM=0.0130) respectively (FIG. 2). Although umbilical cord contained a small number of cells expressing the phenotype of interest (FIG. 2), it contained the third highest percentage of cells expressing the phenotype of interest, 0.020±0.0226% (n=3, SEM=0.0131) (FIG. 2). The chorion and amnion-chorion plate contained the lowest percentages of cells expressing the phenotype of interest, 0.0184±0.0064% (n=2, SEM=0.0046) and 0.0177±0.0173% (n=3, SEM=0.010) respectively (FIG. 2).

Consistent with the results of the BD FACSCalibur analysis, the BD FACS Aria data also identified amnion, perfusate, and chorion as providing higher numbers of HLA ABC$^-$/CD45$^-$/CD34$^-$/CD133$^+$ cells than the remaining sources. The average total number of cells expressing the phenotype of interest among amnion, perfusate, and chorion was 126.47±55.61 cells (n=15, SEM=14.36), 81.65±34.64 cells (n=20, SEM=7.75), and 51.47±32.41 cells (n=15, SEM=8.37), respectively. The amnion-chorion plate and umbilical cord contained the least total number of cells expressing the phenotype of interest, 44.89±37.43 cells (n=9, SEM=12.48) and 11.00±4.03 cells (n=9, SEM=1.34) respectively.

BD FACS Aria data revealed that the B and A cell sources contained the highest percentages of HLA ABC$^-$/CD45$^-$/CD34$^-$/CD133$^+$ cells, 0.1523±0.0227% (n=15, SEM=0.0059) and 0.0929±0.0419% (n=20, SEM=0.0094) respectively (FIG. 3). The D cell source contained the third highest percentage of cells expressing the phenotype of interest, 0.0632±0.0333% (n=9, SEM=0.0111) (FIG. 3). The C and E cell sources contained the lowest percentages of cells expressing the phenotype of interest, 0.0623±0.0249% (n=15, SEM=0.0064) and 0.0457±0.0055% (n=9, SEM=0.0018) respectively (FIG. 3).

After HLA ABC$^-$/CD45$^-$/CD34$^-$/CD133$^+$ cells were identified and quantified from each cell source, its cells were further analyzed and characterized for their expression of cell surface markers HLA-G, CD10, CD13, CD33, CD38, CD44, CD90, CD105, CD117, CD200, and CD105.

6.2.2.3 Placental Perfusate-Derived Cells

Perfusate-derived cells were consistently positive for HLA-G, CD33, CD117, CD10, CD44, CD200, CD90, CD38, CD105, and CD13 (FIG. 4). The average expression of each marker for perfusate-derived cells was the following: 37.15%±38.55% (n=4, SEM=19.28) of the cells expressed HLA-G; 36.37%±21.98% (n=7, SEM=8.31) of the cells expressed CD33; 39.39%±39.91% (n=4, SEM=19.96) of the cells expressed CD117; 54.97%±33.08% (n=4, SEM=16.54) of the cells expressed CD10; 36.79%±11.42% (n=4, SEM=5.71) of the cells expressed CD44; 41.83%±19.42% (n=3, SEM=11.21) of the cells expressed CD200; 74.25%±26.74% (n=3, SEM=15.44) of the cells expressed CD90; 35.10%±23.10% (n=3, SEM=13.34) of the cells expressed CD38; 22.87%±6.87% (n=3, SEM=3.97) of the cells expressed CD105; and 25.49%±9.84% (n=3, SEM=5.68) of the cells expressed CD13.

6.2.2.4 Amnion-Derived Cells

Amnion-derived cells were consistently positive for HLA-G, CD33, CD117, CD10, CD44, CD200, CD90, CD38, CD105, and CD13 (FIG. 5). The average expression of each marker for amnion-derived was the following: 57.27%±41.11% (n=3, SEM=23.73) of the cells expressed HLA-G; 16.23%±15.81% (n=6, SEM=6.46) of the cells expressed CD33; 62.32%±37.89% (n=3, SEM=21.87) of the cells expressed CD117; 9.71%±13.73% (n=3, SEM=7.92) of the cells expressed CD10; 27.03%±22.65% (n=3, SEM=13.08) of the cells expressed CD44; 6.42%±0.88% (n=2, SEM=0.62) of the cells expressed CD200; 57.61%±22.10% (n=2, SEM=15.63) of the cells expressed CD90; 63.76%±4.40% (n=2, SEM=3.11) of the cells expressed CD38; 20.27%±5.88% (n=2, SEM=4.16) of the cells expressed CD105; and 54.37%±13.29% (n=2, SEM=9.40) of the cells expressed CD13.

6.2.2.5 Chorion-Derived Cells

Chorion-derived cells were consistently positive for HLA-G, CD117, CD10, CD44, CD200, CD90, CD38, and CD13, while the expression of CD33, and CD105 varied (FIG. 6). The average expression of each marker for chorion cells was the following: 53.25%±32.87% (n=3, SEM=18.98) of the cells expressed HLA-G; 15.44%±11.17% (n=6, SEM=4.56) of the cells expressed CD33; 70.76%±11.87% (n=3, SEM=6.86) of the cells expressed CD117; 35.84%±25.96% (n=3, SEM=14.99) of the cells expressed CD10; 28.76%±6.09% (n=3, SEM=3.52) of the cells expressed CD44; 29.20%±9.47% (n=2, SEM=6.70) of the cells expressed CD200; 54.88%±0.17% (n=2, SEM=0.12) of the cells expressed CD90; 68.63%±44.37% (n=2, SEM=31.37) of the cells expressed CD38; 23.81%±33.67% (n=2, SEM=23.81) of the cells expressed CD105; and 53.16%±62.70% (n=2, SEM=44.34) of the cells expressed CD13.

6.2.2.6 Amnion-Chorion Plate Placental Cells

Cells from amnion-chorion plate were consistently positive for HLA-G, CD33, CD117, CD10, CD44, CD200, CD90, CD38, CD105, and CD13 (FIG. 7). The average expression of each marker for amnion-chorion plate-derived cells was the following: 78.52%±13.13% (n=2, SEM=9.29) of the cells expressed HLA-G; 38.33%±15.74% (n=5, SEM=7.04) of the cells expressed CD33; 69.56%±26.41% (n=2, SEM=18.67) of the cells expressed CD117; 42.44%±53.12% (n=2, SEM=37.56) of the cells expressed CD10; 32.47%±31.78% (n=2, SEM=22.47) of the cells expressed CD44; 5.56% (n=1) of the cells expressed CD200; 83.33% (n=1) of the cells expressed CD90; 83.52% (n=1) of the cells expressed CD38; 7.25% (n=1) of the cells expressed CD105; and 81.16% (n=1) of the cells expressed CD13.

6.2.2.7 Umbilical Cord-Derived Cells

Umbilical cord-derived cells were consistently positive for HLA-G, CD33, CD90, CD38, CD105, and CD13, while the expression of CD117, CD10, CD44, and CD200 varied (FIG. 8). The average expression of each marker for umbilical cord-derived cells was the following: 62.50%±53.03% (n=2, SEM=37.50) of the cells expressed HLA-G; 25.67%±11.28% (n=5, SEM=5.04) of the cells expressed CD33; 44.45%±62.85% (n=2, SEM=44.45) of the cells expressed CD117; 8.33%±11.79% (n=2, SEM=8.33) of the cells expressed CD10; 21.43%±30.30% (n=2, SEM=21.43) of the cells expressed CD44; 0.0% (n=1) of the cells expressed CD200; 81.25% (n=1) of the cells expressed CD90; 64.29% (n=1) of the cells expressed CD38; 6.25% (n=1) of the cells expressed CD105; and 50.0% (n=1) of the cells expressed CD13.

A summary of all marker expression averages is shown in FIG. 9.

6.2.2.8 BD FACS Aria Sort Report

The three distinct populations of placental cells that expressed the greatest percentages of HLA ABC, CD45, CD34, and CD133 (cells derived from perfusate, amnion and chorion) were stained with 7AAD and the antibodies for these markers. The three populations were positively sorted for live cells expressing the phenotype of interest. The results of the BD FACS Aria sort are listed in table 2.

TABLE 2

| | BD FACS Aria Sort Report | | |
|---|---|---|---|
| Cell Source | Events Processed | Events Sorted (Phenotype of Interest) | % Of Total |
| Perfusate | 135540110 | 51215 | 0.037786 |
| Amnion | 7385933 | 4019 | 0.054414 |
| Chorion | 108498122 | 4016 | 0.003701 |

The three distinct populations of positively sorted cells ("sorted") and their corresponding non-sorted cells were plated and the results of the culture were assessed on day 12 (Table 3). Sorted perfusate-derived cells, plated at a cell density of 40,600/cm$^2$, resulted in small, round, non-adherent cells. Two out of the three sets of non-sorted perfusate-derived cells, each plated at a cell density of 40,600/cm², resulted in mostly small, round, non-adherent cells with several adherent cells located around the periphery of well. Non-sorted perfusate-derived cells, plated at a cell density of 93,800/cm², resulted in mostly small, round, non-adherent cells with several adherent cells located around the well peripheries.

Sorted amnion-derived cells, plated at a cell density of 6,300/cm², resulted in small, round, non-adherent cells. Non-sorted amnion-derived cells, plated at a cell density of 6,300/cm², resulted in small, round, non-adherent cells. Non-sorted amnion-derived cells plated at a cell density of 62,500/cm² resulted in small, round, non-adherent cells.

Sorted chorion-derived cells, plated at a cell density of 6,300/cm², resulted in small, round, non-adherent cells. Non-sorted chorion-derived cells, plated at a cell density of 6,300/cm², resulted in small, round, non-adherent cells. Non-sorted chorion-derived cells plated at a cell density of 62,500/cm², resulted in small, round, non-adherent cells.

In other experiments, the initial populations of round, non-adherent cells described above, upon further culturing, adhered to the tissue culture surface, and assumed a characteristic fibroblastoid shape. Typically, the adherent cells lost expression of CD117, and were consistently CD10+, CD34−, CD105+ and CD200+.

6.3 Example 3

Differentiation of Placental Stem Cells

Adherent placental stem cells were differentiated into several different cell lineages. Adherent placental stem cells were isolated from the placenta by physical disruption of tissue from anatomical sites within the placenta, including the amniotic membrane, chorion, placental cotyledons, or any combination thereof, and umbilical cord stem cells were obtained by physical disruption of umbilical cord tissue.

Placental stem cells and umbilical cord stem cells were established in a medium containing low concentrations of fetal calf serum and limited growth factors. Flow cytometry analysis showed that placental stem cells typically exhibited a $CD200^+CD105^+CD73^+CD34^+CD45$-phenotype. Placental stem cells were found to differentiate down the adipocyte, chondrocyte and osteocyte lineages.

In an induction medium containing IBMX, insulin, dexamethasone and indomethacin, placental stem cells turned into fat laden adipocytes in 3 to 5 weeks. Under osteogenic induction culture conditions, placental stem cells were found to form bone nodules and have calcium depositions in their extracellular matrix. Chondrogenic differentiation of PDACs was performed in micropellets and was confirmed by formation of glycosaminoglycan in the tissue aggregates.

6.4 Example 4

Tumor Cell Suppression Using Placental Stem Cells

The placental stem cells described herein have the ability to suppress tumor cell growth and proliferation.

6.4.1 Materials and Methods

Tumor cell lines used included lymphoblastoid cell lines (LCL) from laboratory donors, and human cell lines purchased from ATCC (CML—CRL-2099; breast duct carcinoma—CRL-2343; acute lymphoblastic leukemia—CCL-119; colon carcinoma—CRL-5942). Cell lines used included human retinoblastoma, histiocytic lymphoma, lung carcinoma, acute leukemia, chronic myelogenous leukemia, colon adenocarcinoma, and breast carcinoma cell lines. LCL was obtained by culturing peripheral blood mononuclear cells in the presence of EBV from the B95.8 lytic EBV line and cyclosporin A. After two weeks in R20 medium (RPMI 1640 and bovine fetal serum (Celgro)) the cancer cells were maintained in R10 medium. Tumor cell lines were maintained in R10 medium.

Umbilical cord stem cells (passage 3) obtained by enzymatic digestion of umbilical cord tissue were plated in 96 well plates or in 24 well plates with or without transwell inserts. Co-cultures of placental stem cells and tumor cells were performed using cell numbers as indicated for specific experiments (see below). After culture, non-adherent tumor cells were collected and stained with 7-Amino-Actinomycin D (7-AAD) to assess viability.

For supernatant cytokine analysis, 50 µL culture supernatant was collected and analyzed on a LUMINEX® analyzer using an array of 25 cytokines: IL-1β, IL-1ra, IL-2R, IL-4, IL-5, IL-6, IL-7, IL-8, IL-10, IL-12p40, IL-13, IL-15, IL-17, TNF-α, IFN-α, IFN-γ, GM-CSF, MIP-1α, MIP-1, IP-10, MIG, Eotaxin, RANTES and MCP-1.

6.4.2 Results

6.4.2.1 Suppression of Various Tumor Cell Lines

In order to investigate the tumor suppression potential of placental stem cells, EBV transformed tumor cells were cultured either alone or with placental stem cells from different placental sites. LCL cells alone grew in culture over 17 days to approximately 40,000 cells. When LCL cells were cultured in the presence of placental stem cells from amnion-chorion (AC) or amniotic membrane (AM), or umbilical cord stem cells (UC), at a ratio of 1:2, however, the growth was suppressed to about 10,000 cells, a suppression of about 75% (FIG. 10).

Suppression of LCL proliferation by placental stem cells was compared to suppression by bone marrow-derived mesenchymal stem cells (BM-MSCs). LCL were cultured either alone, with placental or UC stem cells, or with BM-MSCs for six days, at which point cells in each condition were counted. Over the course of six days of culture, LCL alone proliferated to approximately 23,000 cells. In contrast, LCL+BM-MSCs at a 1:2 ratio resulted in approximately 38,000 LCL cells. Strikingly, however, the LCL+placental stem cell (1:2) condition resulted in only approximately 5,000 LCL cells in six days of culture, indicating that placental stem cells or umbilical cord stem cells were significantly more suppressive of LCL growth than BM-MSCs. See FIG. 11.

In order to determine the specificity of tumor suppression by placental stem cells, a panel of tumor cell lines was designed according to their relevance for human cancer epidemiology. All of the tumor cell lines were grown in suspension to facilitate separation from adherent placental stem cells. A titration experiment was performed to determine the tumor cell suppressive effect of placental stem cells on histiocytic lymphoma cells, leukemia (CML) cells, breast duct carcinoma cells, acute lymphoblastic leukemia cells or colon carcinoma cells combined in ratios of 0:1, 1:2, 1:1, 1.5:1 or 2:1 (FIG. 12). Placental cell lines appeared to suppress histiocytic lymphoma and CML to the greatest degree, resulting in approximately 60% and 48% suppression, respectively, at a 2:1 ratio of placental stem cells to tumor cells. However, these cell lines appeared only weakly dose-responsive at the tested ratios. The breast duct carcinoma cell line displayed a stronger tendency towards a dose response, as did the acute lymphoblastic leukemia (ALL) line. Notably, colon carcinoma cells showed weaker suppression at higher numbers of placental stem cells.

A subsequent experiment (FIG. 13A), performed in the same manner using a larger collection of tumor cell lines and a ratio of placental stem cells to tumor cells of 1:1, confirmed and expanded upon the results above. All tumor cell lines except breast carcinoma and ALL were suppressed by 50% to 75%, compared to tumor cells grown in the absence of placental stem cells. Breast carcinoma and ALL, however, which had in the prior experiment been moderately suppressed (10% to 20%) appeared to be activated by placental stem cells during co-culture. That is, co-culture appeared to increase the number of breast carcinoma and ALL cells.

Contact dependency of the suppression was assessed in a transwell experiment (FIG. 13B). HL showed the least contact dependency of suppression, 12%. Suppression of CML was 22% contact dependent, while suppression of CAC was 42%, and LCL was 51% contact dependent. Results generally showed an inverse relationship between the growth rate of the tumor cell line and contact dependency of suppression.

Taken together, the data suggest that retinoblastoma, histiocytic lymphoma, and CML are the most stably suppressed by placental stem cells.

6.4.2.2 Cytokine Secretion Profile

Figure 14B:
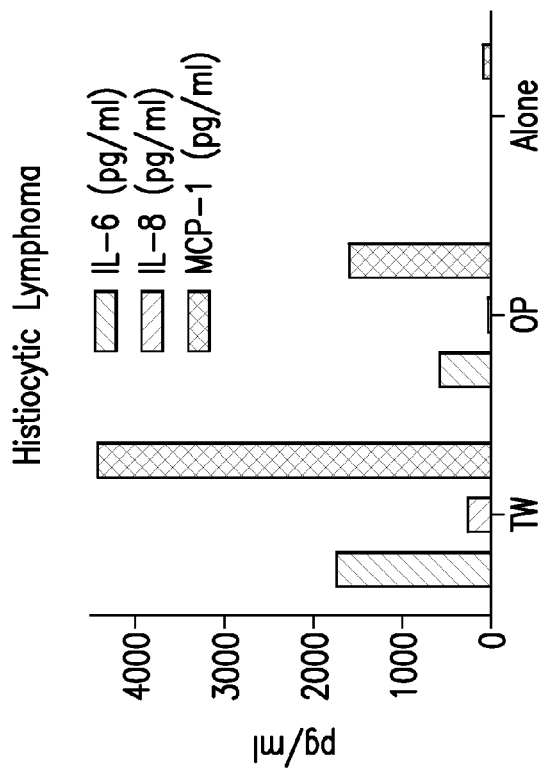
Figure 14A:
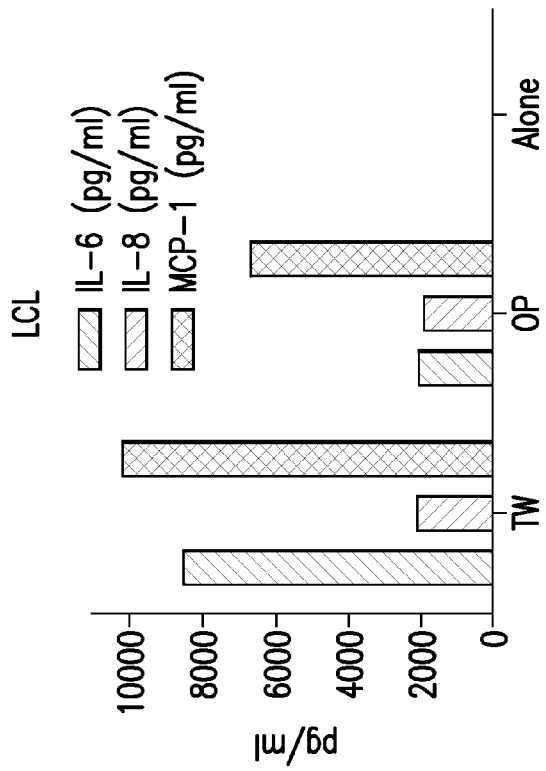

To investigate the secretion profile of placental stem cell tumor suppression, supernatants were collected from cultures of placental stem cells, and the supernatants analyzed using a LUMINEX® analyzer using an array of 25 cytokines. Two experiments were performed, one using only the LCL, and a second using the panel of eight tumor cell lines including the LCL cells. In the first experiment, after a six-day culture of placental stem cells with LCL cells, the tumor cells in suspension were collected, and live 7-AAD⁻ cells were counted. As seen in FIG. 14A, suppression of LCL proliferation by placental stem cells is strongly contact-dependent, as placental stem cells suppressed LCL proliferation in the open well co-culture, but not the transwell co-culture. The cytokine secretion profile, however, changed only slightly between the open well and transwell conditions (FIG. 14B). The LCL alone secreted MIP-1α and MIP-1β in the nanogram/ml range, whereas the co-culture contained IL-6, IL-8 and MCP-1 in amounts corresponding to those seen for placental stem cells alone. The values of MIP-1α and MIP-10 did not change significantly.

In order to determine the cytokine secretion profiles of a broader sample of tumor lines, the supernatants from the co-culture experiment described in FIGS. 15A and 15B were analyzed using the same array of 25 cytokines. The co-culture secretion profile for the LCL/PDAC co-culture was largely similar in that expected amounts of IL-6, IL-8 and MCP-1 were detected. No significant amount of MIP-1α/β was found, however. Among the other seven lines screened, histiocytic lymphoma displayed a similar profile to the LCL, whereas the other six lines had an overall subdued secretion profile.

6.4.2.3 Conclusions

From the data presented in the Example, it can be concluded that placental stem cells display tumor cell growth suppressive effects on a broad range of tumor cell lines, including histiocytic lymphoma, chronic myelogenous leukemia, colon adenocarcinoma, retinoblastoma; and lung carcinoma. These tumor cell lines derive from cell types of varying origin, e.g. epithelial, glandular, and hematopoietic, indicating that placental stem cells can be efficacious against a broad range of tumor types in a clinical setting. These effects are partly contact dependent, and the contact dependency may correlate with tumor growth speed. Of the eight tumor lines tested, breast carcinoma and ALL cells appear to be activated by co-culture with placental stem cells.

6.5 Example 5

Suppression of Chronic Myelogenous Leukemia Cells Using Placental Stem Cells Placental stem cells of the invention demonstrate the ability to suppress growth of megakaryoblastic leukemia cells in a contact independent manner.

6.5.1 Materials and Methods

Tumor cell lines used in these studies included chronic myelogenous leukemia cell line MEG-01 (megakaryoblastic leukemia cells; ATCC #CRL-2021), histiocytic lymphoma, and retinoblastoma cell lines.

Umbilical cord stem cells (UC), amnion-chorion stem cells (AC), bone marrow mesenchymal stem cells (BM-MSC), or human umbilical vein endothelial cells (HUVEC) were cultured alone or co-cultured with tumor cells for 6 days in 24-well tissue culture plates at a starting cell number of $5 \times 10^{-4}$ cells per well. Thus, where placental stem cells were co-cultured with tumor cells at a 1:1 ratio, $5 \times 10^{-4}$ cells of each cell type were seeded per well. Where 5:1 ratios were used, $25 \times 10^{-4}$ placental stem cells were seeded with $5 \times 10^{-4}$ tumor cells. Suppression of tumor cells was calculated by comparing the number of live (Annexin-V⁻ 7-AAD⁻) cells in co-culture to the number of live cells in control cultures (tumor cells alone).

For apoptosis studies, co-cultured MEG-01 cells were collected and stained with Annexin V and propidium iodide at 0, 3, and 6 days following initiation of co-culture, and analyzed by flow cytometry. For cell cycle analysis, co-cultured cells were fixed, permeabilized and stained with propidium iodide at 0, 1, 2, 3, 4 and 6 days following initiation of co-culture and analyzed for DNA content distribution by flow cytometry.

For supernatant cytokine analysis, 50 μl culture supernatant was collected and analyzed on a LUMINEX® analyzer for the following cytokines: platelet-derived growth factor-AA (PDGF-AA), granulocyte-monocyte colony stimulating factor (GM-CSF), growth-related oncogen-alpha (GROα), and leukemia inhibitory factor (LIF) secretion, tumor necrosis factor-alpha (TNF-α), fibroblast growth factor-2 (FGF-2), epidermal growth factor (EGF), soluble interleukin-2 (sIL2), and vascular endothelial growth factor (VEGF).

6.5.2 Results

To corroborate the enhanced suppression of tumor cell growth by placental stem cells relative to BM-MSC cells in an additional tumor cell line, growth suppression by placental stem cells was determined for chronic myelogenous leukemia (CML) cells. MEG-01 (megakaryoblastic leukemia) cells were cultured alone, or co-cultured with BM-MSCs, umbilical cord stem cells (UC) or amnion-chorion stem cells (AC) for six days at a ratio of 1:1. Percent suppression was determined according to the formula: 100-([#Annexin-V−, 7-AAD− cells in co-culture/#Annexin-V−, 7-AAD− cells cultured alone]*100). Co-culture of MEG-01 cells with BM-MSCs resulted in roughly 25% growth suppression after six days of co-culture. However, co-culture of MEG-01 cells with either umbilical cord or AC placental stem cells resulted in greater than 75% suppression after six days; co-culture with amnion-chorion cells resulted in greater than 90% suppression (FIG. 16A). Histiocytic lymphoma cells and retinoblastoma cells were also suppressed by co-culture with umbilical cord stem cells; however, suppression of these cell lines (HL: ~20%; Rb: ~50%) was moderate compared to the suppression seen in MEG-01 cells.

The time course of MEG-01 suppression by placental stem cells relative to suppression by BM-MSCs is shown in FIG. 16B. Dramatic suppression of MEG-01 cells is observed at day 2 for both BM-MSC and umbilical cord stem cell co-cultures; however, growth suppression is strongly maintained in the UC co-culture at day 6, while growth is only moderately suppressed by co-culture with BM-MSCs. These results demonstrate enhanced tumor cell growth suppression by placental stem cells relative to BM-MSCs in chronic myelogenous leukemia (CML) cells and corroborate the enhanced tumor suppressing effects of placental stem cells observed in LCL cells. The results also suggest that CML cells are particularly susceptible to suppression by placental stem cells relative to other blood tumor cell types, e.g. histiocytic lymphoma, or solid tumor cell types, e.g. retinoblastoma.

While not wishing to be bound to any particular mechanism or theory, an investigation into the manner by which tumor cell growth suppression can be effectuated by umbilical cord stem cells was undertaken. In particular, MEG-01 cells co-cultured with umbilical cord cells for 6 days were examined for the presence of apoptotic markers, analyzed for induction of cell cycle arrest, and assessed for maturation along the megakaryocyte lineage. Growth suppression did not appear to occur by induction of apoptosis, as no significant differences were found in the percentage of live (Annexin V−, PI−), apoptotic (Annexin V+, PI−) and necrotic (Annexin V+, PI+) MEG-01 cells co-cultured with umbilical cord stem cells when compared to MEG-01 cells cultured alone, or MEG-01 co-cultured with HUVEC cells (data not shown). Further, co-culture with umbilical cord stem cells did not appear to induce cell cycle arrest, as no significant differences in DNA content distribution were observed in MEG-01 cells co-cultured with umbilical cord stem cells, HUVEC, BM-MSC, or MEG-01 cells cultured alone (data not shown). In addition, MEG-01 growth suppression by umbilical cord stem cells did not appear to result from maturation along the megakaryocyte lineage, as MEG-01 cells co-cultured with umbilical cord stem cells, BM-MSCs, and HUVEC cells all showed similar levels of induction of the megakaryoblast maturation marker CD36 (data not shown). Thus, MEG-01 growth suppression by umbilical cord stem cells appears to occur in an apoptotic-, cell-cycle-, and maturation-independent manner.

6.5.2.1 Contact-Independent MEG-01 Growth Suppression by Placental Stem Cells To investigate the contact dependency of MEG-01 growth suppression by placental stem cells, a growth suppression assay was performed which utilized conditioned media from suppressed MEG-01/placental stem cell co-cultures (FIG. 17). MEG-01 cells were grown in RPMI-based media, and media was replaced conditioned media from MEG-01/umbilical cord stem cell co-cultures, MEG-01/BM-MSCs co-cultures, or MEG-01/HUVEC co-cultures at 1:2 or 1:10 (conditioned media to unconditioned media). Negative control cells (MEG alone) were grown without replacement of the starting media with conditioned media. MEG-01 cells were also directly co-cultured with umbilical cord stem cells as a positive control (MEG/UC). MEG-01 cells treated with MEG-01/umbilical cord stem cell co-culture conditioned media (1:2) was suppressed to the same degree as MEG-01 cells directly co-cultured with umbilical cord stem cells (MEG/UC), suggesting that soluble growth factor(s) produced by umbilical cord stem cells are responsible for the growth suppression of MEG-01 cells.

6.5.2.2 Cytokine Secretion Profile

To investigate whether soluble factors present in co-culture media may be involved in the suppression of MEG-01 cells, supernatants from MEG-01, UC stem cells, BM-MSCs, and HUVEC cells cultured alone, or MEG-01 cells co-cultured with UC stem cells, BM-MSC and HUVEC, respectively, were collected following a 6-day culture and analyzed for the presence of the following cytokines: FGF-2, TNF-alpha, GM-CSF, PDGF, EGF, GRO-alpha, sIL-2, VEGF, and LIF. PDGF-AA and GM-CSF were found to be highly secreted when PDAC cells were co-cultured with MEG-01 cells, at levels beyond those seen when either cell line is cultured alone (FIG. 18). GRO-α was highly secreted in PDAC/MEG-01 co-cultures, and similar levels of GRO-α were found in PDAC cells cultured alone.

6.5.2.3 Conclusions

Results from the growth suppression studies of megakaryoblastic leukemia cell line MEG-01 suggest that co-culture with placental stem cells results in an enhanced tumor cell growth suppression compared to co-culture with bone marrow mesenchymal stem cells. While not intending to be bound to any particular theory of operation, suppression appears to be a result of growth inhibition, and not induction of apoptosis, cell cycle arrest or maturation of MEG-01 cells along the megakaryocyte lineage. Suppression by placental stem cells may involve the action of soluble growth factors. Candidate factors include PDGF-AA, GM-CSF, GRO-α, and LIF. While not intending to be bound to any theory, it is believed that secretion of these factors may serve beneficial effects in vivo by enhancing the growth suppressive effect of placental stem cells through the attraction of innate and adaptive immune function.

Megakaryoblastic leukemia cells showed a higher sensitivity to placental stem cell co-culture compared to other tumor cell lines tested (histiocytic lymphoma, retinoblastoma), which suggests that chronic myelogenous leukemia may be particularly responsive to therapeutic applications of placental stem cell compositions.

6.6 Example 6

Suppression of Leukemia and Lymphoma Cells Using Placental Stem Cells

6.6.1 Materials and Methods

To further confirm and expand upon the results obtained in the MEG-01 chronic myelogenous lymphoma line, additional leukemia and lymphoma cell lines were tested for contact independent suppression by umbilical cord stem cells and amnion chorion stem cells. Cell lines used in this study included a number of leukemia cell lines available from ATCC, including megakaryoblastic lymphoma line MEG-01

(ATCC# CRL-2021); acute lymphoblast leukemia line CCRF-CEM (ATCC# CCL-119); acute T-cell leukemia line J.RT3-T3.5 (ATCC# TIB-153); histiocytic lymphoma U937 (ATCC# CRL-1593.2); bone marrow acute myelogenous leukemia line KG-1 (ATCC# CRL-8031); and chronic myelogenous leukemia line KU812 (ATCC# CRL-2099).

In brief, tumor cell lines were cultured alone, or co-cultured with umbilical cord (UC) stem cells or amnion-chorion (AC) placental stem cells, in both a direct co-culture (DC) and transwell (TW) format in 24-well tissue culture plated (unless otherwise specified), at 1:1 and 5:1 ratios (stem cells to tumor cells). After seven days in culture, tumor cells were collected from suspension, resuspended in 200 μl phosphate buffered saline and stained with Annexin V and propidium iodide. The number of live cells (Annexin V$^-$, PI$^-$ cells) was determined using a Becton Dickinson FACS Calibur Flow Cytometer.

6.6.2 Results

Results of the growth suppression assays on leukemia and lymphoma cell lines are presented in Table 3. Percentages represent the percentage of live cells remaining after 7-day co-culture, relative to control cells cultured alone.

TABLE 3

Suppression of Leukemia and Lymphoma Cell Lines by Umbilical Cord Stem Cells or Amnion-Chorion Stem Cells

| Stem Cell line (umbilical cord (UC); amnion-chorion (AC)) | Tumor Line | 1:1 TW | 1:1 DC | 5:1 TW | 5:1 DC | 1:1 TW MEG-01 | 1:1 DC MEG-01 |
|---|---|---|---|---|---|---|---|
| UC1 | CCRF-CEM | 49% | 32% | 16% | 3% | 42% | 16% |
| UC1 | CCRF-CEM | 48% | 34% | 16% | 7% | 60% | 21% |
| AC1 | CCRF-CEM | 79% | 49% | 43% | 31% | 55% | 41% |
| UC1 | J.RT3-T3.5 | 56% | 27% | 28% | 19% | 71% | 45% |
| AC1 | J.RT3-T3.5 | 74% | 105% | 69% | 34% | 34% | 28% |
| UC1 | U937 | 50% | 19% | 11% | 16% | 45% | 20% |
| UC1 | KG1 | 76% | 18% | 60% | 27% | 43% | 31% |
| UC1 | KG1 | 68% | 44% | 50% | 21% | 53% | 47% |
| UC2 | KG1 | 131% | 88% | 139% | 27% | 50% | 51% |
| UC3 | KG1 | 117% | 74% | 17% | 10% | 31% | 23% |
| UC4 | KG1 | 118% | 21% | 82% | 22% | 38% | 34% |
| AC1 | KG1 | 87% | 81% | 102% | 62% | 68% | 44% |
| UC4 | KU812 | 47% | 8% | 23% | 5% | 67% | 26% |
| AC1 | KU812 | 91% | 71% | 42% | 16% | 58% | 27% |
| AC1 | KU812 | 21% | 8% | 17% | NA | 48% | 27% |
| AC1 | KU812 | 12% | 17% | 12% | NA | 69% | 87% |
| AC2 | KU812 | 42% | 10% | 42% | 9% | 49% | 56% |

The CCRF-CEM cell line was suppressed by placental cell lines UC1 and AC1 in both a direct culture and transwell format. Direct culture with placental stem cells was slightly more effective at suppressing CCRF-CEM growth relative to the transwell format. A culture ratio of 5:1 was more effective at suppressing CCRF-CEM growth in both the direct and transwell format.

Similar results were observed for the U937 line. Suppression by direct co-culture was only slightly more effective than transwell suppression, with a 5:1 being the optimal culture ratio. KG-1 cells generally showed less sensitivity to co-culturing with umbilical cord or placental stem cells; however, growth suppression was still observed in both direct culture and transwell format when co-cultured with umbilical cord stem cell lines UC1, UC3 and UC4. Suppression of KG-1 cells by direct culture was more effective than suppression by transwell, with a culture ratio of 5:1 showing greater suppressive effect than 1:1. KU812 cells showed the highest sensitivity to co-culture with placental stem cells, as suppression was greater than 50% in nearly all conditions tested. Suppression by direct culture was more effective than transwell suppression; however, transwell suppression of KU812 was greater than 50% at a culture ration of 1:1.

To eliminate the possibility that growth suppression was due to nutrient depletion following seven days of co-culture in a T24 tissue culture well, co-cultures were carried out in T25 flasks using the same number of starting cells as was used in the 24-well assays (50×10$^3$ MEG-01 cells). Thus, co-cultures were effectively carried out in 10× the amount of nutrient as was provided in the T24 protocol. MEG-01 cells co-cultured with UC stem cells for seven days at a ratio of 1:1 were suppressed by 51%; when cultured at a ratio of 5:1, MEG-01 cells were suppressed by 69%. Similarly, when MEG-01 cells were co-cultured with AC placental stem cells for seven days at a ratio of 1:1, 53% suppression was observed; when co-cultured at a ratio of 5:1, 66% suppression was observed (data not shown). These results indicate that suppression of MEG-01 cells by placental stem cells in vitro is not due to the depletion of nutrients from the culture environment.

6.6.2.1 Conclusions

Taken together, these results demonstrate that growth suppression of leukemia and lymphoma cell lines by umbilical cord stem cells and amnion-chorion stem cells is robust and can occur in a contact independent fashion. While experiment-to-experiment variability was observed in the degree of suppression within the same tumor cell type, these results generally reflect the ability of placental stem cells, e.g. umbilical cord stem cells and amnion-chorion stem cells, to suppress the growth of a variety of blood tumor cell types in a direct or contact independent fashion. Both umbilical cord stem cells and amnion-chorion stem cells consistently demonstrated suppressive effects of greater than 50% in each of the tumor lines tested when directly co-cultured at a 5:1 ratio of stem cells to tumor cells (with the exception of KG1 cells treated with the AC1 stem cell line; 38% suppression observed). Thus, these data further support the utilization of placental stem cells in a therapeutic setting for the treatment of various tumors, and in particular support the use of placental stem cells for the treatment of blood tumors of various cell types, including megakaryoblastic lymphoma, acute lymphoblast leukemia, acute T-cell leukemia, histiocytic lymphoma, bone marrow acute myelogenous leukemia, and chronic myelogenous leukemia.

6.7 Example 7

Migration of Placental Stem Cells in Response to SDF-1

Placental stem cells of the invention demonstrate the ability to migrate in response to the presence of the chemoattractant SDF-1.

6.7.1 Materials and Methods

In order to test the migration ability of placental stem cells in response to a chemoattractant, placental stem cell migration was measured in the presence of Stromal cell-derived factor-1 (SDF-1) using the Cell Biolabs CYTOSELECT™ Cell Migration Assay Kit. The assay provides polycarbonate membrane inserts (8 μm pore size) in a 24-well plate. The membrane serves as a barrier to discriminate migratory cells from non-migratory cells. Migratory cells are able to extend protrusions towards chemoattractants (via actin cytoskeleton reorganization) and ultimately pass through the pores of the polycarbonate membrane. These migratory cells are then dissociated from the membrane and subsequently detected using a dye which fluoresces upon binding to cellular nucleic acids (CYQUANT® GR dye; Invitrogen Corporation, Carlsbad, Calif.). Briefly, umbilical cord placental stem cells were prepared in a cell suspension in serum free media. SDF-1 was directly added to the cell suspension alone, or in combination with a blocker of the SDF-1 receptor CXCR4 (AMD3100). Cells were assayed following 24 hours of incubation in a cell culture incubator.

6.7.2 Results

FIG. 19 shows that umbilical cord placental stem cells migrated to fetal calf serum and SDF-1. Placental stem cells incubated without the addition of serum or SDF-1 showed a migration of cells equivalent to 6.0 fluorescence units after 24 hours in culture. Addition of 10% FBS to the cell suspension resulted in the migration of cells equivalent to 12.7 fluorescence units after 24 hours. Addition of 1 μg/ml SDF-1 resulted in the migration of cells equivalent to 15.0 fluorescence units after 24 hours. However, addition of AMD3100, an inhibitor of the SDF-1 receptor CXCR4, significantly suppressed the placental stem cell migration in response to SDF-1. Migration of placental stem cells in the presence of both SDF-1 and AMD3100 amounted to 7.0 fluorescence units after 24 hours, close to the level of migration seen without the addition of SDF-1 or serum.

CONCLUSIONS

These results demonstrate that placental stem cells have the ability to migrate in response to a specific chemoattractant. The SDF-1 receptor CXCR4 is expressed on many tumor cells. Thus, these results indicate that co-administration of SDF-1 and placental stem cells into a tumor site may prolong the localization of placental stem cells to the targeted tumor site and facilitate placental stem cell-tumor cell interaction, thereby enhancing the tumor cell growth suppressive effects of placental stem cells.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A method of suppressing the proliferation of a plurality of tumor cells comprising contacting said plurality of tumor cells with a plurality of adherent $CD34^-$, $CD10^+$, $CD105^+$, $CD200^+$ placental stem cells for a time sufficient for said placental stem cells to suppress proliferation of said plurality of tumor cells, as compared to a plurality of said tumor cells not contacted with placental stem cells, wherein said tumor cells are histiocytic lymphoma cells, chronic myelogenous leukemia cells, acute T-cell leukemia cells, acute myelogenous leukemia cells, colon adenocarcinoma cells, retinoblastoma cells or lung carcinoma cells.

2. The method of claim 1, wherein said tumor cells are part of a solid tumor.

3. The method of claim 1, wherein said contacting is performed in vitro.

4. The method of claim 1, wherein said contacting is performed in vivo.

5. The method of claim 1, wherein said contacting is performed in a mammal.

6. The method of claim 5, wherein said mammal is a human.

7. The method of claim 1, wherein said contacting comprises administering said placental cells to said individual intravenously.

8. The method of claim 1, wherein said contacting comprises administering said placental cells to said individual at or adjacent to the site of a tumor.

9. The method of claim 1, wherein at least a portion of said placental stem cells have been engineered to express a cytokine.

10. The method of claim 9, wherein said cytokine is IFN-β or IL-2.

11. The method of claim 1, additionally comprising contacting said tumor cells with one or more anticancer compounds.

12. The method of claim 1, additionally comprising contacting said tumor cells with a plurality of mesenchymal stem cells.

13. The method of claim 12, wherein said mesenchymal stem cells are bone marrow-derived mesenchymal stem cells.

14. The method of claim 1, comprising administering at least $1 \times 10^7$ placental stem cells to said individual.

15. The method of claim 1, comprising administering at least $1 \times 10^8$ placental stem cells to said individual.

16. The method of claim 1, wherein said placental stem cells have been proliferated in vitro for no more than 30 population doublings.

17. The method of claim 1, wherein said placental stem cells have been proliferated in vitro for no more than 10 population doublings.

18. The method of claim 1, wherein said placental stem cells have been cryopreserved and thawed prior to said contacting.

19. The method of claim 1, wherein said placental stem cells suppress said tumor cell proliferation by at least 50% compared to proliferation of an equivalent number of tumor cells in the absence of said placental stem cells.

20. The method of claim 1, wherein said placental stem cells suppress said tumor cell proliferation by at least 75% compared to proliferation of an equivalent number of tumor cells in the absence of said placental stem cells.

21. The method of claim 1, comprising determining prior to said contacting that said placental stem cells detectably suppress the proliferation of sample tumor cells.

22. The method of claim 21, wherein said sample tumor cells are tumor cells of the same tissue origin as said tumor cells contacted with said placental stem cells.

23. The method of claim 22, wherein said sample tumor cells are tumor cells of an individual.

24. The method of claim 21, wherein said determining comprises determining that said sample tumor cells are detectably suppressed by direct contact with said placental stem cells.

25. The method of claim 21, wherein said determining comprises determining that said sample tumor cells are detectably suppressed by said placental stem cells without direct contact between said placental stem cells and said sample tumor cells.

* * * * *